(12) United States Patent
Niemoeller et al.

(10) Patent No.: US 9,821,032 B2
(45) Date of Patent: Nov. 21, 2017

(54) PHARMACEUTICAL COMBINATION FOR IMPROVING GLYCEMIC CONTROL AS ADD-ON THERAPY TO BASAL INSULIN

(75) Inventors: Elisabeth Niemoeller, Frankfurt am Main (DE); Louise Silvestre, Paris (FR); Gabor Boka, Paris (FR); Patrick Miossec, Paris (FR)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 0 days.

(21) Appl. No.: 13/467,707

(22) Filed: May 9, 2012

(65) Prior Publication Data

US 2013/0005649 A1 Jan. 3, 2013

(30) Foreign Application Priority Data

May 13, 2011 (EP) .................................... 11166111

(51) Int. Cl.
  *A61K 38/28* (2006.01)
  *A61K 38/26* (2006.01)
  *A61K 31/155* (2006.01)

(52) U.S. Cl.
  CPC ............ *A61K 38/26* (2013.01); *A61K 31/155* (2013.01); *A61K 38/28* (2013.01)

(58) Field of Classification Search
  CPC ....... A61K 38/28; A61K 38/26; A61K 31/155
  See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 3,984,696 A | 10/1976 | Collica et al. |
| 4,153,689 A | 5/1979 | Hirai et al. |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,006,718 A | 4/1991 | Lenhart |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Dorschug et al. |
| 5,177,058 A | 1/1993 | Dorschug |
| 5,187,177 A | 2/1993 | Garzaran |
| 5,227,293 A | 7/1993 | Stengelin et al. |
| 5,253,785 A | 10/1993 | Haber et al. |
| 5,272,135 A | 12/1993 | Takruri |
| 5,358,857 A | 10/1994 | Stengelin et al. |
| 5,370,629 A | 12/1994 | Michel et al. |
| 5,397,771 A | 3/1995 | Bechgaard et al. |
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |
| 5,478,323 A | 12/1995 | Westwood et al. |
| 5,496,924 A | 3/1996 | Habermann et al. |
| 5,506,203 A | 4/1996 | Backstrom et al. |
| 5,509,905 A | 4/1996 | Michel et al. |
| 5,514,646 A | 5/1996 | Chance et al. |
| 5,524,286 A | 6/1996 | Chiesa et al. |
| 5,534,488 A | 7/1996 | Hoffmann |
| 5,545,618 A | 8/1996 | Buckley et al. |
| 5,547,929 A | 8/1996 | Anderson, Jr. et al. |
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Dorschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |

(Continued)

FOREIGN PATENT DOCUMENTS

| | | |
|---|---|---|
| AU | 1986-62066 | 3/1987 |
| AU | 1987-75916 | 1/1988 |

(Continued)

OTHER PUBLICATIONS

Gavin, 1997, Diabetes Care, vol. 20, Issue 7, pp. 1183-1197.*
Gerich, 2010, abstract 830, 46th annual meeting of EASD, Stockholm, Sweden, Sep. 2010.*
Ratner 1, Jun. 2008, Abstract 433-P, 68th American Diabetes Association Meeting, San Francisco, Calif.*
Ratner 2, 2010, Diabetic Medicine, vol. 27, pp. 1024-1032.*
Sanofi, 2010, Press Release Apr. 15.*
Sharplin, 2009, Cardiovascular Diabetology, vol. 8, issue 3, pp. 1-8.*

(Continued)

*Primary Examiner* — Gyan Chandra

(74) *Attorney, Agent, or Firm* — McDonnell Boehnen Hulbert & Berghoff LLP

(57) ABSTRACT

The present invention refers to a pharmaceutical combination for use in glycemic control in diabetes type 2 patients.

14 Claims, 13 Drawing Sheets

(56) References Cited

U.S. PATENT DOCUMENTS

Figure 1:
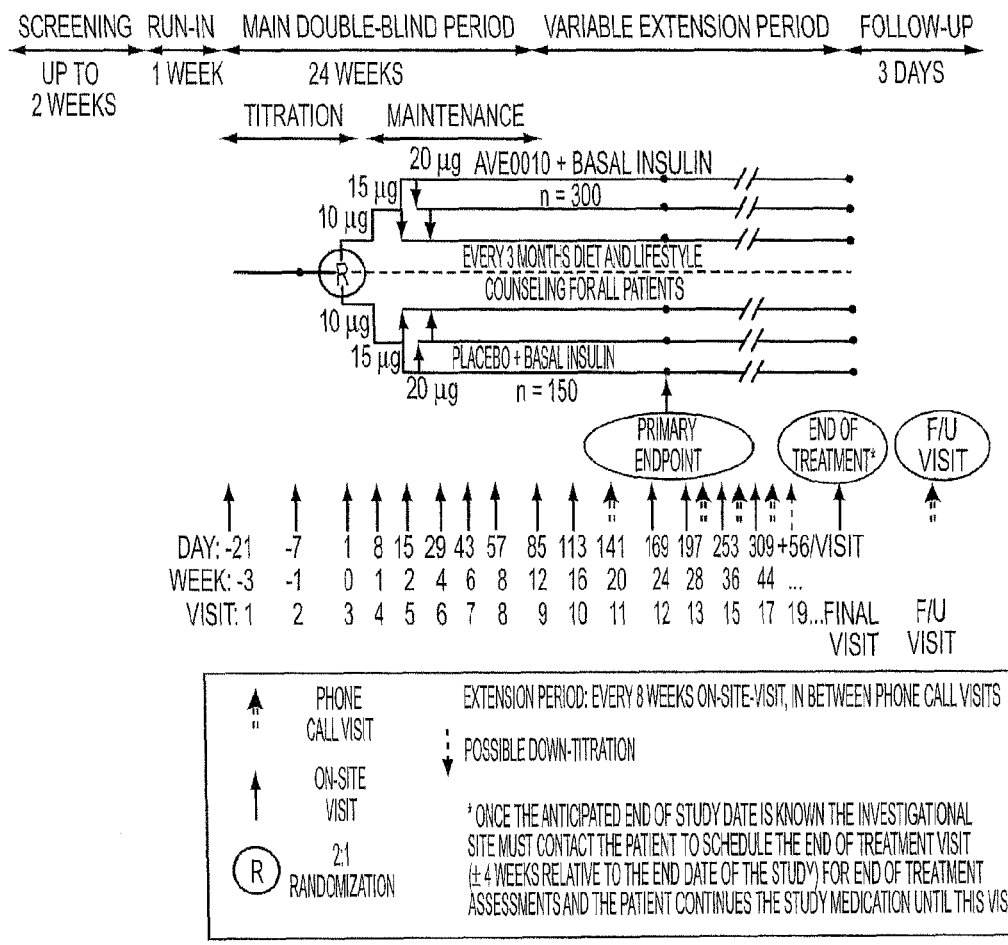

| Patent No. | Date | Inventor |
|---|---|---|
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,879,584 A | 3/1999 | Bianchetti et al. |
| 5,948,751 A | 9/1999 | Kimer et al. |
| 5,952,297 A | 9/1999 | DeFelippis et al. |
| 5,981,964 A | 11/1999 | McAuley et al. |
| 5,985,309 A | 11/1999 | Edwards et al. |
| 5,986,048 A | 11/1999 | Rubroeder et al. |
| 6,006,753 A | 12/1999 | Efendic |
| 6,034,054 A | 3/2000 | DeFelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Dorschug |
| 6,110,703 A | 8/2000 | Egel-Mitani et al. |
| 6,174,856 B1 | 1/2001 | Langballe et al. |
| 6,191,102 B1 | 2/2001 | DiMarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | DeSimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Briden et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,417,164 B1 | 7/2002 | Kolterman |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Dorschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | DeFelippis |
| 7,115,563 B2 | 10/2006 | Younis |
| 7,119,086 B2 | 10/2006 | Di Malta et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | DeFelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuhn et al. |
| 8,633,156 B2 | 1/2014 | Habermann et al. |
| 8,735,349 B2 * | 5/2014 | Silvestre et al. ............... 514/6.8 |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1* | 11/2002 | Gimeno .......................... 435/6 |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | DeFelippis et al. |
| 2003/0170691 A1 | 9/2003 | Gimeno |
| 2004/0037893 A1 | 2/2004 | Hansen et al. |
| 2004/0048783 A1 | 3/2004 | Brunner-Schwarz et al. |
| 2004/0092590 A1* | 5/2004 | Arterburn et al. ............ 514/560 |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | DeFelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |

(56) References Cited

U.S. PATENT DOCUMENTS

| | | |
|---|---|---|
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorg et al. |
| 2012/0316108 A1 | 12/2012 | Chen et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2014/0148384 A1 | 5/2014 | Boka et al. |
| 2014/0206611 A1 | 7/2014 | Becker et al. |
| 2014/0248365 A1 | 9/2014 | Rademacher et al. |

FOREIGN PATENT DOCUMENTS

| | | |
|---|---|---|
| CA | 1 173 388 | 8/1984 |
| CA | 1 341 203 | 11/1986 |
| CA | 1 258 427 | 8/1989 |
| CA | 1 336 329 | 7/1995 |
| CA | 2 662 084 | 3/2008 |
| CN | 1276731 | 12/2000 |
| CN | 1413582 | 4/2003 |
| CN | 101366692 | 2/2009 |
| CN | 101444618 | 6/2009 |
| CN | 101454019 | 6/2009 |
| CN | 101670096 | 3/2010 |
| DE | 196 37 230 | 3/1998 |
| DE | 10 2008 003 566 | 7/2009 |
| DE | 10 2008 003 568 | 7/2009 |
| DE | 10 2008 053 048 | 4/2010 |
| DE | 102008053048 A1 | 4/2010 |
| EP | 0 018 609 | 4/1980 |
| EP | 0 046 979 | 8/1981 |
| EP | 0 132 769 | 2/1985 |
| EP | 0 140 084 | 5/1985 |
| EP | 0 166 529 | 1/1986 |
| EP | 0 194 864 | 3/1986 |
| EP | 0 200 383 | 11/1986 |
| EP | 0 211 299 | 2/1987 |
| EP | 0 214 826 | 3/1987 |
| EP | 0 224 885 | 6/1987 |
| EP | 0 227 938 | 7/1987 |
| EP | 0 229 956 | 7/1987 |
| EP | 0 229 998 | 7/1987 |
| EP | 0 254 516 | 1/1988 |
| EP | 0 305 760 | 3/1989 |
| EP | 0 368 187 | 5/1990 |
| EP | 0 375 437 | 6/1990 |
| EP | 0 383 472 | 8/1990 |
| EP | 0419504 A1 | 4/1991 |
| EP | 0 419 504 | 1/1994 |
| EP | 0 600 372 | 6/1994 |
| EP | 0 668 282 | 8/1995 |
| EP | 0 668 292 | 8/1995 |
| EP | 0 678 522 | 10/1995 |
| EP | 0 837 072 | 4/1998 |
| EP | 0 845 265 | 6/1998 |
| EP | 0 885 961 | 12/1998 |
| EP | 1 076 066 | 2/2001 |
| EP | 1 172 114 | 1/2002 |
| EP | 1 222 207 | 7/2002 |
| EP | 1 196 444 | 4/2003 |
| EP | 1 523 993 | 4/2005 |
| EP | 1364029 B1 | 12/2005 |
| EP | 2 112 161 | 10/2009 |
| EP | 2 324 853 | 5/2011 |
| EP | 2329848 A1 | 6/2011 |
| EP | 2389945 A1 | 11/2011 |
| EP | 0 921 812 | 12/2011 |
| EP | 0 921 812 B2 | 12/2011 |
| EP | 2 387 989 | 7/2014 |
| FR | 2 456 522 | 12/1980 |
| GB | 0 835 638 | 5/1960 |
| GB | 0 840 870 | 7/1960 |
| GB | 1 527 605 | 10/1978 |
| GB | 1 554 157 | 10/1979 |
| JP | 61-212598 | 9/1986 |
| JP | 63-99096 | 9/1988 |
| JP | 2-218696 | 8/1990 |
| JP | 2-264798 | 10/1990 |
| JP | 3-504240 | 9/1991 |
| JP | 6-506444 | 7/1994 |
| JP | 2001-521004 | 11/2001 |
| JP | 2002-516880 | 6/2002 |
| JP | 2003-505347 | 2/2003 |
| JP | 2006-137678 | 1/2006 |
| JP | 2006-515267 | 5/2006 |
| JP | 2007-204498 | 8/2007 |
| JP | 2009-091363 | 4/2009 |
| JP | 2009-519961 | 5/2009 |
| JP | 2012-255040 | 12/2012 |
| RU | 2386631 | 9/2008 |
| RU | 2008-116057 | 10/2009 |
| TW | 157005 | 5/1991 |
| TW | 562806 | 11/2003 |
| WO | WO 83/00288 | 2/1983 |
| WO | WO 88/06599 | 9/1988 |
| WO | WO 89/10937 | 11/1989 |
| WO | WO 90/07522 | 7/1990 |
| WO | WO 90/11299 | 10/1990 |
| WO | WO 91/03550 | 3/1991 |
| WO | WO 91/16929 | 11/1991 |
| WO | WO 92/00321 | 1/1992 |
| WO | WO 92/12999 | 8/1992 |
| WO | WO 93/18786 | 9/1993 |
| WO | WO 94/14461 | 7/1994 |
| WO | WO 95/00550 | 1/1995 |
| WO | WO 95/24183 | 9/1995 |
| WO | WO 96/04307 | 2/1996 |
| WO | WO 96/07399 | 3/1996 |
| WO | WO 96/11705 | 4/1996 |
| WO | WO 96/32414 | 10/1996 |
| WO | WO 96/34882 | 11/1996 |
| WO | WO 96/41606 | 12/1996 |
| WO | WO 97/01331 | 1/1997 |
| WO | WO 97/48413 | 12/1997 |
| WO | WO 98/05351 | 2/1998 |
| WO | WO 98/08531 | 3/1998 |
| WO | WO 98/08871 | 3/1998 |
| WO | WO 98/08873 | 3/1998 |
| WO | WO 98/19698 | 5/1998 |
| WO | WO 98/30231 | 7/1998 |
| WO | WO 98/35033 | 8/1998 |
| WO | WO 98/39022 | 9/1998 |
| WO | WO 98/42749 | 10/1998 |
| WO | WO 98/56406 | 12/1998 |
| WO | WO 98/56418 | 12/1998 |
| WO | WO 99/07404 | 2/1999 |
| WO | WO 99/21573 | 5/1999 |
| WO | WO 99/21578 | 5/1999 |
| WO | WO 99/24071 | 5/1999 |
| WO | WO 99/25727 | 5/1999 |
| WO | WO 99/25728 | 5/1999 |

(56) References Cited

FOREIGN PATENT DOCUMENTS

| | | |
|---|---|---|
| WO | WO 99/40788 | 8/1999 |
| WO | WO 99/43708 | 9/1999 |
| WO | WO 99/46283 | 9/1999 |
| WO | WO 99/62558 | 12/1999 |
| WO | WO 00/23098 | 4/2000 |
| WO | WO 00/23099 | 4/2000 |
| WO | WO 00/29013 | 5/2000 |
| WO | WO 00/41546 | 7/2000 |
| WO | WO 00/66629 | 11/2000 |
| WO | WO 00/74736 | 12/2000 |
| WO | WO 01/02039 | 1/2001 |
| WO | WO0104156 | 1/2001 |
| WO | WO 01/12155 | 2/2001 |
| WO | WO 01/21154 | 3/2001 |
| WO | WO 01/25278 | 4/2001 |
| WO | WO 01/28555 | 4/2001 |
| WO | WO-0124814 A1 | 4/2001 |
| WO | WO 01/32157 | 5/2001 |
| WO | WO 01/37808 | 5/2001 |
| WO | WO 01/43762 | 6/2001 |
| WO | WO 01/51071 | 7/2001 |
| WO | WO 01/52937 | 7/2001 |
| WO | WO 02/00243 | 1/2002 |
| WO | WO 02/24214 | 3/2002 |
| WO | WO 02/064115 | 8/2002 |
| WO | WO 02/065985 | 8/2002 |
| WO | WO 02/066628 | 8/2002 |
| WO | WO 02/068660 | 9/2002 |
| WO | WO 02/070722 | 9/2002 |
| WO | WO 02/076495 | 10/2002 |
| WO | WO 02/079250 | 10/2002 |
| WO | WO 03/002021 | 1/2003 |
| WO | WO 03/020201 | 3/2003 |
| WO | WO 03/035028 | 5/2003 |
| WO | WO 03/035051 | 5/2003 |
| WO | WO 03/044210 | 5/2003 |
| WO | WO 03/053339 | 7/2003 |
| WO | WO 03/066084 | 8/2003 |
| WO | WO 03/094951 | 11/2003 |
| WO | WO 03/094956 | 11/2003 |
| WO | WO 03/101395 | 12/2003 |
| WO | WO 03/105888 | 12/2003 |
| WO | 2004/005342 | 1/2004 |
| WO | WO-2004003523 A1 | 1/2004 |
| WO | WO 2004/035623 | 4/2004 |
| WO | WO 2004/045592 | 6/2004 |
| WO | WO-2004050115 A2 | 6/2004 |
| WO | WO 2004/064862 | 8/2004 |
| WO | WO 2004/078196 | 9/2004 |
| WO | WO 2004/078197 | 9/2004 |
| WO | WO 2004/078198 | 9/2004 |
| WO | WO 2004/080480 | 9/2004 |
| WO | WO 2004/096854 | 11/2004 |
| WO | 2004/105781 | 12/2004 |
| WO | WO 2004/107979 | 12/2004 |
| WO | WO 2005/021022 | 3/2005 |
| WO | WO 2005/023291 | 3/2005 |
| WO | WO 2005/028516 | 3/2005 |
| WO | WO 2005/046716 | 5/2005 |
| WO | WO 2005/048950 | 6/2005 |
| WO | WO 2005/112949 | 12/2005 |
| WO | WO 2005/117948 | 12/2005 |
| WO | WO 2006/000567 | 1/2006 |
| WO | WO 2006/015879 | 2/2006 |
| WO | WO 2006/029634 | 3/2006 |
| WO | WO 2006/051103 | 5/2006 |
| WO | WO 2006/051110 | 5/2006 |
| WO | WO 2006/058620 | 6/2006 |
| WO | WO 2006/110551 | 10/2006 |
| WO | 2007/001150 | 1/2007 |
| WO | WO 2007/006307 | 1/2007 |
| WO | WO 2007/024700 | 3/2007 |
| WO | WO 2007/028394 | 3/2007 |
| WO | WO 2007/031187 | 3/2007 |
| WO | WO 2007/035665 | 3/2007 |
| WO | WO-2007035665 A1 | 3/2007 |
| WO | WO 2007/036299 | 4/2007 |
| WO | WO 2007/037607 | 4/2007 |
| WO | WO 2007/044867 | 4/2007 |
| WO | WO 2007/050656 | 5/2007 |
| WO | 2007/075534 | 7/2007 |
| WO | WO 2007/081824 | 7/2007 |
| WO | WO 2007/082381 | 7/2007 |
| WO | WO-2007081792 A2 | 7/2007 |
| WO | WO 2007/095288 | 8/2007 |
| WO | WO 2007/104786 | 9/2007 |
| WO | WO 2007/109221 | 9/2007 |
| WO | WO 2007/113205 | 10/2007 |
| WO | WO 2007/120899 | 10/2007 |
| WO | WO 2008/006496 | 1/2008 |
| WO | WO 2008/013938 | 1/2008 |
| WO | WO 2008/021560 | 2/2008 |
| WO | WO 2008/023050 | 2/2008 |
| WO | 2008/028914 | 3/2008 |
| WO | WO 2008/034881 | 3/2008 |
| WO | WO 2008/124522 | 10/2008 |
| WO | WO 2008/133908 | 11/2008 |
| WO | WO 2008/145323 | 12/2008 |
| WO | WO 2009/004627 | 1/2009 |
| WO | WO 2009/030498 | 3/2009 |
| WO | WO 2009/030499 | 3/2009 |
| WO | WO 2009/039963 | 4/2009 |
| WO | WO 2009/048959 | 4/2009 |
| WO | WO 2009/056569 | 5/2009 |
| WO | WO 2009/063072 | 5/2009 |
| WO | WO 2009/087081 | 7/2009 |
| WO | WO 2009/089181 | 7/2009 |
| WO | WO 2009/098318 | 8/2009 |
| WO | WO 2009/102467 | 8/2009 |
| WO | WO 2009/134380 | 11/2009 |
| WO | WO 2009/143014 | 11/2009 |
| WO | WO 2010/030670 | 3/2010 |
| WO | WO2010/043566 A2 | 4/2010 |
| WO | WO 2010/044867 | 4/2010 |
| WO | WO 2010/092163 | 8/2010 |
| WO | WO-2010089304 A1 | 8/2010 |
| WO | WO-2010138671 A1 | 12/2010 |
| WO | WO 2011/017554 | 2/2011 |
| WO | WO 2011/012719 | 3/2011 |
| WO | WO 2011/029892 | 3/2011 |
| WO | 2011/058082 | 5/2011 |
| WO | WO2011/058083 A1 | 5/2011 |
| WO | WO 2011/089203 | 7/2011 |
| WO | WO 2011/103575 | 8/2011 |
| WO | WO 2011/122921 | 10/2011 |
| WO | WO 2011/128374 | 10/2011 |
| WO | WO 2011/144673 | 11/2011 |
| WO | WO 2011/144674 | 11/2011 |
| WO | WO 01/93837 | 12/2011 |
| WO | WO 2011/147980 | 12/2011 |
| WO | WO 2011/157402 | 12/2011 |
| WO | WO 2011/160066 | 12/2011 |
| WO | WO 2012/012352 | 1/2012 |
| WO | WO 2012/028172 | 3/2012 |
| WO | WO 2012/055967 | 5/2012 |
| WO | WO 2012/065996 | 5/2012 |
| WO | WO 2012/066086 | 5/2012 |
| WO | WO 2012/080320 | 6/2012 |
| WO | WO 2012/104342 | 8/2012 |
| WO | WO 2012/125569 | 9/2012 |
| WO | 2012/156296 | 11/2012 |
| WO | 2012/156299 | 11/2012 |
| WO | WO 2012/177929 | 12/2012 |
| WO | 2013/060850 | 5/2013 |
| WO | WO 2014/017849 | 1/2014 |
| WO | WO 2014/118355 | 8/2014 |
| WO | WO 2014/202483 | 12/2014 |
| WO | WO-2015059302 A1 | 4/2015 |

OTHER PUBLICATIONS

Fonseca, 2012, Diabetes Care, vol. 35, pp. 1225-1231.*
Akbar, 2003, Saudi Med Journal, vol. 24, issue 10, pp. 1109-1112.*

(56) References Cited

OTHER PUBLICATIONS

Christensen M. et al., "Lixisenatide, a Novel GLP-1 Receptor Agonist for the Treatment of Type 2 Diabetes Mellitus", IDrugs 12(8):503-513 (2009).
Office Action dated Apr. 8, 2013 from related U.S. Appl. No. 13/432,811.
Office Action dated Apr. 17, 2013 from related U.S. Appl. No. 13/467,757.
The Diabetes Control and Complications Trial Research Group, "The Effect of Intensive Treatment of Diabetes on the Development and Progression of Long-Term Complications in Insulin-Dependent Diabetes Mellitus," The New England Journal of Medicine (1993), vol. 329, pp. 977-986.
International Search Report dated Jul. 31, 2012 issued in PCT/EP2012/058749.
International Preliminary Report on Patentability for PCT/EP2012/058779, dated Oct. 18, 2013.
Written Opinion of the International Search Authority for PCT/EP2012/058779, dated Jul. 25, 2013.
U.S. Appl. No. 12/617,811, filed Nov. 13, 2009 to Silvestre et al.
U.S. Appl. No. 12/617,805, filed Nov. 13, 2009 to Silvestre et al.
U.S. Appl. No. 13/700,631, filed Nov. 11, 2012 to Becker et al.
Non-Final Office Action from U.S. Appl. No. 12/617,811; dated Apr. 27, 2011, pp. 1-10.
Non-Final Office Action from U.S. Appl. No. 12/617,811; dated Oct. 27, 2011, pp. 1-13.
Non-Final Office Action from U.S. Appl. No. 12/617,811; dated Jun. 21, 2012, pp. 1-7.
Final Office Action from U.S. Appl. No. 12/617,811; dated Jan. 4, 2013, pp. 1-6.
Non-Final Office Action from U.S. Appl. No. 12/617,811; dated Jan. 14, 2015, pp. 1-15.
Final Office Action from U.S. Appl. No. 12/617,805; dated Jan. 13, 2015, pp. 1-11.
Non-Final Office Action from U.S. Appl. No. 12/617,805; dated Jul. 24, 2014, pp. 1-12.
Final Office Action from U.S. Appl. No. 12/617,805; dated Feb. 11, 2013, pp. 1-13.
Non-Final Office Action from U.S. Appl. No. 12/617,805; dated May 2, 2012, pp. 1-11.
Final Office Action from U.S. Appl. No. 12/617,805; dated Jan. 12, 2012, pp. 1-14.
Non-Final Office Action from U.S. Appl. No. 12/617,805; dated May 10, 2011, pp. 1-12.
Extended European Search Report dated Mar. 24, 2010 from related European Application No. 09175876.3, pp. 1-4.
European Application 09175 877.1, Extended European Search Report, p. 1-5 (dated Apr. 29, 2010).
Extended European Search Report issued by the European Patent Office for European Application No. 14197154.9, dated Apr. 8, 2015 (pp. 1-7).
The Extended European Search Report for EP Application No. 10164368.2, dated Oct. 14, 2010, pp. 1-6.
International Search Report and Written Opinion of the International Searching Authority for International Application No. PCT/EP/2011/058764, dated Jun. 30, 2011, pp. 1-9.
18th World Medical Assembly (WMA) Declaration of Helsinki—Ethical Principles for Medical Research Involving Human Subjects. pp. 1-8 (1964).
The Expert Committee on the Diagnosis and Classification of Diabetes Mellitus. Report of the Expert Committee on the Diagnosis and Classification of Diabetes Mellitus Diabetes Care, Jan. 1998, 21:Supplement 1 S5-S19.
Guidance for Industry, US Department of Health and Human Services, Food and Drug Administration, Center for Drug Evaluation and Research (COER), pp. 1-11, Feb. 2014.
Sampson et al., "Second symposium on the definition and management of anaphylaxis: summary report—Second National Institute of Allergy and Infectious Disease/Food Allergy and Anaphylaxis Network symposium." Journal of Allergy and Clinical Immunology, 117(2):391-397 (2006).
Ahren et al., Abstract "Efficacy and Safety of Lixisenatide QD Morning and Evening Injections vs Placebo in T2DM Inadequately Controlled on Metformin (GetGoal-M)" presented at the World Diabetes Congress in Dubai, Dec. 5-8, 2011, one page.
American Diabetes Association Workgroup on Hypoglycemia, "Defining and reporting hypoglycemia in diabetes," Diabetes Care 28(5):1245-9 (2005).
Arnolds et al., "Insulin Glargine (GLAR) plus Metformin (MET): An Efficacious and Safe Regimen that can be combined with Exenatide (EXE) or Sitagliptin (SITA)" Diabetes, vol. 58, No. Suppl. 1, Jun. 2009 (Jun. 2009) , p. A 141 (Mar. 17, 2010).
Barnett "Lixisenatide: evidence for its potential use in the treatment of type 2 diabetes." Core Evidence 6:67-79 (2011).
Barnett, "Insulin glargine in the treatment of type 1 and type 2 diabetes" Vascular Health and Risk Management 2:59-67 (2006).
Bolen et al., "Systematic Review: Comparative Effectiveness and Safety of Oral Medications for Type 2 Diabetes Mellitus," Ann. Intern. Med. 147:386-399 (2007).
Campas et al., "AVE-0010 GLP-1 Receptor Agonist Treatment of Diabetes", Drugs of the Future 33(10):838-40 (2008).
Charles et al., "Prevention of Type 2 Diabetes Role of Metformin" Review Article, Drugs 1999; 58 Suppl. 1:71-73 (1999).
Christensen et al., "Lixisenatide for type 2 diabetes mellitus," Expert Opin. 20(4):549-57 (2011).
Community register of medicinal products for human use, "Lyxumia" European Commision—Public Health, p. 1-2 (May 2, 2013).
Crapo et al., "Postprandial plasma-glucose and -insulin responses to different complex carbohydrates," Diabetes 26(12):1178-83 (1977).
Cryer "Hypoglycemia is the limiting factor in the management of diabetes," Diabetes Metab. Res. Rev. 15:42-46 (1999).
D'Alessio et al., "GLP-1 Receptor Agonists: Strategies for PPG Control," Medical Nursing Edu., 3:1-26 (Jan. 2011).
DeFronzo "Effects of Exenatide (Exendin-4) on Glycemic Control and Weight Over 30 Weeks in Metformin-Treated Patients with Type 2 Diabetes", Diabetes Care 28(5):1092-1100 (2005).
DeFronzo "Pathogenesis of Type 2 Diabetes Implications for Metformin" Short Communication, Drugs 1999; 58(Suppl 1):29-30 (Sep. 1999).
Distiller et al., Poster: "Pharmacokinetics and Pharmacodynamics of a New GLP-1 Agonist AVE0010 in Type 2 Diabetes Patients" Meeting: 68th Scientific Sessions (2008) Poster No. 520-P.
Dormandy et al., "Secondary prevention of macrovascular events in patients with type 2 diabetes in the PROactive Study (PROspective pioglitAzone Clinical Trial in macrovascular Events): a randomised controlled trial," Lancet. 366(9493):1279-89 (2005).
Executive Summary, "Standards of Medical Care in Diabetes—2009" Diabetes Care,32(Suppl. 1):S6- S12 (Jan. 2009).
Gallwitz, "Liraglutide. GLP-1 Receptor Agonist Treatment of Type 2 Diabetes Treatment of Obesity," Drugs of the Future, 33(1):13-20 (2008).
Garber et al., "Liraglutide versus glimepiride monotherapy for type 2 diabetes (LEAD-3 Mono): a randomised, 52-week, phase III, double blind, parallel-treatment trial", The Lancet, 373(9662):473-81 (2009).
Goldstein et al.. Tests of Glycemia in Diabetes. Diabetes Care 18(6):896-909 (1995).
"Guideline for Management of Postmeal Glucose," International Diabetes Federation, pp. 1-27, Lesaffre Printers, ISBN 2-930229-48-9 (2007).
Hanas et al., "2010 Consensus Statement on the Worldwide Standardization of the Hemoglobin A1C Measurement." Diabetes Care 33(8):1903-04 (2010).
Hanna et al., Canadian Diabetes Association Clinical Practice Guidelines Expert Committee "Pharmacologic Management of Type 2 Diabetes" Canadian Journal of Diabetes, 27(Supp 2):S37-S42 (Dec. 2003).
Kapitza et al., Abstract "Pharmacodynamic Characteristics of Lixisenatide QD vs Liraglutide QD in Patients with T2DM Inad-

(56) References Cited

OTHER PUBLICATIONS equately Controlled with Metformin" presented at the World Diabetes Congress in Dubai, Dec. 5-8, 2011, one page.
Kanazawa et al., "Criteria and Classification of Obesity in Japan and Asia-Oceania", Asia Pacific J. Clin Nutr. 11 (Suppl):S732-S737 (2002).
Inpharma, Product News. "AVE0010 set to deliver in type 2 diabetes mellitus," Database Adisnews, retrieved from STN 2008, pp. 1-3.
Insulinpraparat Wikipedia, http://de.wikipedia.org/wiki/Insulinpr%C3%A4parat, pp. 1-15 (Feb. 5, 2013).
Inzucchi et al. "Management of Hyperglycemia in Type 2 Diabetes: A Patient-Centered Approach" Diabetes Care, 35:1364-79 (2012).
"Lixisenatide, Chemical Structure CID 16139342, Pubchem, accessed Feb. 5, 2015 at URLpubchem.ncbi.nlm.nih.gov/summary/summary.cgi?sid=135267128&viewopt=Deposited, pp. 1-3."
Medline Plus, "Obesity" available at http://www.nlm.nih.gov/medlineplus/obesity.html, Retrieved Aug. 22, 2013, one page.
Moretto et al., "Efficacy and Tolerability of Exenatide Monotherapy Over 24 Weeks in Antidiabetic Drug-Naive Patients with Type 2 Diabetes: A Randomized, Double-Blind, Placebo-Controlled, Parallel-Group Study", Clinical Therapeutics, 30(8)1448-60 (2008).
Nauck et al., "Comparative evaluation of incretin-based antidiabetic medications and alternative therapies to be added to melformin in the case of monotherapy failure," Journal of Diabetes Investigation 1(1-2):24-36 (2010).
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
NCT00688701 Clinical Trials.gov "GLP-1 Receptor Agonist Lixisenatide in Patients with Type 2 Diabetes for Glycemic Control and Safety Evaluation in Monotherapy (GETGOAL-MONO)" accessed Jul. 27, 2014; pp. 1-5.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6018; Clinical trial EudraCT 2007-005887-29, "GETGOAL-MONO" accessed Jul. 27, 2014; pp. 1-16.
Park et al., "PPARalpha agonis fenofibrate improves diabetic nephropathy in db/db mice," Kidney International, (2006). 69:1511-17.
Parkin C. "Guideline for Management of Postmeal Glucose" International Diabetes Federation, pp. 1-31 (2007).
Pugeat et al., "Insulin Resistance, Polycystic Ovary Syndrome and Metformin" Review Article, Drugs 1999; 58(Suppl 1):41-46 (1999).
Quianzon & Shomali, "Lixisentide-Once Daily Glucagon-like Peptide-1 receptor Agonist in the Management of Type 2 Diabetes", US Endicronology, 7(2):104-9 (2011).

Raccah et al., "When Basal Insulin Therapy in Type 2 Diabetes Mellitus is Not Enough—What Next?" Diabetes Metabolism Research and Reviews 23:257-64 (2007).
Ratner et al. Abstract 131 "Post-meal pharmacodynamics profile of AVE0010, a once-daily GLP-1 receptor agonist, in patients with type 2 diabetes inadequately controlled on metformin" Diabetologia 52(Suppl. 1): S60, #131 (2009).
Zimmet, et al. "Clinical Efficacy of Metformin against Insulin Resistance Parameters, Sinking the Iceberg" Review Article Drugs 1999: 58(Suppl 1):21-28 (1999).
Richter, von Margret, "Oldtimer als Newcomer" Pharmazie, pp. 1-9; http://www.pharmazeutische-zeitung.de/pza/2002-12/pharm1.htm. (Feb. 2002). With English Translation.
Riddle et al., Contributions of Basal and Postprandial Hyperglycemia Over a Wide Range of A 1 C Levels Before and After Treatment Intensification in Type 2 Diabetes, Diabetes Care 34:2508-2514 (published online Oct. 25, 2011).
Riddle et al., "Adding Once-Daily Lixisenatide for Type 2 Diabetes Inadequately Controlled with Newly Initiated and Continuously Titrated Basal Insulin Glargine" Diabetes Care, pp. 2497-2503 (2013).
Rosenstock et al., Abstract, "71st Scientific Sessions" http://www.call4abstracts.com/ada/ada11d1lb/index.php 02:22:24 pp. 1-3, (Nov. 2011).
Rosenstock et al., Poster "Efficacy and safety of lixisenatide once daily vs exenatiide twice daily in type 2 DM inadequately controlled on metformin (GetGoal-X)." 71st Scientific Sessions (Nov. 2011).
Rosenstock et al., OP 25 GLP-1 Based therapies, Abstract 145 "Dose range effects of the new once daily GLP-1 receptor agonist AVE0010 added to metformin in type 2 diabetes," Diabetologia 51 (Supplement 1):S66 (2008).
Rosenstock et al., Abstract, 564P "Post-meal effects of AVE0010, a once-daily GLP-1 receptor agonist, in type 2 diabetes inadequately controlled on metformin," Diabetes 58(Suppl. 1):A151-A152 (Jun. 1, 2009).
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.
St. John Providence Health Center, "Preventing Obesity" http://www.stjohnprovidence.org/HealthInfolib/swarticle.aspx?type=85&id=P07863, Retrieved Aug. 22, 2013, pp. 1-2.
Summary of Product Characteristics Lyxumia 10 micrograms solution for injection, pp. 1-93, with European Medicines Agency product information, p. 94, published Mar. 14, 2013.
Tews et al., "Enhanced protection against cytokine- and fatty acid-induced apoptosis in pancreatic beta cells by combined treatment with glucagon-like peptide-1 receptor agonists and insulin analogues." Horm Metab Res. 40(3):172-80 (2008).
UK Prospective Diabetes Study (UKPDS) Group "Intensive blood-glucose control with sulphonylureas or insulin compared with conventional treatment and risk of complications in patients with type 2 diabetes (UKPDS 33)" The Lancet vol. 352 p. 837-853 (Sep. 12, 1998).
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (2008).

(56) References Cited

OTHER PUBLICATIONS

Wiernsperger, et al. "The Antihyperglycaemic Effect of Metformin Therapeutic and Cellular Mechanisms" Review Article, Drugs 1999:58(Suppl 1):31-39 (1999).
Yki-Jarvinen et al., "Insulin glargine or NPH combined with metformin in type 2 diabetes: the LANMET study." Diabetologia 49(3):442-51 (2006).
Yki-Jarvin et al., "Thiazolidinediones," N Engl J Med. 351(11):1106-18 (2004).
Translation of pp. 750, 753 and 754 of Igaku No Ayumi, "Incretin Receptors," May 2010, vol. 233; No. 9: 750-754, pp. 1-4.
Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 2346 and 2348 of Rinsho To Kenkyu, "Effectiveness of Combination Therapy Using Voglibose and Insulin in Patients with NIDDM," 1997, vol. 74, No. 9: 2346-2352, pp. 1-3.
Translation of pp. 121 and 124 of Igaku To Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Bethel & Feinglos, "Basal insulin therapy in type 2 diabetes." J Am Board Fam Pract. 18(3):199-204 (2005).
BYETTA—Summary of Product Characteristics, updated Jan. 27, 2015, last accessed Apr. 18, 2015, pp. 1-12.
Childs et al., "Defining and Reporting Hypoglycemia in Diabetes," Diabetes Care 28(5):1245-9 (May 2005).
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi and Zealand Pharma Press Release (Evaluate), "Additional Positive Results from Global Phase III Program With Lixisenatide for Type 2 Diabetes", (Apr. 12, 2011) pp. 1-3.
Ratner et al., Abstract "A dose-finding study of the new GLP-1 agonist AVE0010 in type 2 diabetes insufficiently controlled with melformin," Diabetes 57(Supplement 1):A129 (Jun. 2008).
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli et al., "Efficacy and safety of lixisenatide once daily vs. placebo in people with Type 2 diabetes insufficiently controlled on metformin (GetGoal-F1)." Diabetic Medicine 31:176-184 (published online Oct. 24, 2013).
Kendall et al., "Effets of Exenatide (Exendin-4) on Glycemic Control Over 30 Weeks in Patients With Type 2 Diabetes Treated With Metformin and a Sulfonylurea" Diabetes Care 28:1083-91 (May 2005).
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
U.S. Appl. No. 13/819,114, filed Apr. 29, 2013 to Boka et al.
U.S. Appl. No. 13/363,956, filed Feb. 1, 2012 to Silvestre et al.
U.S. Appl. No. 13/469,633, filed May 11, 2012 to Ruus et al.
U.S. Appl. No. 13/467,757, filed May 9, 2012 to Silvestre et al.
U.S. Appl. No. 13/468,422, filed May 10, 2012 to Silvestre et al.
U.S. Appl. No. 13/661,476, filed Oct. 26, 2012 to Silvestre et al.
Non-Final Rejection issued in U.S. Appl. No. 13/819,114; dated Jul. 31, 2014, pp. 1-9.
Final Rejection issued in U.S. Appl. No. 13/819,114; dated Mar. 2, 2015, pp. 1-10.
Non-Final Rejection issued in U.S. Appl. No. 13/363,956; dated Apr. 10, 2013, pp. 1-15.
Non-Final Rejection issued in U.S. Appl. No. 13/363,956; dated Nov. 20, 2013, pp. 1-10.
Final Rejection issued in U.S. Appl. No. 13/363,956; dated May 20, 2014, pp. 1-16.
Non-Final Rejection issued in U.S. Appl. No. 13/363,956; dated Feb. 11, 2015, pp. 1-18.
Non-Final Rejection issued in U.S. Application No. 13/469,633; dated Mar. 27, 2013, pp. 1-39.
Non-Final Rejection issued in U.S. Appl. No. 13/469,633; dated Aug. 19, 2013, pp. 1-25.
Final Rejection issued in U.S. Appl. No. 13/469,633; dated Dec. 4, 2013, pp. 1-17.
Non-Final Rejection issued in U.S. Appl. No. 13/469,633; dated Aug. 22, 2014, pp. 1-23.
Final Rejection issued in U.S. Appl. No. 13/469,633; dated Jan. 23, 2015, pp. 1-12.
Non-Final Rejection issued in U.S. Appl. No. 13/4467,757; dated Apr. 17, 2013, pp. 1-9.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Final Rejection issued in U.S. Appl. No. 13/468,422; dated Jan. 6, 2014, pp. 1-21.
Non-Final Rejection issued in U.S. Appl. No. 13/468,422; dated Jun. 4, 2014, pp. 1-24.
Final Rejection issued in U.S. Appl. No. 13/468,422; dated Jan. 23, 2015, pp. 1-27.
Final Rejection issued in U.S. Appl. No. 13/661,476, dated Oct. 2, 2014, pp. 1-33.
Non-Final Rejection issued in U.S. Appl. No. 13/661,476, dated Mar. 6, 2014, pp. 1-28.
Non-Final Rejection issued in U.S. Appl. No. 13/661,476, dated Dec. 4, 2013, pp. 1-11.
International Search Report by the International Searching Authority for International Application No. PCT/EP2012/055660; dated May 10, 2012, pp. 1-6.
Extended European Search Report for European Application No. 11160270.2; dated Sep. 19, 2011, pp. 1-8.
International Search Report the International Searching Authority for International Application No. PCT/EP2010/062638, dated Mar. 18, 2011, pp. 1-5.
Extended European Search Report for Application No. EP 11 15 3106, dated Jul. 6, 2011, pp. 1-12.
International Search Report from the International Searching Authority for International Application No. PCT/EP2012/051670, dated Mar. 26, 2012, pp. 1-16.
International Search Report by the International Searching Authority for International Application No. PCT/EP2012/058747, dated Jul. 8, 2012, pp. 1-6.
International Search Report by the International Searching Authority for International Application No. PCT/EP2012/058745, dated Jul. 12, 2012, pp. 1-6.
International Search Report by the International Searching Authority for International Application No. PCT/EP2012/058779, dated Aug. 28, 2012, pp. 1-5.
International Search Report by the International Searching Authority for International Application No. PCT/EP2012/071271, dated Jan. 30, 2013, pp. 1-5.
Non-Final Office Action issued in U.S. Appl. No. 13/123,835; dated Jul. 19, 2012, pp. 1-14.
Non-Final Rejection issued in U.S. Appl. No. 13/382,442; dated Feb. 5, 2015, pp. 1-31.
Final Rejection issued in U.S. Appl. No. 13/382,442; dated Jun. 13, 2014, pp. 1-29.
Non-Final Rejection issued in U.S. Appl. No. 13/382,442; dated Dec. 19, 2013, pp. 1-29.
Final Rejection issued in U.S. Appl. No. 13/382,442; dated Jul. 17, 2013, pp. 1-30.
Non-Final Rejection issued in U.S. Appl. No. 13/382,442; dated Nov. 7, 2012, pp. 1-26.
Non-Final Rejection issued in U.S. Appl. No. 13/382,772; dated Sep. 14, 2015, pp. 1-42.

(56) References Cited

OTHER PUBLICATIONS

Final Rejection issued in U.S. Appl. No. 13/382,772; dated Feb. 10, 2015, pp. 1-36.
Non-Final Rejection issued in U.S. Appl. No. 13/382,772; dated Sep. 29, 2014, pp. 1-33.
Final Rejection issued in U.S. Appl. No. 13/382,772; dated Jun. 3, 2014, pp. 1-34.
Non-Final Rejection issued in U.S. Appl. No. 13/382,772; dated Nov. 21, 2013, pp. 1-42.
Non-Final Rejection issued in U.S. Appl. No. 13/382,772; dated Apr. 10, 2013, pp. 1-48.
Final Rejection issued in U.S. Appl. No. 12/617,811; dated Jul. 31, 2015, pp. 1-15.
Non-Final Office Action from U.S. Appl. No. 12/617,805; dated Sep. 15, 2015, pp. 1-12.
Non-Final Rejection issued in U.S. Appl. No. 13/509,507; dated Dec. 8, 2015, pp. 1-14.
Final Rejection issued in U.S. Appl. No. 13/509,507; dated Jul. 23, 2015, pp. 1-11.
Non-Final Rejection issued in U.S. Appl. No. 13/509,507; dated Feb. 19, 2015, pp. 1-10.
Non-Final Rejection issued in U.S. Appl. No. 13/509,507; dated Sep. 19, 2014, pp. 1-9.
Non-Final Rejection issued in U.S. Appl. No. 13/509,507; dated Aug. 6, 2013, pp. 1-11.
Non-Final Rejection issued in U.S. Appl. No. 13/509,542; dated Aug. 11, 2015, pp. 1-30.
Final Rejection issued in U.S. Appl. No. 13/509,542, dated Jan. 28, 2015, pp. 1-26.
Non-Final Rejection issued in U.S. Appl. No. 13/509,542; dated Apr. 2, 2014, pp. 1-20.
Final Rejection issued in U.S. Appl. No. 13/509,542; dated Nov. 21, 2013, pp. 1-34.
Non-Final Rejection issued in U.S. Appl. No. 13/509,542; dated May 23, 2013, pp. 1-21.
Final Rejection issued in U.S. Appl. No. 14/172,151; dated Jul. 20, 2015, pp. 1-18.
Non-Final Rejection issued in U.S. Appl. No. 14/172,151; dated Mar. 24, 2015, pp. 1-16.
Non-Final Rejection issued in U.S. Appl. No. 14/220,562; dated Apr. 8, 2015, pp. 1-18.
Non-Final Rejection issued in U.S. Appl. No. 13/700,631; dated Apr. 22, 2013, pp. 1-27.
Non-Final Rejection issued in U.S. Appl. No. 13/700,631; dated Nov. 29, 2013, pp. 1-23.
Final Rejection issued in U.S. Appl. No. 13/700,631; dated Jun. 18, 2014, pp. 1-25.
Non-Final Rejection issued in U.S. Appl. No. 13/700,631; dated Nov. 18, 2014, pp. 1-22.
Final Rejection issued in U.S. Appl. No. 13/700,631; dated Apr. 13, 2015, pp. 1-19.
Non-Final Rejection issued in U.S. Appl. No. 13/819,114; dated Dec. 2, 2015, pp. 1-14.
Non-Final Rejection issued in U.S. Appl. No. 13/363,956; dated May 29, 2015, pp. 1-17.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Final-Rejection issued in U.S. Appl. No. 13/432,811; dated Sep. 6, 2013, pp. 1-8.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Non-Final-Rejection issued in U.S. Appl. No. 13/432,811; dated Sep. 9, 2015, pp. 1-11.
Final Rejection issued in U.S. Appl. No. 13/110,568; dated Feb. 21, 2013, pp. 1-20.
Non-Final Rejection issued in U.S. Appl. No. 13/110,568; dated Mar. 19, 2012, pp. 1-18.
Non-Final Rejection issued in U.S. Appl. No. 13/310,118, dated Mar. 25, 2015, pp. 1-15.
Non-Final Rejection issued in U.S. Appl. No. 13/310,118, dated Mar. 29, 2013, pp. 1-21.
Final Rejection issued in U.S. Appl. No. 13/310,118; dated Aug. 2, 2012, pp. 1-20.
Non-Final Rejection issued in U.S. Appl. No. 13/310,118; dated Mar. 19, 2012, pp. 1-19.
Non-Final Rejection issued in U.S. Appl. No. 13/595,590; dated Jun. 5, 2015, pp. 1-9.
Final Rejection issued in U.S. Appl. No. 13/595,590; dated Dec. 19, 2014, pp. 1-14.
Non-Final Rejection issued in U.S. Appl. No. 13/595,590; dated Sep. 5, 2014, pp. 1-10.
Final Rejection issued in U.S. Appl. No. 13/595,590; dated Apr. 2, 2014, pp. 1-7.
"Suspension" Stedman's Medical Dictionary, 20th Edition, p. 1450 (Williams & Wilkins Co., Baltimore 1961).
Tanner et al., "Rotenone, Paraquat, and Parkinson's Disease," Environmental Health Perspectives,119:866-872 (2011).
Tempero, "How I treat Pancreatic Ductal Adenocarcinoma," Current Clinical Issues, Journal of Oncology Practice, vol. 4, Issue 1, pp. 46-47 (2008).
Teramoto et al., "Exendin-4, a glucagon-like peptide-1 receptor agonist, provides neuroprotection in mice transient focal cerebral ischemia" J Cerebr Blood Flow Metab (2011) pp. 1696-1705, vol. 31, No. 8.
Tessari et al., "Insulin in Methionine and Homocysteine Kinetics in Healthy Humans: Plasma Vs. Intracellular Models", Am J. Physiol Endocrine Metab 288(6):E1270-E1276 (2005).
Tetich et al., "Neuroprotective effects of (24R)-1,24-dihydroxycholecalciferol in human neuroblastoma SH-SY5Y cell ine" J Steroid Biochemistry & Molecular Biology 89-90:365-70 (2004).
Tews et al., Abstract of Oral Presentation "Enhanced Protection Against Cytokine- and Fatty Acid-induced Apoptosis in Ins-1 Beta-Cells by Combined Treatment with Insulin Glargine and the Novel GLP-1 Receptor Agonist AVE0010" Diabetes, 56(Suppl. 1):A72-A73 (2007).
Thong et al., "Safety, efficacy and tolerability of exenatide in combination with insulin in the Association of British Clinical Diabetologists nationwide exenatide audit." Diabetes, Obesity and Metabolism 13:703-10 (2011).
Toth et al., "Neurite sprouting and synapse deterioration in the aging Caenorhabditis elegans nervous system" J Neurosci. 32(26):8778-90 (2012).
Turner et al., UK Prospective Diabetes Study (UKPDS) Group "Glycemic control with diet, sulfonylurea, mettormin, or insulin in patients with type 2 diabetes mellitus: Progressive requirement for multiple therapies (UKPDS 49)." JAMA 281(21):2005-12 (1999).
Thurow & Geisen, "Stabilisation of dissolved proteins against denaturation at hydrophobic interfaces," Diabetologia, 27(2):212-18 (Aug. 1984).
Tyler-Cross Schirch, "Effects of amino acid sequence, buffers, and ionic strength on the rate and mechanism of deamidation of asparagine residues in small peptides," J Biol Chem. 266(33):22549-56 (1991).
UK Prospective Diabetes Study (UKPDS) Group, "Effect of intensive blood-glucose control with metformin on complications in overweight patients with type 2 diabetes (UKPDS 34)" Lancet 352(9131):854-65 (Sep. 1998).
Uttenthel et al., "Molecular forms of flucagon-like peptide-1 in human pancreas and glucagonomas," J. Clin. Endocrinol. Metabol. 61(3):472-79 (1985).
Valle et al., "Cisplatin plus Gemcitabine versus Gemcitabine for Biliary Tract Cancer," N Engl J Med. 362(14)1273-81 (Apr. 2010).
Van Delden, "Pancreas-Carcinoma, CT Assessment of Resectability," Radiology Department of the Academical Medical Centre, pp. 1-12 (Apr. 2006).

(56) References Cited

OTHER PUBLICATIONS

Varadarajan et al., "Review: Alzheimer's Amyloid b-Peptide-Associated Free Radical Oxidative Stress and Neurotoxicity," Journal of Structural Biology, 130:184-208 (2000).
Venezia et al., "Apoptotic cell death and amyloid precursor protein signaling in neuroblastoma SH-SY5Y cells," Ann NY Acad Sci., 1030:339-47 (2004).
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Victoza® Annex I—Summary of product characteristics. First published 2009, pp. 1-32.
Volund et al., "In Vitro and In Vivo Potency of Insulin Analogues Designed for Clinical Use," Diab. Med. 8(9):839-47 (Nov. 1991).
Vora et al., "Incretin-based therapy in combination with basal insulin: A promising tactic for the treatment of type 2 diabetes." Diabetes & Metab. 39(1):6-15 (2013).
Wafa et al., "Use of U-500 Regular Insulin in Type 2 Diabetes", Diabetes Care, 29(9):2175-2176 (2006).
Wajchenberg, Chapter 23 "Clinical Approaches to preserve beta-cell function in Diabetes", Adv Exp Med Biol. 654:515-35 (2010).
Wan et al., "Enhancing the Activity of Insulin at the Receptor Interface: Crystal Structure and Photo-Cross-Linking of A8 Analogues," Biochemistry 43:16119-33 (2004).
Wang et al., "Real-world outcomes of US employees with type 2 diabetes mellitus treated with insulin glargine or neutral protamine Hagedorn insulin: a comparative retrospective database study." BMJ Open. 3:e002348 (2013), pp. 1-9.
Ward "Diabetic neuropathy," British Medical Bulletin, 45(1):111-26 (Jan. 1989).
Watson et al., "Insulin increases CSF Aβ42 levels in normal older adults" Neurology 60:1899-1903 (2003).
Weiss et al., "Activities of Monomeric Insulin Analogs at Position A8 Are Uncorrelated With Their Thermodynamic Stabilities", The Journal of Biological Chemistry 276(43):40018-24 (2001).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).
Weyer et al., "Long-term changes in insulin action and insulin secretion associated with gain, loss, regain and maintenance of body weight", Diabetologia, (43)1:36-46 (Jan. 2000).
White et al., "Randomized clinical trials with added rescue medication: some approaches to their analysis and Interpretation." Statistics in Medicine 20:2995-3008 (2001).
Whittingham et al., "Insulin at PH2: Structural Analysis of the Conditions Promoting Insulin Fibre Formation" J. Mol. Biol., (2002), vol. 318, pp. 479-490.
WHO Rational Use of Medicines,http://www.who.int/medicines/areas/rational_use/en/downloaded Dec. 18, 2014 10:02:48 AM (2012).
Widjaja et al., "UKPDS 20: plasma leptin, obesity, and plasma insulin in type 2 diabetic subjects." J Clin Endocrinol Metab. 82(2):654-7 (1997).
Wirths et al., "Intraneuronal APP/Aβ Trafficking and Plaque Formation in β-Amyloid Precursor Protein and Presenilin-1 Transgenic Mice" Brain Pathol. 12:275-286 (2002).
Wirths et al., "Reelin in plaques of beta-amyloid precursor protein and presenilin-1 double-transgenic mice." Neurosci Lett. 316(3):145-48 (2001).
Wirths et al., "Intraneuronal Abeta accumulation precedes plaque formation in beta-amyloid precursor protein and presenilin-1 double-transgenic mice." Neurosci Lett. 306(1-2):116-20 (2001).
Wollen, Alzheimer's disease: the pros and cons of pharmaceutical, nutritional, botanical, and stimulatory therapies, with a discussion of treatment strategies from the perspective of patients and practitioners, Altern Med. Rev., 15:223-44 (2010).
Yoon et al., "Exenatide added to insulin therapy: a retrospective review of clinical practice over two years in an academic endocrinology outpatient setting." Clinical Therapeutics 31(7):1511-23 (2009).
Yu et al., "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32(4):273-78 (2005). Abstract only.
Ziemer et al., "Clinical inertia contributes to poor diabetes control in a primary care setting" The Diabetes Educ 31(4):564-71 (2005).
Ziessman et al., "Sincalide-stimulated cholescintigraphy: a multicenter investigation to determine optimal infusion methodology and gallbladder ejection fraction normal values." J Nucl Med. 51(2):277-81 (Feb. 2010).
Zinman "The Physiologic Replacement of Insulin," New England J. Med. 321(6):363-70 (Aug. 1989).
Zinman et al., "Efficacy and safety of the human glucagon-like peptide-1 analog liraglutide in combination with metformin and thiazolidinedione in patients with type 2 diabetes (LEAD-4 Met+TZD)." Diabetes Care, 32(7):1224-30 (Jul. 2009).
Non-Final Office Action issued in U.S. Appl. No. 13/123,835; dated May 28, 2015, pp. 1-11.
Non-Final Office Action issued in U.S. Appl. No. 13/123,835; dated Dec. 22, 2014, pp. 1-11.
Final Office Action issued in U.S. Appl. No. 13/123,835; dated Feb. 12, 2013, pp. 1-13.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
Non-Final Rejection issued in U.S. Appl. No. 13/700,631; dated Dec. 17, 2015, pp. 1-18.
EMA—Science Medicines Health "TOUJEO" EPAR Summary for the Public, first published Nov. 5, 2009, pp. 1-3.
Seino et al., and The Committee of Japan Diabetes Society on the diagnostic criteria of diabetes mellitus. "Report of the committee on the classification and diagnostic criteria of diabetes mellitus." Journal of the Japan Diabetes Society. 53:450-467 (2010). In Japanese, English translation of selected passages provided.
Abbas et al., "Impairment of synaptic plasticity and memory formation in GLP-1 receptor KO mice: Interaction between type 2 diabetes and Alzheimer's disease," Behav. Brain Res. 205:265-271 (2009).
Action to Control Cardiovascular Risk in Diabetes Study Group, "Effects of intensive glucose lowering in type 2 diabetes." N Engl J. Med. 358(24):2545-59 (2008).
Aderinwale et al., "Current therapies and new strategies for the management of Alzheimer's disease," Am J Alzheimers Dis Other Demen., 25(5):414-24 (2010).
Agholme et al., "An In Vitro Model for Neuroscience: Differentiation of SH-SY5Y Cells into Cells with Morphological and Biochemical Characteristics of Mature Neurons" J Alzheimers Disease, 20:1069-82 (2010).
Aoki et al., Hydrolysis of Nonionic Surfactants, Ann. Rept. Takeda Res. Lab. 27, 172-176 (1968).
Arnolds et al., "Further improvement in postprandial glucose control with addition of exenatide or sitagliptin to combination therapy with insulin glargine and metformin—a proof-of-concept study" Diabetes Care 33(7):1509-15(2010).
Arnolds & Rave, "Basal insulin glargine vs prandial insulin lispro in type 2 diabetes," Lancet 378(9636):370-71(2008).
Auerbach et al., "Angiogenesis assays: Problems and Pitfalls," Cancer and Metastasis Reviews, 19:167-72 (2000).
Bakaysa et al., "Physicochemical basis for the rapid time-action of Lys.sup.B28 and Pro-sup-B29-insulin: Dissociation of a protein-ligand complex," Protein Science 5:2521-31 (1996).
Banks et al., "Brain Uptake of the Glucagon-Like Peptide-1 Antagonist Exendin(9-39) after Intranasal Administration" Journal of Pharmacology and Experimental Therapeutics, 309:469-75 (2004).
Barnett & Owens, "Insulin Analogues," Lancet 349(9044):47-51 (1997).

(56) References Cited

OTHER PUBLICATIONS

Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Barnett, "Dosing of Insulin Glargine in the Treatmetnt of Type 2 Diabetes," Clinical Ther. 29(6):987-99 (Jun. 2007).
Behar et al.. "Functional gallbladder and sphincter of oddi disorders." Gastroenterology 130(5):1498-1509 (2006).
Beintema & Campagne, "Molecular Evolution of Rodent Insulins," Mol. Biol. Evol. 4(1): 10-18, 1987.
Berger "Towards more physiological insulin therapy in the 1990s—A comment," Diabetes Research and Clinical Practice, 6(4): S25-31 (May 1989).
Berlie et al., "Glucagon-like peptide-1 receptor agonists as add-on therapy to basal insulin in patients with type 2 diabetes: a systematic review." Diabetes, Metabolic Syndrome and Obesity: Targets and Therapy 5:165-74 (2012).
Bertram et al., "The Genetics of Alzheimer Disease: Back to the Future," Neuron, 68:270-81 (2010).
Bhatt et al., "Chemical pathways of peptide degradation. I. Deamidation of adrenocorticotropic hormone," Pharm Res. 7(6):593-9 (1990).
Bland and Altman, "Measurement error" BMJ 312:1654 (Jun. 29, 1996).
Best, Mathmatics and Statistics pp. 1-39, 1988.
Blanchard et al., "Time sequence of maturation of dystrophic neurites associate with Aβ deposits in APP/PS1 transgenic mice" Experimental Neurology, 184:247-63 (2003).
Bolli "The pharmacokinetic basis of insulin therapy in diabetes mellitus," Diabetes Research and Clinical Practice, 6(4):S3-15 (May 1989).
Boutajangout et al., "Characterisation of cytoskeletal abnormalities in mice transgenic for wild-type human tau and familial Alzheimer's disease mutants of APP and presenilin-1" Neurobiology of Disease, 15:47-60 (2004).
Boutajangout et al., "Increased tau phosphorylation but absence of formation of neurofibrillary tangles in mice double transgenic for human tau and Alzheimer mutant (M146L) presenilin-1" 318(1):29-33 (2003).
Brange, "Design of Insulin Analogues for Meal-Related Therapy", J. Diabetes Complications 7(2):106-112 (Apr.-Jun. 1993). Abstract only.
Brange et al., "Toward Understanding Insulin Fibrillation," Journal of Pharmaceutical Sciences , 86(5):517-25 (1997).
Brange & Langkjeer, "Chemical stability of insulin 3. Influence of excipients, formulation, and pH," Acta Pharma. Nord. 4(3):149-58 (1992).
Brange et al., "Monomeric insulins and their experimental and clinical implications," Diabetes Care 13(9):923-45 (Sep. 1990).
Brange et al., "Neutral insulin solutions physically stabilized by addition of Zn2+," Diabetic Medicine 3:532-6 (Nov.-Dec. 1986).
Brange "Galenics of Insulin" 1987, p. 35-36.
Brange & Langkjaer, "Insulin Structure and Stability" Chapter 11; Pharm Biotechnol 5:315-50 (1993).
Brod et al., "Adherence patterns in patients with type 2 diabetes on basal insulin analogues: missed, mistimed and reduced doses." Curr Med Res Opin. 28(12):1933-46 (2012).
Brod et al., "Examining correlates of treatment satisfaction for injectable insulin in type 2 diabetes: lessons learned from a clinical trial comparing biphasic and basal analogues." Health Quality of Life Outcomes. 5:8 (2007), pp. 1-10.
Broderick et al., "Guidelines for the Management of Spontaneous Intracerebral Hemorrhage in Adults," Circulation 116:e391-e413 (2007).
Brown & Nichols, "Slow response to loss of glycemic control in type 2 diabetes mellitus." Am J Manag Care. 9(3):213-17 (2003).
"Buffer" Oxford Dictionary of Biochemistry and Molecular Biology, Oxford University Press, 2001, p. 83.

Burgermeister et al. "The Isolation of Insuin from the Pancreas," Insulin, Part 2, 1975, p. 715-727.
Burke et al., "Nature of the B10 amino acid residue," Int. J. Peptide Protein Res., 23(4):394-401 (Apr. 1984).
Buse et al., "Use of twice-daily exenatide in Basal insulin-treated patients with type 2 diabetes: a randomized, controlled trial." Annals of Internal Medicine 154(2):103-12 (Jan. 2011).
Byrne et al., "Inhibitory Effects of Hyperglycaemia on Fed Jejunal Motility: Potential Role of Hyperinsulinaemia," Euro. J. Clin. Invest. 28(1):72-78 (1998).
Cadario, "SITAGLIPTIN" Drug Information Perspectives, 30(4):1-6 (2010).
Campbell et al., "Insulin Glargine," Clin. Therapeutics 23(12):1938-57 (2001).
Casas et al., "Massive CA1/2 Neuronal Loss with Intraneuronal and N-Terminal Truncated Aβ 42 Accumulation in a Novel Alzheimer Transgenic Model" American Journal of Pathology 165(4):1289-1300 (2004).
Chancel, "Natixis Conference on Diabetes." Sanofi, Paris, pp. 1-23 (Nov. 8, 2011).
Chatterjee et al., "Insulin glargine and its place in the treatment of Types 1 and 2 diabetes mellitus." Expert Opin Pharmacother 7(10):1357-71 (2006).
Chen et al., Tissue-specific Expression of Unique mRNAs That Encode Proglucagon-derived Peptides or Exendin 4 in the Lizard, J. Biol. Chem. 272(7):4108-15 (1997).
Cheung et al., "Effects of all-trans-retinoic acid on human SH-SY5Y neuroblastoma as in vitro model in neurotoxicity research" NeuroToxicology, 30:127-35 (2009).
Cholangiocarcinoma, Johns Hopkins Medicine Webstite, https://gi.jhsps.org/GDL Disease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Non-Final Rejection issued in U.S. Appl. No. 13/595,590; dated Oct. 16, 2013, pp. 1-7.
Final Office Action issued in U.S. Appl. No. 13/602,913; dated Apr. 2, 2015, pp. 1-7.
Non-Final Office Action issued in U.S. Appl. No. 13/602,913; dated Dec. 2, 2014, pp. 1-12.
Final Office Action issued in U.S. Appl. No. 13/602,913; dated Jun. 20, 2014, pp. 1-27.
Non-Final Office Action issued in U.S. Appl. No. 13/602,913; dated Jan. 13, 2014, pp. 1-53.
Final Office Action issued in U.S. Appl. No. 13/602,913; dated Sep. 13, 2013, pp. 1-11.
Non-Final Office Action issued in U.S. Appl. No. 13/602,913; dated May 17, 2013, pp. 1-7.
Non-Final Rejection in U.S. Appl. No. 13/633,563; dated Jul. 1, 2013, pp. 1-56.
Final Rejection in U.S. Appl. No. 13/633,563; dated Dec. 16, 2013, pp. 1-58.
Non-Final Rejection in U.S. Appl. No. 13/633,563; dated Jun. 4, 2014, pp. 1-11.
Non-Final Rejection in U.S. Appl. No. 13/633,563; dated Dec. 1, 2014, pp. 1-9.
Final Rejection in U.S. Appl. No. 13/633,563; dated Apr. 22, 2015, pp. 1-12.
Non-Final Rejection in U.S. Appl. No. 13/633,563; dated Oct. 6, 2015, pp. 1-12.
Non-Final Rejection in U.S. Appl. No. 13/633,496; dated Apr. 29, 2013, pp. 1-53.
Final Rejection in U.S. Appl. No. 13/633,496; dated Nov. 4, 2013, pp. 1-7.
Non-Final Rejection in U.S. Appl. No. 13/633,496; dated May 22, 2014, pp. 1-11.
Final Rejection in U.S. Appl. No. 13/633,496; dated Nov. 18, 2014, pp. 1-11.
Non-Final Rejection in U.S. Appl. No. 13/633,496; dated Apr. 6, 2015, pp. 1-14.
Non-Final Rejection issued in U.S. Appl. No. 13/468,422; dated Nov. 4, 2015; pp. 1-27.

(56) References Cited

OTHER PUBLICATIONS

Non-Final Rejection issued in U.S. Appl. No. 13/661,476, dated Sep. 16, 2013, pp. 1-19.
Non-Final Rejection issued in U.S. Appl. No. 13/692,640; dated Oct. 31, 2013, pp. 1-10.
Non-Final Rejection issued in U.S. Appl. No. 13/692,640; dated May 6, 2014, pp. 1-10.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Non-Final Rejection issued in U.S. Appl. No. 14/303,895; dated Sep. 9, 2015, pp. 1-12.
Non-Final Rejection issued in U.S. Appl. No. 14/303,895; dated May 21, 2015, pp. 1-11.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/063195; dated May 6, 2010.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069485; dated Dec. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/074150; dated Nov. 20, 2012, pp. 1-4.
International Search Report by the ISA for International Application No. PCT/EP2014/062418; dated Sep. 22, 2014, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
Written Opinion of the ISA for International Application No. PCT/EP2011/058079, dated Mar. 22, 2012, pp. 1-8.
Extended European Search Report for Euorpean Application No. 98 11 0889.7; dated Oct. 14, 1998, pp. 14.
Extended European Search Report for European Application No. 10 30 5780; dated Nov. 16, 2010, pp. 1-3.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; dated Aug. 18, 2014, pp. 1-6.
English translation of Search Report for Chinese Patent Application No. 20140220537.9; dated Feb. 13, 2015, pp. 1-2.
U.S. Appl. No. 13/123,835, filed Sep. 30, 2011 to Werner et al.
U.S. Appl. No. 13/382,442, filed Mar. 21, 2012 to Schoettle.
U.S. Appl. No. 13/382,772, filed May 29, 2012 to Schoettle.
U.S. Appl. No. 13/509,507, filed Jul. 30, 2014 to Brunner-Schwarz et al.
U.S. Appl. No. 13/509,542, filed Aug. 2, 2012 to Hagendorf et al.
U.S. Appl. No. 14/172,151, filed Feb. 4, 2014 to Bley et al.
U.S. Appl. No. 14/220,562, filed Mar. 20, 2014 to Becker et al.
U.S. Appl. No. 13/432,811, filed Mar. 28, 2012 to Boka et al.
U.S. Appl. No. 13/595,590, filed Aug. 27, 2012 to Niemoeller et al.
U.S. Appl. No. 13/602,913, filed Sep. 4, 2012 to Hess et al.
U.S. Appl. No. 13/633,563, filed Oct. 2, 2012 to Stechl et al.
U.S. Appl. No. 13/633,496, filed Oct. 2, 2012 to Stechl et al.
U.S. Appl. No. 14/303,895, filed Jun. 13, 2014 to Souhami et al.
Hunter et al., "Drugs developed to treat diabetes. Liraglutide and lixisenatide, cross the blood brain barrier and enhance neurogenesis", BMC Neuroscience, (2012) vol. 13, p. 6.
"Insulin Aspart Injection." Formulated Preparations: Specific Monographs. British Pharmacopoeia 3. pp. 1-3 (2012).
Isacson et al., "The glucagon-like peptide 1 receptor agonist exendin-4 improves reference memory performance and decreases immobility in the forced swim test" Eur J Pharmacal (2009) pp. 249-255, vol. 10, No. 650.
ISPAD, International Diabetes Federation; "Global/IDF/ISPAD Guideline for Diabetes in Childhood and Adolescence," pp. 1-132 (2011).
Jackson et al., "Neutral regular insulin," Diabetes 21(4):235-45 (1972).
Jain, "Barriers to Drug Delivery in Solid Tumors," Scientific American, 271(1):58-65 (Jul. 1994).
Jang et al., "Neuroprotective Effects of Triticum aestivum L. against β-Amyloid-induced Cell Death and Memory Impairments" Phytother. Res. 24:76-84 (2010).
Jekel et al., "Use of endoproteinase Lys-C from Lysobacter enzymogenes in protein sequence analysis," Anal Biochem. 134(2):347-54 (1983).
Jendle et al., "Insulin and GLP-1 analog combinations in type 2 diabetes mellitus: a critical review." Expert Opin. Investig. Drugs 21(10):1463-74 (2012).
Jimenez et al., "Inflammatory Response in the Hippocampus of PS1M146L/APP751SL Mouse Model of Alzheimer's Disease: Age-Dependent Switch in the Microglial Phenotype from Alternative to Classic" Neurobiology of Disease, 28(45)11650-661 (2008).
Johnson et al., "When is a unit of insulin not a unit of insulin? Detemir dosing in type 2 diabetes" 2008. http://professional.diabetes.org/ContenUPosters/2008/p8-LB.pdf.
Jorgensen, K. H., et al., "Five fold increase of insulin concentration delays the absorption of subcutaneously injected human insulin suspension in pigs", Diabetes Research and Clinical Practice, 50:161-167 (2000).
Kaarsholm et al., "Engineering stability of the insulin monomer fold with application to structure-activity relationships," Biochemistry 32(40):10773-8 (1993).
Kadima "Role of Metal Ions in the T- to R-Allosteric Transition in the Insulin Hexamer," Biochem. 38(41):13443-53 (Oct. 1999).
Kaduszkiewicz et al.., "Cholinesterase inhibitors for patients with Alzheimer's disease: systematic review of randomised clinical trials." BMJ 331:321 (2005).
Kaech & Banker, "Culturing hippocampal neurons" Nat Protoc. 1(5):2406-15 (2006).
Kahn et al., "Glycemic durability of rosiglitazone, metformin, or glyburide monotherapy." N Engl J. Med. 355(23):2427-43 (2006).
Kakhi et al., "Normal values of gallbladder ejection fraction using 99 mTc-sestamibi scintigraphy after a fatty meal formula." J Gastrointestin Liver Dis. 16(2):157-61 (Jun. 2007).
Kamisawa. et al., "Pancreatographic investigation of pancreatic duct system and pancreaticobiliary malformation" J. Anal. 212(2):125-34 (2008).
Kang et al., "Subcutaneous Insulin Absorption Explained by Insulin's Physicochemical Properties—Evidence from Absorption Studies of Soluble Human Insulin and Insulin Analogues in Humans," Diabetes Care, 14(11):942-48 (Nov. 1991).
Kao et al., "The evaluation of gallbladder function by quantitative radionuclide cholescintigraphy in patients with noninsulin-dependent diabetes mellitus." Nucl. Med Commun.14(10):868-72 (1993).
Kastin et al., "Interactions of Glucagon-like peptide (GLP-1) with blood brain barrier" Journal of Molecular Neuroscience (2001) pp. 7-14, vol. 18, No. 2.
Kastin et al., "Entry of exedin-4 into brain is rapid but may be limited at high doses" International Journal of Obesity and Related

(56) References Cited

OTHER PUBLICATIONS

Metabolic Disorders: Journal of the International Association for the Study of Obesity (2003) vol. 27 No. 3, pp. 313-318.
Kemmler et al., "Studies on the Conversion of Proinsulin to Insulin," The Journal of Biological Chemistry, 246(22):6786-91 (1971).
Kielgast et al., "Treatment of type 1 diabetic patients with glucagon-like peptide-1 (GLP-1) and GLP-1R agonists." Curr Diabetes Rev. 5(4):266-75 (Nov. 2009).
Kim et al, "Exendin-4 protects dopaminergic neurons by inhibition of microglial activation and matrix metalloproteinase-3 expression in an animal model of Parkinson's disease," J. Endocrin. 202:431-439 (2009).
Kohner "Diabetic retinopathy," British Medical Bulletin, vol. 45, No. 1, 1989, pp. 148-173.
Knee et al., "A Novel Use of U-500 Insulin for Continuous Subcutaneous Insulin Infusion in Patients With Insulin Resistance: A Case Series", Endocrine Practice, 9(3):181-86 (May/Jun. 2003).
Knudsen et al., "Potent Derivatives of Glucagon-Like Peptide-1 With Pharmacokinetic Properties Suitable for Once Daily Administration", J. Med. Chem. 43(9):1664-69 (2000).
Kohn et al., "pi-shifted insulin analogs with extended in vivo time action and favorable receptor selectivity," Peptide 28:935-48 (2007).
Kolterman et al., "Synthetic Exendin-4 (Exenatide) Significantly Reduces Postprandial and Fasting Plasma Glucose in Subjects with Type 2 Diabetes," J. Clin. Endocrine. Metab. 88(7):3082-89 (2003).
Korczyn and Nussbaum, "Emerging Therapies in the Pharmacological Treatment of Parkinson's Disease," Drugs 62:775-766 (2002).
Krishnamurthy et al., Constancy and variability of gallbladder ejection fraction: impact on diagnosis and therapy. J Nucl Med. 45(11):1872-77 (Nov. 2004).
Lando, "The New 'Designer' Insulins", Clinical Diabetes, 18(4): Fall 2000 (http://journal.diabetes.org/clinicaldiabelesN18N42000/pg154.htm; accessed Oct. 22, 2013, pp. 1-13).
Langston et al., "Chronic Parkinsonism in Humans Due to a Product of Meperedine-Analog Synthesis" Science 219(4587):979-80 (1983).
Langui et al., "Subcellular Topography of Neuronal Aβ Peptide in APPxPS1 Transgenic Mice" American Journal of Pathology 165(5):1465-77 (2004).
Lantus® ANNEX I—Summary of product characteristics. Date of first authorisation: Jun. 9, 2000, pp. 1-164.
Lantus® Product Information—European Medicines Agency, first published Aug. 5, 2009, pp. 1-2.
Larsen et al., "Sequence-Assisted Peptide Synthesis (SAPS)," J. Pept. Res. 52(6):470-76 (1998).
Larsen et al., "Combination of the insulin sensitizer, pioglitazone, and the long-acting GLP-1 human analog, iraglutide, exerts potent synergistic glucose-lowering efficacy in severely diabetic ZDF rats," Diabetes, Obesity and Metabolism, 10:301-311 (2008).
Lee et al., "Ischemia-induced changes in glucagon-like peptide-1 receptor and neuroprotective effect of its agonist exendin-4, in experimental transient cerebral ischemia" J Neurosc Res (2009) pp. 1103-1113, vol. 89.
Lens, "The terminal carboxyl groups of insulin," Biochimica et Biophysica Acta 3:367-70 (1949).
Levene & Simms, "Calculation of isoelectric point," J Biol Chem. 55:801-13 (1923).
Levin et al., "Combination therapy with insulin glargine and exenatide: real-world outcomes in patients with type 2 diabetes." Current Medical Research & Opinion 28(2):1-8 (2012).
Leyer et al., "The role of the C-terminus of the insulin B-chain in modulating structural and functional properties of the hormone," Int J Pep Protein Res. 46(5):397-407 (1995).
Levine et al., "Oxidation of Methionine in Proteins: Roles in Antioxidant Defense and Cellular Regulation" IUBMB Life, 50:301-07 (Oct. 2000).
Li et al., "Chronic treatment of exendin-4 affects cell proliferation and neuroblast differentiation in the adult mouse hippocampal dentate gyrus." Neurosci Lett 19:1205-19 (2010).
Li et al., "GLP-1 Receptor Stimulation Reduces Amyloid-beta Peptide Accumulation and Cytotoxicity in Cellular and Animal Models of Alzheimer's Disease" J Alzheimers Dis (2010) pp. 1205-1219, vol. 19.
Li et al., "GLP-1 receptor stimulation preserves primary cortical and dopaminergic neurons in cellular and rodent models of stroke and Parkinsons" PNAS (2009) pp. 1285-1290, vol. 106, No. 4.
Li et al., "Enhancing the GLP-1 receptor signaling pathway leads to proliferation and neuroprotection in human neuroblastoma cells" Journal of Neurochemistry, 113:1621-631 (2010).
Li & Holscher, "Common pathological processes in Alzheimer disease and type 2 diabetes: A review" Brain Research Reviews, 56:384-402 (2007).
Lill, "Production of fast-acting insulins and delayed-release insulins—how can this problem be solved by technology?Insulin formulations," Pharmazie in unserer Zeit 30(1):56-61 (2001). (English Translation Included).
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
Lotharius et al., "Effect of Mutant a-Synuclein on Dopamine Homeostasis in a New Human Mesencephalic Cell Line," Journal of Biological Chemistry, 277:38884-94 (2002).
Lotharius et al., "Progressive Degeneration of Human Mesencephalic Neuron-Derived Cells Triggered by Dopamine-Dependent Oxidative Stress Is Dependent onthe Mixed-Lineage Kinase Pathway," Journal of Neuroscience, 25:6329-42 (2005).
Lougheed et al., "Physical Stability of Insulin Formulations," Diabetes, 32(5):424-32 (May 1983).
Lyxumia® ANNEX I—Summary of product characteristics. Date of first authorisation: Feb. 1, 2013, pp. 1-92.
Lyxumia® Product Information—European Medicines Agency, first published Mar. 14, 2013, pp. 1-2.
Lyxumia 10 micrograms solution for injection, Summary of Product Characteristics, updated Oct. 31, 2014, pp. 1-12.
Community register of medicinal products for human use, Chemical Subgroup A10BX, "Lyxumia" European Commision—Public Health, p. 1-2 (May 2, 2013).
Mancuso et al., "Clinical features and pathogenesis of Alzheimer's disease: involvement of mitochondria and mitochondrial DNA," Adv Exp Med Biol., 685:34-44 (2010).
Marbury, et al., "A Pilot Study to Examine the Feasability of Insulin Glargine in Subjects With Impaired Fasting Glucose, Impaired Glucose Tolerance or New-Onset Type 2 Diabetes", Experimental and Clinical Endocrinology & Diabetes: Official Journal, German Society of Endocrinology and German Diabetes Associate, 116(5):282-88 (May 2008).
Margolis, "Diagnosis of Huntington's Disease," Ciin. Chem. 49:1726-32 (2003).
Markussen et al., "Soluble, prolonged-acting insulin derivatives. I. Degree of protraction and crystallizability of insulins substituted in the termini of the B-chain," Prot. Eng. 1(3), 1987, pp. 205-213.
Markussen et al., "Soluble, prolonged-acting insulin derivatives. II. Degree of protraction and crystallizability of insulins substituted in positions A17, B8, B13, B27 and B30," Prot. Eng. 1(3), 1987, pp. 215-223.
Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, pp. 157-166.
Martin et al. "Neurodegenation in excitotoxicity, global cerebral ischemia, and target deprivation: A perspective on the contributions of aptopsis and necrosis," Brain Res. Bull, 46:281-309 (1998).
Martin et al., "Exendin-4 improves glycemic control, ameliorates brain and pancreatic pathologies and extends survival in a mouse model of Huntington's Disease" Diabetes (2009) pp. 318-328, vol. 58, No. 2.
Mattson "Calcium and neurodegeneration." Aging Cell 6:337-50 (2007).

(56) References Cited

OTHER PUBLICATIONS

McClean et al., "The diabetes drug Liraglutide prevents degenerative processes in a mouse model of Alzheimer's disease" Journal of Neuroscience 31(17):6587-94 (2011).
McClean et al., "Glucagon-like peptide-1 analogues enhance synaptic plasticity in the brain: A link between diabetes and Alzheimer's disease" European Journal of Pharmacology (2010) pp. 158-162, vol. 630.
Mecklenburg & Guinn, "Complications of insulin pump therapy: the effect of insulin preparation," Diabetes Care 8(4):367-70 (1985).
Meier, "GLP-1 receptor agonists for individualized treatment of type 2 diabetes mellitus." Nat. Rev. Endocrinol. 3:728-42 (2012).
Merrifield, "Solid Phase Synthesis." Science 232(4748):341-47 (1986).
Mikhail, "Is liraglutide a useful addition to diabetes therapy?" Endocr Practice 16(6):1028-37 (Nov.-Dec. 2010).
Monnier et al., The loss of postprandial glycemic control precedes stepwise deterioration of fasting with worsening diabetes. Diabetes Care. 30(2):263-69 (2007).
Moreno-Gonzalez et al., "Extracellular Amyloid-β and Cytotoxic Glial Activation Induce Significant Entorhinal Veuron Loss in Young PS1M146L/APP751SL Mice" Journal of Alzheimer's Disease 18:755-776 (2009).
Muller et al., "Insulin Signaling in the Yeast *Saccharomyces cerevisiae*. 1. Stimulation of Glucose Metabolism and Snf 1 Kinase by Human Insulin," Biochemistry, 37(24):8683-95 (Jun. 1998).
Muzaffar et al., "The Mechanism of Enhanced Insulin Amyloid Fibril Formation by NaClIs Better Explained by a Conformational Change Model," PLoS One, Nov. 21, 2011, pp. 1-11, 6(11):e27906.
Nakagawa et al., "Receptor gene expression of glucagon-like peptide-1, but not of glucose-dependent insulinotropic polypeptide, in rat nodose ganglion cells" Auton Neurosci (2004) pp. 36-43, vol. 110.
Nathan et al., "Insulinotropic Action of Glucagon like Peptide-1-(7-37) in Diabetic and Nondiabetic Subjects," Diabetes Care 15(2):270-76 (1992).
Nathan et al., "Management of hyperglycaemia in type 2 diabetes mellitus: a consensus algorithm for the initiation and adjustment of therapy. Update regarding the thiazolidinediones." Diabetologia. 51(1):8-11 (2008).
Nauck et al., "Effects of Subcutaneous Glucagon-Like Peptide 1 (GLP-1 [7-36 Amide]) in Patients with NIDDM," Diabetologia 39(12):1546-53 (1996).
Nauck et al., "Glucagon-like peptide 1 (GLP-1) as a new therapeutic approach for type 2-diabetes," Exp Clin Endocrinol. Diabetes 105(4):187-95 (1997).
Nauck et al., "Glucagon-Like Peptide 1 and its Potential in the Treatment of Non-Insulin-Dependent Diaetes Mellitus," Horm. Metab. Res. 29(9):411-16 (1997).
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
NCT01195454, NIH Clinical Trials, "Euglycemic clamp dose-response study comparing insulin glargine U300 with Lantus U100" last updated Dec. 13, 2010, pp. 1-4.
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).
NCT01255163, ClinicalTrials.gov "A Clinical Trial of Exendin-4 for the Treatment of Alzheimer's Disease" accessed Aug. 8, 2011, pp. 1-7.
NCT01174810, ClinicalTrials.gov "Exendin-4 as a Treatment for Parkinson's Disease—Pilot Study" accessed Aug. 8, 2011, pp. 1-5.

EFC6017; Clinical Trial Eudra CT No. 2007-005884-92, accessed Apr. 24, 2015, one page.
Needleman et al., "A General Method Applicable to the Search for Similarities in the Amino Acid Sequence of Two Proteins," J. Mol. Biol. 48:443-453 (1970).
Neidle, "18.2 Failure Modes in the Discovery Process" Cancer Drug Design and Discovery, Elsevier/Academic Press, pp. 427-431 (2008).
Nettleton et al. "Characterization of the Oligomeric States of Insulin in Self-Assembly and Amyloid Fibril Formation by Mass Spectrometry," Biophysical J., v79, 2000, p. 1053-1065.
NHSC—National Horizon Scanning Center, "AVE0010 (ZP10) for type 2 diabetes mellitus" University of Birmingham, England; pp. 1-6 (Dec. 2008).
Nicklas et al.., "Inhibition of NADH-Linked Oxidation in Brain Mitochondria by 1-Methyl-4-Phenyl-Pyridine, a Metabolite of the Neurotoxin, 1-Methyl-4-Phenyl-1,2,5,6-Tetrahydropyridine" Life Sciences 36:2503-508 (1985).
Nielsen et al., "Pharmacology of Exenatide (Synthetic Exendin-4): A Potential Therapeutic for Improved Glycemic Control of Type 2 Diabetes," Regul. Pept. 117(2):77-88 (2004).
Noble, et al., "Insulin Lispro: A Fast-Acting Insulin Analog," Am Fam Physician, 57(2):279-86 (1998).
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov, "Glucagon-like Peptide-1, a New Hormone of the Entero-insular Axis," Diabetologia 35(8):701-711 (1992).
Ott et al., "Diabetes in Germany" (DIG) study. "A prospective 4-year-follow-up study on the quality of treatment for type 2 diabetes in daily practice." Dtsch Med Wochenschr. 134(7):291-7 (2009). English Absract submitted.
Patel & Advance Collaborative Group, "Effects of a fixed combination of perindopril and indapamide on macrovascular and microvascular outcomes in patients with type 2 diabetes mellitus (the Advance trial): a randomised controlled trial." Lancet 370(9590):829-40 (2007).
Patel & Borchardt, "Chemical pathways of peptide degradation. II. Kinetics of deamidation of an asparaginyl residue in a model hexapeptide," Pharmaceutical Research 7(7):703-11 (1990).
Pederson et al., "Improved Glucose Tolerance in Zucker Fatty Rats by Oral Administration of the Dipeptidyl Peptidase IV Inhibitor Isoleucine Thiazolidide." Diabetes 47(8):1253-58 (1998).
Perfetti "Combining basal insulin analogs with glucagon-like peptide-1 mimetics." Diabetes Technology & Therapeutics 13(9):873-81 (2011).
Perry et al., "A novel neurotrophic property of glucagon-like peptide 1: a promoter of nerve cell growth factor mediated differentiation on PC12 cells" J Pharmacol Exp (2002) pp. 958-966, vol. 300.
Perry et al., "Protection and reversal of excitotoxic neuronal damage by glucagon-like peptide-1 and exendin-4" J Pharmacol Exp Ther (2002) pp. 881-888, vol. 302.
Perry et al., "Evidence of GLP-1-mediated neuroprotection in an animal model of pyridoxine-induced peripheral sensory neuropathy" Exp Neural (2007) pp. 293-301, vol. 203, No. 2.
Perry et al., "The glucagon-like peptides: a double-edged therapeutic sword" Trends in Pharmacological Sciences (2003) pp. 377-383, vol. 24.
Perry et al., "A new Alzheimer's disease interventive strategy: GLP-1." Current Drug Targets;5(6):565-71 (Aug. 2004).
Pillion et al., "Dodecylmaltoside-mediated Nasal and Ocular Absorption of Lyspro-Insulin: Independence of Surfactant from Multimer Dissociation," Pharmaceutical Research, 15(10): 1637-39 (Oct. 1998).
Pinget et al., "Efficacy and Safety of Lixisenatide Once Daily Versus Placebo in Patients With Type 2 Diabetes Insufficiently Controlled on Pioglitazone (GetGoal-P)" Diabetes, 61(Supp 1):A258, Poster 1010-P (Jun. 2012).
Pi-Sunyer et al., "The effects of pharmacologic agents for type 2 diabetes mellitus on body weight". Postgrad Med. 120(2):5-17 (Jul. 2008).

(56) References Cited

OTHER PUBLICATIONS

Pohl & Wank, "Molecular Cloning of the Heloderman and Exendin-4 cDNAs in the Lizard," J. Biol. Chem. 273(16):9778-84 (1998).

Porter et al., "Four weeks administration of Liraglutide improves memory and learning as well as glycemic control in mice with high fat dietary-induced obesity and insulin resistance" Diab Obes Metab (2010) pp. 891-899.

Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).

Prandini "Methods of measuring gallbladder motor functions—the need for standardization: scintigraphy." Dig Liver Dis. 35 Suppl 3:S62-6 (2003).

"Preferable." Merriam-Webster.com. Merriam-Webster, n.d. Web. Sep. 7, 2015. http://www.merriamwebster.com/dictionary/preferable).

Ramos et al., "Early neuropathology of somatostatin/NPY GABAergic cells in the hippocampus of a PS1 x APP transgenic model of Alzheimer's disease" Neurobiology of Aging, 27:1658-1672 (2006).

Rao et al., "Is the combination of sulfonylureas and metformin associated with an increased risk of cardiovascular disease or all-cause mortality? A meta-analysis of observational studies." Diabetes Care. 31(8):1672-8 (2008).

Raju et al., "Optimum Palliation of Inoperable Hilar Cholangiocarcinoma: Comparative Assessment of the Efficacy of Plastic and Self-Expanding Metal Stents," Dig Dis Sci. 56:1557-64 (published online, Jan. 11, 2011).

Raufman "Bioactive peptides from lizard venoms," Regul Pept 61(1):1-18 (1996).

Request for "Type C" Meeting letter sent by Michael Lutz addressed to Mary Parks, dated Apr. 21, 2006, pp. 1-10.

Riddle et al., Adding once-daily Lixisenatide for Type 2 Diabetes inadequately controlled by established basal insulin: a 24-week, randomized, placebo-controlled comparison (GetGoal-L). Diabetes Care 36(9):2489-96 (Sep. 2013).

Ritzel et al., "A Synthetic Glucagon-Like Peptide-1 Analog with Improved Plasma Stability," J. Endocrine. 159(1):93-102 (1998).

Rohrmann, "Differential Diagnosis of Pancreatic and Biliary Duct Diseases," Diseases of the Abdomen and Pelvis Syllabus, pp. 170-174 (1999).

Rubino et al., "Delayed initiation of subcutaneous insulin therapy after failure of oral glucose-lowering agents in patients with type 2 diabetes: a population-based analysis in the UK." Diabet Med. 24(12):1412-18 (2007).

Sanger et al., "The amide groups of insulin," Biochem J. 59(3):509-18 (1955).

Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.

Sanofi Press Release "Positive Results for Investigational Compound Lyxumia (Lixisenatide) Presented at American Diabetes Association's 71st Annual Scientific Sessions," (Jun. 24, 2011), pp. 1-5.

Sanofi Press Release entitled "FDA Accepts Sanofi's New Drug Application for Basal Insulin Toujeo®," dated Jul. 8, 2014, pp. 1-2.

Sanofi Press Release entitled "Sanofi Receives FDA Approval of Once-Daily Basal Insulin Toujeoe," dated Feb. 26, 2015, pp. 1-4.

Zealand Pharma Press Release entitled "Sanofi-Aventis finalize phase Iia clinical study with GLP-1 agonist for type 2 diabetes licensed from Zealand Pharma" dated Mar. 3, 2005, one page.

Schapira, "Causes of neuronal death in Parkinson's disease." Adv Neurol 86:155-162 (2001).

Schellenberger et al., "Attempts for Quantifying the S' Subsite Specificity of Serine Proteases," Selected Papers Presented at the 2nd International Meeting on the Molecular and Cellular Regulation of Enzyme Activity, Advances in The Biosciences, Peptides and Proteases: Recent Advances 65:159-66 (1987).

Schellenberger et al., "Protease-Catalyzed Kinetically Controlled Peptide Synthesis," Angewante Chemie, International Edition 30(11):1437-49 (1991).

Schindowski et al., "Impact of Aging: Sporadic, and Genetic Risk Factors on Vulnerability to Apoptosis in Alzheimer's Disease" NeuroMolecular Medicine, 4:161-177 (2003).

Schmitz et al., "Hippocampal Neuron Loss Exceeds Amyloid Plaque Load in a Transgenic Mouse Model of Alzheimer's Disease" American Journal of Pathology, 164(4):1495-1502 (2004).

Schwartz et al., "A superactive insulin: [B10-Aspartic acid]insulin(human)," Proc. Natl. Acad. Sci. USA, 84(18):6408-11 (Sep. 1987).

Schubert-Zsilavecz et al., "Better blood sugar control in diabetics. Insulin glargin—a long acting insulin analogue," Pharmazie in Unserer Zeit 30(2):125-30 (2001). With English translation.

Secnik Boye et al., "Patient-reported outcomes in a trial of exenatide and insulin glargine for the treatment of type 2 diabetes," Health and Quality of Life Outcomes, vol. 4, No. 80, pp. 1-8 (Oct. 2006).

Seino et al., "Randomized, double-blind, placebo-controlled trial of the once-daily GLP-1 receptor agonist lixisenatide in Asian patients with type 2 diabetes insufficiently controlled on basal insulin with or without a sulfonylurea (GetGoal-L-Asia)." Diabetes, Obesity and Metabolism 14(10):910-17 (2012).

Sherer et al., "Subcutaneous Rotenone Exposure Causes Highly Selective Dopaminergic Degeneration and a-Synuclein Aggregation," Experimental Neurology, 179:9-16 (2003).

Sluzky et al., "Kinetics of Insulin Aggregation in Aqueous Solutions Upon Agitation in the Presence of Hydrophobic Surfaces," Proc. Natl. Acad. Sci. USA. 88(21):9377-81 (Nov. 1991).

Sporn & Suh, "Chemoprevention of cancer" Carcinogenesis, 21(3):535-530 (2000).

Starkova, ed., "Clinical Endocrinology", Guide for physicians, Moscow, "Medicine", 1991, p. 192-262.

Stolk et al., "Insulin and cognitive function in an elderly population. The Rotterdam Study." Diabetes Care, 20:792-95 (1997).

Sundby "Separation and Characterization of Acid-Induced Insulin Transformation Products by Paper Electrophoresis in 7 M Urea," J. Biol. Chem. 237(11):3406-11 (Nov. 1962).

"Suspension" Taber's Cyclopedic Medical Dictionary, 19th Edition, p. 2097 (F.A. Davis Co., Philadelphia 2001).

English translation of Search Report for Chinese Patent Application No. 201280053404.6; dated Feb. 10, 2015, pp. 1-3.

Search Report of the Intellectual Property Corporation of Malaysia for Malaysian Patent Application No. PI 2011006204; dated Sep. 15, 2015, pp. 1-3.

Search Report of the Indecopi for Patent Application in Peru No. 000643-2012/DIN, dated Jul. 23, 2015, pp. 1-2.

Search Report of the Intellectual Property Office of Singapore for Patent Application No. 10201500871T, dated Nov. 2, 2015, pp. 1-3.

Berlinsulin® H prescribing information, Apr. 2012, pp. 1-4.

Humalog® prescribing information, Apr. 2012, pp. 1-6.

Insuman® Comb25 prescribing information, Feb. 2011, pp. 1-4.

Insuman® Infusat prescribing information, Feb. 2011, pp. 1-4.

Lantus® prescribing information, May 2012, pp. 1-6.

Levemir® prescribing information, Dec. 2011, pp. 1-6.

Novolog® product information, Oct. 2009, pp. 1-4.

NovoMix® prescribing information, Feb. 2011, pp. 1-5.

NovoRapid® prescribing infonnation, Jul. 2012, pp. 1-5.

Feinglos et al., "Effects of liraglutide (NN2211), a long-acting GLP-1 analogue, on glycaemic control and bodyweight in subjects with type 2 diabetes." Diabetic Medicine, 22(8):1016-23 (Jul. 2005).

Fieller, Symposium on Interval Estimation; "Some Problems with Interval Estimation" Journal of the Royal Statistical Society 16(2):175-85 (1954).

Fox et al., Protein Science 10: 622-30 (2001).

Fransson et al., "Oxidation of Human Insulin-Like Growth Factor I in Formulation Studies: Kinetics of Methionine Oxidation in Aqueous Solution and in Solid State" Pharmaceutical Research 13(8):1252-57 (Aug. 1996).

Galloway & Root, "New forms of insulin," Diabetes 21 (2 Suppl):637-48 (1972).

(56) References Cited

OTHER PUBLICATIONS

Gandhi & Wood, "Molecular pathogenesis of Parkinson's disease." Hum Mol Genet 14:2749-55 (2005).
Garg, R., et al., "U-500 insulin: why, when and how to use in clinical practice", Diabetes/Metabolism Research and Reviews, 23:265-268 (2007).
Garriques et al., "The Effect of Mutations on the Structure of Insulin Fibrils Studied by Fourier Transform Infrared (FTIR) Spectroscopy and Electron Microscopy," Journal of Pharmaceutical Sciences, 91(12):2473-80 (2002).
Gault et al. "GLP-1 agonists facilitate hippocampal L TP and reverse the impairment oiL TP induced by beta-amyloid." Eur J Pharmacal; 587(1-3):112-7 (Jun. 10, 2008; published online Mar. 29, 2008).
Geiger, Chem. Zeitung, 100(3), p. 54-56. (Jan. 1976).
Gengler et al., "Vai(8)GLP-1 rescues synaptic plasticity and reduces dense core plaques in APP/PS1 mice" Neurobiol Aging (2012) pp. 265-276, vol. 33.
Giugliano et al., "Treatment regimens with insulin analogues and haemoglobin A1c target of <7% in type 2 diabetes: A systematic review." Diabetes Research and Clinical Practice 92(1):1-10 (2010).
Goke et al., "Distribution of GLP-1 Binding Sites in the Rat Brain: Evidence that Exendin-4 is a Ligand of Brain GLP-1 Binding Sites," Eur. J. Neurosci. 7(11):2294-2300 (1995).
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Gough, K et al.; Assessment of Dose Proportionality: Report from the Statisticians in the Pharmaceutical Industry/Pharmacokinetics UK Joint Working Party; Drug Information Journal, vol. 29, 1995, pp. 1039-1048.
Goykhman et al., "Insulin Glargine: a review 8 years after its introduction." Expert Opin. Pharmacother. 10(4):705-18 (2009).
Greig et al., "Once Daily Injection of Exendin-4 to Diabetic Mice Achieves Long-Term Beneficial Effects on Blood Glucose Concentrations." Diabetologia 42(1):45-50 (1999).
Gura, "Systems for Identifying New Drugs are Often Faulty," Science, 278(5340):1041-042 (1997).
Gutniak et al., "Antidiabetogenic Effect of Glucagon-Like Peptide-1 (7-36) Amide in Normal Subjects and Patients with Diabetes Mellitus," N. Engl. J. Med. 326:1316-1322 (1992).
Hamilton et al., "Novel GLP-1 mimetics developed to treat type 2 diabetes promote progenitor cell proliferation in the brain" J Neurosci Res (2011) pp. 481-489, vol. 89.
Hamilton et al., "Receptors for the incretin glucagon-like peptide-1 are expressed on neurons in the central nervous system" Neuroreport(2009) vol. 20 No. 13, pp. 1161-1166.
Hanefeld & Temelkova-Kurktschiev, "The postprandial state and the risk of atherosclerosis." Diabet Med. 14 Suppl 3:S6-11 (1997).
Hanefeld M. Normnahe postprandiale Hyperglykamie-eine essenzielle Komponente guter Diabeteskontrolle und Pravention kardiovaskularer Erkrankungen (Near-normal postprandial hyperglycemia—an essential component of good diabetes control and prevention of cardiovascular diseases). Paul Langerhans lecture 2007. Diabetologie und Stoffwechsel 2007; 2:362-369. in German with English abstract.
Harris "Clinical inertia in patients with T2DM requiring insulin in family practice." Can Fam Physician.56(12):e418-e424 (2010).
Harkavyi et al., "Glucagon-like peptide I receptor stimulation reverses key deficits in distinct rodent models of Parkinson's disease" J Neuroinftamm (2008) pp. 1-9, vol. 5, No. 19.
Hartmann et al., "Biological Activity of des-(B26-B30)-Insulinamide and Related Analogues in Rat Hepatocyte Cultures," Diabetologia 32(7):416-20 (1989).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).

Hellstrom et al., "T1388 GTP-010 as a Therapetuic Tool in IBS Pain Relief: Prospective, Randomized, Palebo-Controlled Study of a GLP-1 Analog", Gastroenterology, 134(4):A-544; Absract T1388 (Apr. 2008).
Higgins et al., "Oxidative Stress: Emerging Mitochondrial and Cellular Themes and Variations in Neuronal Injury", Journal of Alzheimer's Disease, 20:S453-S473 (2010).
Himeno et al., "Beneficial effects of exendin-4 on experimental polyneuropathy in diabetic mice" Diabetes (2011) pp. 2397-2406, vol. 60.
Hinds et al., "Synthesis and characterization of poly(ethylene glycol)-insulin conjugates." Bioconjugate Chem. 11(2)195-201 (Mar.-Apr. 2000).
HOE 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671079.
Holscher "Development of Beta-Amyloid-induced neurodegeneration in Alzheimer's disease and novel neuroprotective strategies," Reviews in Neuroscience, 16:181-212 (2005).
Holscher et al., "New roles for insulin-like hormones in neuronal signaling and protection: new hopes for novel treatments of Alzheimer's disease?" Neuro. Aging 31:1495-1502 (2008).
Holscher "The role of GLP-1 in neuronal activity and neurodegeneration" Vitamins and hormones 84:331-54 (2010).
Holscher "Incretin Analogues that have been Developed to Treat Type 2 Diabetes Hold Promise as a Novel Treatment Strategy for Alzheimer's Disease" Recent Patents on Cns Drug Discovery(2010) vol. 5 No. 2, pp. 109-117.
Holscher "Possible Causes of Alzheimer's Disease: Amyloid Fragments, Free Radical, and Calcium Homeostasis" Neurobiology of Disease 5:129-41 (1998).
Holst, "Glucagon-like Peptide-1, A Gastrointestinal Hormone with a Pharmaceutical Potential," Current Medicinal Chemistry 6:1005-17 (1999).
Holst & Vilsboll. "Combining GLP-1 receptor agonists with insulin: therapeutic rationales and clinical findings." Diabetes, Obesity and Metabolism 15(1):3-14 (2013).
Home et al., "Insulin treatment: a decade of change," British Medical Bulletin, 1989, vol. 45, No. 1, pp. 92-110.
Holman et al., "10-Year Follow-up of Intensive Glucose Control in Type 2 Diabetes." N Engl J. Med. 359(15):1577-89 (2008).
Cochran et al., "The Use of U-500 in Patients with Extreme Insulin Resistance" Diabetes Care, 28(5):1240-44.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino et al., "Therapy with insulin glargine (Lantus) in toddlers, children and adolescents with type 1 diabetes," Diabetes Research and Clinical Practice (2005), vol. 70, pp. 1-7.
Correa, "Pautas para el examen de patentes farmaceuticas. Una perspectiva desde la Salud Publica. Documento de Trabajo" Universidad de Buenos Aires, Mar. 2008, see pp. 19-20, pp. 1-66.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Croom et al., "Liraglutide A Review of its Use in Type 2 Diabetes Mellitus," Drugs, 69(14):1985-2004 (2009).
Cvetkovic et al., "Exenatide A Review of Its Use in Patients with Type 2 Diabetes Mellitus (as an Adjunct to Metformin and/or a Sulfonylurea)," Drugs, 67(6):935-54 (2007).
Czech et al., "Proteolytical processing of mutated human amyloid precursor protein in transgenic mice" Molecular Brain Research 47:108-116 (1997).
D'Alessio et al., "Glucagon-like Peptide 1 Enhances Glucose Tolerance Both by Stimulation of Insulin Release and by Increasing Insulin-independent Glucose Disposal," J. Clin. Invest. 93(5):2263-66 (1994).
Database, ADISCTI, "A randomized, 4-sequence, cross-over, double bind, dose response study of 0.4, 0.6 and 0.09 U/kg insluin

(56) References Cited

OTHER PUBLICATIONS glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
Deacon et al., "Dipeptidyl Peptidase IV Inhibition Potentiates the Insulinotropic Effect of Glucagon-Like Peptide 1 in the Anesthetized Pig," Diabetes 47(5):764-69 (1998).
Deacon et al., "Dipeptidyl Peptidase IV Resistant Analogues of Glucagon-Like Peptide-1 Which Have Extended Metabolic Stability and Improved Biological Activity," Diabetologia 41(3):271-78 (1998).
de Arriba et al., "Carbonyl stress and NMDA receptor activation contribute to methylglyoxal neurotoxicity" Free Radical Biology & Medicine, 40:779-90 (2006).
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
DeFronzo "Pharmacologic Therapy for Type 2 Diabetes Mellitus." Ann Int Med. 131:281-303 (1999).
Delatour et al., "Alzheimer pathology disorganizes cortico-cortical circuitry: direct evidence from a transgenic animal model" Neurobiology of Disease, 16:41-47 (2004).
De Le Pena, "Pharmacokinetics and Pharmadynamics of High-Dose Human Regular U-500 Insulin Versus Human Regular U-1 00 Insulin in Healthy Obese Subjects" Diabetes Care, 34(12):2496-501 (2011).
De Rosa, et al. "Intranasal administration of nerve growth factor (NGF) rescues recognition memory deficits in a D11 anti-NGF transgenic mice." Proc Natl Acad. Sci., 102:3811-16 (2005).
DeWitt, "Case Study: Treating New On-Set Catabolic Type 2 Diabetes With Glargine and Lispro", Clinical Diabetes vol. 24, No. 4, pp. 180-181,(Oct. 2006).
deVries et al., "Sequential intensification of mettormin treatment in type 2 diabetes with liraglutide followed by randomized addition of basal insulin prompted by A1C targets." Diabetes Care 35:1446-54 (2012).
Diabetes Prevention Program Research Group. "Reduction in the incidence of type 2 diabetes with lifestyle intervention or metformin." N Engl J. Med. 346(6):393-403 (2002).
Dixon et al., "Regeneration of Insulin Activity From the Separated and Inactive A and B Chains," Nature, vol. 188, No. 4752 (1960), pp. 721-724.
Donelli, "Plastic Biliary Stent Occlusion: Factors Involved and Possible Preventive Approaches," Clinical Medicine & Research 5(1):53-60 (Mar. 2007).7.
Doyle et al., "Mechanisms of action of glucagon-like peptide 1 in the pancreas" Pharmacal Ther. (Mar. 2007) pp. 546-593, vol. 113, No. 3.
Drury et al., "Diabetic nephropathy," British Medical Bulletin, vol. 45, No. 1, 1989, pp. 127-147.
Drucker, "The Biology of Incretin Hormones," Cell Metab. 3(3):153-65 (2006).
Drucker, "Glucagon-Like Peptides," Diabetes 47(2):159-69 (1998).
Drucker, "Mini review: The Glucagon-Like Peptides," Endocrinology 142(2):521-27 (2001).
Drucker et al., "The incretin system: glucagon-like peptide-1 receptor agonists and dipeptidyl peptidase-4 inhibitors in type 2 diabetes." Lancet; 368(9548):1696-705 (Nov. 11, 2006).
DrugBank, "Insulin glargine," available online at http://www.drugbank.ca/drugs/DB00047, 16 pages (accessed online Sep. 25, 2014).
Dubois et al., "Revising the definition of Alzheimer's disease: a new lexicon." Lancet Neural. 9: 1118-27 (2010).
During et al., "Glucagon-like peptide-1 receptor is involved in learning and neuroprotection" Nat Med (2003) pp. 1173-1179, vol. 9.
Dunn et al., "Insulin Glargine: An Updated Review of its Use in the Management of Diabetes Mellitus" Drugs 63 (16):1743-1778 (2003).
Eckert et al., "Alzheimer's Disease-like Alterations in Peripheral Cells from Presenilin-1 Transgenic Mice" Neurobiology of Disease 8, 331-342 (2001).
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
EMA Press Release, "European Medicines Agency recommends suspension of Avandia, Avandamet and Avaglim" pp. 1-2 (Sep. 23, 2010).
European Medicines Agency—Science Medicines Health, "Guideline on clinical investigation of medicinal products in the treatment of diabetes mellitus" Committee for Medicinal Products for Human Use, Jan. 20, 2010, pp. 1-19.
*Ex Parte Herrmann,* Appeal No. 2009-001777 U.S. Appl. No. 10/616,457 (B. PAI. Nov. 13, 2009).
Fabunmi et al., "Patient characteristics, drug adherence patterns, and hypoglycemia costs for patients with type 2 diabetes mellitus newly initiated on exenatide or insulin glargine." Curr Med Res Opin. 25(3):777-86 (2009).
Faivre et al., "Effect of GIP Analogues in Neuronal Signalling, Cell Proliferation and Learning and Memory." Regulatory Peptides; 164(1):40-41 (Sep. 9, 2010, published online Aug. 20, 2010).
FDA Frequently Asked Questions about Combination Products;accessed from www.fda.gov/CombinationProducts/AboutCombinationProducts/usm101496.1/htm, 2009 downloaded Jul. 13, 2012, pp. 1-18.
FDA label of Apidra®, May 2014, pp. 1-35.
FDA label of Humalog®, Mar. 2013, pp. 1-27.
FDA label of Lantus®, Oct. 2013, pp. 1-44.
Actrapid® summary of product characteristics, Apr. 2011, pp. 1-11.
Actrapid® prescribing information, Apr. 2011, pp. 1-4.
Apidra® prescribing information, Apr. 2012, pp. 1-6.
Berlinsuline® H summary of product characteristics, Apr. 2012, pp. 1-11.
Final-Rejection issued in U.S. Appl. No. 13/432,811; dated Feb. 10, 2016, pp. 1-9.
Final Rejection issued in U.S. Appl. No. 13/509,542, dated Feb. 10, 2016, pp. 1-40.
http://diabetes.emedtv.com/lantus/generic-lantus.html; one page, last accessed Dec. 23, 2015.
American Diabetes Association, "Type 2 diabetes in children and adolescents." Diabetes Care 23(3):381-89 (Mar. 2000).
Ahualli "The Double Duct Sign" Radiology 244(1):314-5 (Jul. 2007).
Aquiliante, "Sulfonylurea pharmacogenomics in type 2 diabetes: the influence of drug target and diabetes risk polymorphisms" Expert Rev Cardiovasc Ther. 8(3):359-72 (Mar. 2010).
Canadian Diabetes Association. Clinical Practice Guidelines Expert Committee. Canadian Diabetes Association 2008. Clinical Practice Guidelines for the Prevention and Management of Diabetes in Canada. Canadian Journal of Diabetes S162-S167 (2008).
Centers for Disease Control and Prevention. National diabetes fact sheet: general information and national estimates on diabetes in the United States, 2003. Rev ed. Atlanta, GA: U.S. Department of Health and Human Services, Centers for Disease Control and Prevention, pp. 1-8, 2004.
Chi et al., "Excipients and their Effects on the Quality of Biologics" pp. 1-9, (May 2012).
Definition of indication, Merriam-Webster online, accessed Oct. 22, 2015, 2 pages.
Definition of Phase, Clinical Trials.gov NIH, accessed Mar. 16, 2016, one page.
Druet et al., "Characterization of insulin secretion and resistance in type 2 diabetes of adolescents." J Clin Endocrinol Metab 91(2):401-404 (Feb. 2006; epub Nov. 15, 2005).

(56) References Cited

OTHER PUBLICATIONS

European Medicines Agency, "Toujeo (previously Optisulin) insulin glargine," <http://www.ema.europa.eu/ema/index.jsp?curl=pages/medicines/human/medicines/000309/human_med_000955.jsp&mid=WC0b01ac058001d124>, last updated Jan. 25, 2016, visited Feb. 3, 2016, pp. 1-6—screenshot of "About" tab of webpage and printouts of "About" tab of webpage with listed items collapsed and expanded.

Gygi et al., "Quantitative analysis of complex protein mixtures using isotope-coded affinity tags." Nat Biotechnol. 17(10):994-99 (Oct. 1999).

IDF Clinical Guidelines Task Force. Global guideline for Type 2 diabetes. Brussels: International Diabetes Federation, pp. 1-82 (Aug. 2005).

Johnson et al., "Diabetes, Insulin Resistance, and Metabolic Syndrome in Horses" Journal of Diabetes Science and Technology, 6(3):534-40 (May 2012).

Jones et al., "Effect of metformin in pediatric patients with type 2 diabetes: a randomized controlled trial." Diabetes Care 25(1):89-94 (Jan. 2002).

Kim et al., "Retinopathy in Monkeys with Spontaneous Type 2 Diabetes" Investigative Opth & Visual Science, 45(12):4543-53 (Dec. 2004).

Laursen et al., "Enhanced monitoring of biopharmaceutical product purity using liquid chromatography-mass spectrometry." 1218(28):4340-48 (Jul. 2011; Epub May 2011).

Leib et al., "Direct quantitation of peptide mixtures without standards using clusters formed by electrospray ionization mass spectrometry." Anal Chem. 81(10):3965-72 (May 2009).

Nathan et al., "Medical Management of Hyperglycemia in Type 2 Diabetes: A Consensus Algorithm for the Initiation and Adjustment of Therapy" Diabetes Care 32(1):193-203 (Jan. 2009).

NCT00866658 ClinicalTrials.gov, "GLP-1 agonist AVE0010 in patients with type 2 diabetes for glycemic control and safety evaluation, on top of basil insulin +/− sulfonylurea" p. 1-3, accessed Mar. 16, 2016 (updated Jan. 19, 2010).

NCT01169779, Clinical Trials.gov, "Efficacy and Safety of Lixisenatide in Patients with Type 2 diabetes mellitus insufficiently controlled by mefformin," pp. 1-3, accessed Mar. 16, 2016 (updated Mar. 28, 2011).

NCT00713830, Clinical Trials.gov "GLP-1 Agonist in Patients with Type 2 Diabetes for Glycemic Control and Safety Evaluation, on Top of Sulfonylurea" pp. 1-3, accessed Mar. 16, 2016 (updated Jul. 13, 2008).

Nice' National Institute for Health and Care Excellence, "Evidence summary: new medicine, ESNM26: Type 2 diabetes: lixisenatide; Key points from the evidence" pp. 1-26 (Sep. 24, 2013).

NIH, National Institute of Diabetes and Digestive and Kidney Disease, "Hypoglycimia" pp. 1-8, accessed Mar. 16, 2016.

Nilsson et al., "Effects of GI vs content of cereal fibre of the evening meal on glucose tolerance at a subsequent standardized breakfast." Eur. J Clin Nutr. 62:712-20 (2008; epub May 23, 2007).

Olansky "Do incretin-based therapies cause acute pancreatitis?" J Diabetes Technol. 4(1):228-29 (Jan. 2010).

Pinhas-Hamiel & Zeitler, "Clinical presentation and treatment of type 2 diabetes in children." Pediatric Diabetes 8(9):16-27 (Dec. 2007).

Sanofi-aventis Press Release, "A promising R&D portfolio, well positioned to deliver future growth" (dated Sep. 17, 2007) pp. 1-11.

Schwartz et al., "New Equations to Estimate GFR in Children with CKD." J Am Soc Nephrol. 20(3):629-37 (Mar. 2009; epub Jan. 21, 2009).

Smolka et al., "Optimization of the isotope-coded affinity tag-labeling procedure for quantitative proteome analysis." Anal Biochem. 297(1):25-31 (Oct. 2001). Abstract only submitted.

Srinivasan & Ramarao, "Animal models in type 2 diabetes research: An overview." Indian J Med Res. 125:451-472 (Mar. 2007).

Tanner et al., "Standards from birth to maturity for height, weight, height velocity, and weight velocity: British children, Part II" Arch Dis Child. 41(220):613-35 (1966).

World Health Organization, "Definition, Diagnosis and Classification of Diabetes Mellitus and its Complications. Part 1: Diagnosis and Classification of Diabetes Mellitus." WHO/NCD/NCS/99.2. Geneva; pp. 1-66, (1999).

Xie et al., "Characterization of protein impurities and site-specific modifications using peptide mapping with liquid chromatography and data independent acquisition mass spectrometry." Anal Chem. 81(14):5699-708 (Jul. 2009).

Non-Final Rejection issued in U.S. Appl. No. 13/382,442; dated Mar. 31, 2016, pp. 1-29.

Final Rejection issued in U.S. Appl. No. 13/382,442; dated Aug. 11, 2015, pp. 1-35.

Final Rejection issued in U.S. Appl. No. 13/382,772; dated Feb. 24, 2016, pp. 1-36.

Final Rejection issued in U.S. Appl. No. 14/303,895; dated Apr. 27, 2015, pp. 1-10.

International Search Report by the ISA for International Application No. PCT/EP2015/079285; dated Mar. 9, 2016, pp. 1-7.

Extended European Search Report for European Application No. 15 15 90643; dated Oct. 19, 2015, pp. 1-4.

English Translation of TIPO Search Report for ROC Patent Application No. 101130936, dated Dec. 1, 2015, one page.

English translation of the TIPO Search Report for ROC Patent Application No. 104116749, dated Feb. 22, 2016, one page.

English translation of the TIPO Search Report for ROC Patent Application No. 101131466 dated Mar. 2, 2016, one page.

Kendall et al., "Clinical Application of Incretin-Based Therapy: Therapeutic Potential, Patient Selection and Clinical Use." European Journal of Internal Medicine. 20(Suppl 2):S329-39 (Jul. 2009).

Abraira et al., "Glycaemic separation and risk factor control in the Veterans Affairs Diabetes Trial: an interim report" Diabetes Obes Metab 11(2):150-56 (2009; Epub Jul. 29, 2008).

Aguilar, "Heart failure and diabetes: Time to pay attention" American Heart Journal, 162(5):795-97 (Nov. 2011).

American Diabetes Association, "Diagnosis and Classification of Diabetes Mellitus", Diabetes Care, 37 (Supplement 1):581-S90 (Jan. 2014).

American Diabetes Association, "Standards of Medical Care in Diabetes—2011," Diabetes Care, Jan. 2011, vol. 34 (Suppl 1), pp. S11-S61.

Ampudia-Blasco et al., "Basal Plus Basal-Bolus approach in type 2 diabetes" Diabetes Technol Ther. 13 Suppl1: S75-83 (Jun. 2011).

Atkinson et al., "validation of a general measure of treatment satisfaction, the Treatment Satisfaction Questionnaire for Medication (TSQM), using a national panel study of chronic disease" Health Qual Life Outcomes, 2:12, pp. 1-13 Feb. 2004).

Beckman et al., "Diabetes and atherosclerosis: epidemiology, pathophysiology, and management" JAMA 287 (19):2570-81 (May 2002).

Bell et al., "Sequence of the Human Insulin Gene, "Journal of Nature, 1980, vol. 284 (5751), pp. 26-32.

Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).

Brazier et al., "Testing the validity of the Euroqol and comparing it with the SF-36 health survey questionnaire," Qual Life Res 2(3):169-80 (Jun. 1993).

Byetta® Product information, EMA pp. 1-2, accessed Jun. 10, 2016.

Byetta® Summary of product characteristics, ANNEX I, pp. 1-71, (2011).

Canadian Cardiovascular Society Grading of Angina Pectoris, From http://www.sscts.org/pages/Classificationanginaccs.aspx. Accessed May 27, 2016, one page.

Cannon et al., "Intensive versus Moderate Lipid Lowering with Statins after Acute Coronary Syndromes." New England Journal Medicine, Apr. 2004; Epub 2004 Mar. 8, 2004, vol. 350 (15), pp. 1495-1504.

Classification of Functional Capacity and Objective Assessment, My.AmericanHeart, 1994 last accessed Oct. 23, 2015, pp. 1-2.

(56) References Cited

OTHER PUBLICATIONS

Clinical Trials Archive for Trial No. NCT00688701 updated Sep. 30, 2012. Accessed at: https://clinicaltrials.gov/ archive/NCT00688701/2012.09.30/changes Accessed on Jun. 2, 2016, pp. 1-5 submitted.
Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.
Yki-Järvinen, "Combination Therapies with insulin in type 2 diabetes." Diabetes Care 24(4):758-67 (Apr. 2001).
Yki-Järvinen et al., "Comparison of Bedtime insulin regimes in patients with type 2 diabetes mellitus." Annals of Internal Medicine 130(5):389-96 (Mar. 1999).
Zinman et al., "The Effect of Adding Exenatide to a Thiazolidinedione in Suboptimally Controlled Type 2 Diabetes" Annals of Internal Medicine, 146(7):477-85 (Apr. 2007).
D'Alessio et al., "The role of dysregulated glucagon secretion in type 2 diabetes" Diabetes, Obesity and Metabolism, 13(Supppl. 1):126-132 (Oct. 2011).
Das et al., "The British Cardiac Society Working Group Definition of Myocardial Infarction: Implications for Practice," Heart, 2005, vol. 92 (1), pp. 21-26, Jan. 2006; Epub Apr. 14, 2005.
De Lemos et al., "Early intensive vs. a delayed conservative simvastatin strategy in patients with acute coronary Syndromes: phase Z of the A to Z trial." JAMA 292(11):1307-16 (Sep. 2004; Epub Aug. 30, 2004).
Definition of "Combination", Concise Oxford English Dictionary, edited by A. Stevenson and M. Waite, Oxford University press, 12th Edition, Aug. 2011, 4 pages submitted, see p. 285.
Del Prato & Tiengo, The importance of first-phase insulin secretion: implications for the therapy of type 2 diabetes mellitus. Diabetes Metab Res. Rev. 17(3):164-74 (May-Jun. 2001).
Del Prato et al., "Global Partnership for Effective Diabetes Management Tailoring treatment to the individual in type 2 diabetes practical guidance from the Global partnership for effective diabetes management" Int J Clin Pract 64 (3):295-304 (Feb. 2010).
DeWitt & Hirsch, "Outpatient insulin therapy in type 1 and type 2 diabetes mellitus: scientific review." JAMA 289 17):2254-64 (May 2003).
Diabetes Control and Complications Trial Epidemiology of Diabetes Interventions and Complications Research Group, "Intensive Diabetes Treatment and Cardiovascular Disease in Patients with Type 1 Diabetes," New England Journal Medicine, 353(25):2643-59 (Dec. 2005).
Diabetes Control and Complications Trial, "Intensive diabetes therapy and carotid intima-media thickness in type 1 diabetes," New England Journal Medicine, 348(23):2294-2303 (Jun. 2003).
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
EMA—European Medicines Agency, "Note for guidance on non-clinical safety studies for the conduct of human clinical Trials and marketing authorization for pharmaceuticals," Jul. 2008, pp. 1-22.
Encyclopedia of Drugs, "METFORMIN" Moscow, Drug Register of 2001, p. 549, English translation provided pp. 1-2.
European Medicines Agency, Committee for Medicinal Products for Human Use (CHMP), "Assessment Report—Lyxumia", Nov. 28, 2012, pp. 1-81.

European Public Assessment Report (EPAR) Optisulin, EPAR Summary for the Public. Feb. 2009, pp. 1-3.
EuroQol Group, "EuroQol—a new facility for the measurement of health-related quality of life." Health policy (Amsterdam, Netherlands) 16(3)199-208 (Dec. 1990).
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Faichney et al., "Metformin in Type 1 diabetes: Is This a Good or Bad Idea?" Diabetes Care, 26(5):1655 (2003).
FDA, Food and Drug Administration, CFR—Code of Federal Regulations Title 21, Chapter 1, Subchapter D, Part 312.21, "Phases of an investigation," Apr. 1, 2015, pp. 1-2.
FDA, Food and Drug Administration. Guidance for Industry—Diabetes Mellitus: Developing Drugs and Therapeutic Biologics for Treatment and Prevention. pp. 1-34 (Feb. 2008).
Final Office issued in U.S. Appl. No. 12/617,805; dated May 25, 2016, pp. 1-9.
Final Rejection in U.S. Appl. No. 13/633,496; dated Aug. 26, 2015, pp. 1-16.
Final Rejection in U.S. Appl. No. 13/633,496; dated Oct. 13, 2016, pp. 1-10.
Final Rejection in U.S. Appl. No. 13/633,563; dated Apr. 8, 2016, pp. 1-12.
Final Rejection in U.S. Appl. No. 13/382,442; dated Jun. 13, 2014, pp. 1-29.
Final Rejection in U.S. Appl. No. 13/123,835; dated Nov. 18, 2015, pp. 1-16.
Final Rejection in U.S. Appl. No. 13/382,442; dated Sep. 21, 2016, pp. 1-32.
Final Rejection in U.S. Appl. No. 13/509,507; dated May 13, 2016, pp. 1-11.
Forman et al., "Higher Levels of Albuminuria within the Normal Range Predict Incident Hypertension." Journal of American Social Nephrology, Oct. 2008, vol. 19 (10), pp. 1983-1988.
Game, "Novel hypoglycaemic agents: Considerations in patients with chronic kidney disease" Nephron Clin Pract.126(1):14-18 (Jan. 11, 2014).
GenBank: AAA52578.1 "GM-CSF [*Homo sapiens*]" dated Nov. 8, 1994; accessed Jan. 18, 2017, one page.
GenBank: AAA59149.1 "Interleukin 4 [*Homo sapiens*]" dated Jan. 6, 1995; accessed Jan. 18, 2017, one page.
Gen Bank: AAP20099.1 "Interferon Alpha 2B [*Homo sapiens*]" dated Apr. 30, 2003; accessed Jan. 18, 2017, one page.
Gerstein et al., "Albuminuria and risk of cardiovascular events, death, and heart failure in diabetic and nondiabetic Individuals." JAMA 286(4):421-6 (Jul. 2001).
Giacometti et al., "In vitro activity of the histatin derivative P-113 against multidrug-resistant pathogens responsible or pneumonia in immunocompromised patients." 49 (3):1249-52 (Mar. 2005).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; Epub Feb. 8, 2014).
Glucophage XR, Product Information, Bristol-Meyers Squibb Company (Jan. 2009).
Gromada et al., "Alpha-Cells of the Endocrine Pancreas: 35 Years of Research but the Enigma Remains" Endocrine Reviews 28(1):84-116 (Jan. 2007).
Harkavyi & Whitton, "Glucagon-like peptide 1 receptor stimulation as a means of neuroprotection" British Journal of Pharmacology 159(3):495-501 (2010; Epub Jan. 29, 2010).
Hasslacher et al., "Diabetic kidney disease" Expand Clin Endocrinol Diabetes 122(7):391-94 (Jul. 2014).
Hinnen, "Therapeutic Options for the Management of Postprandial Glucose in Patients With Type 2 Diabetes on Basal Insulin," Clinical Diabetes, 2015, vol. 33 (4), pp. 175-180.

(56) References Cited

OTHER PUBLICATIONS

Holman et al., "Three-year efficacy of complex insulin regimens in type 2 diabetes." N Engl J Med. 361 (18):1736-47 (Oct. 2009; Epub Oct. 22, 2009).
Hubschle et al., "Anti-atherosclerotic activity of lixisenatide in ApoE knockout mice" Abstract 809, Diabetologia, 55 (Supplement 1 ):S334 (Oct. 2012).
IDF, International Diabetes Federation Guideline Development Group, "Guideline for management of postmeal glucose in diabetes," Diabetes Research Clinical Practice, 2012, pp. 1-13.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.
International Search Report by the ISA for International Application No. PCT/EP2016/055267; dated Jun. 7, 2016, pp. 1-7.
International Search Report by the ISA for International Application No. PCT/EP2016/055267; dated May 20, 2016, pp. 1-7.
International Search Report by the ISA for International Application No. PCT/EP2016/055954; dated Sep. 9, 2016, pp. 1-12.
Inzucchi et al., "Management of hyperglycaemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).
Juniper et al., "Determining a minimal important change in a disease-specific quality of life questionnaire." J Clin Epidemiol 47(1):81-87 (Jan. 1994).
Katz et al., "The clinical burden of type 2 diabetes in patients with acute coronary syndromes: Prognosis and implications for short- and long-term management" Diabetes and Vascular Disease Research, 11 (6):395-409 (Nov. 2014).
Kelly et al., "Systematic Review: Glucose Control and Cardiovascular Disease in Type 2 Diabetes." Annals Internal Medicine, 151(6):394-403 (Sep. 2009; Epub Jul. 20, 2009).
Khaw et al., "Glycated Haemoglobin, Diabetes, and Mortality in Men in Norfolk Cohort of European Prospective Investigation of Cancer and Nutrition (EPIC Norfolk)." BMJ, Jan. 2001, vol. 322 (7277), pp. 15-18.
King et al., Global burden of diabetes, 1995-2025. Prevalence, numerical estimates and projections. Diabetes Care 21(9):1414-31 (Sep. 1998).
Kolotkin et al., "Assessing impact of weight on quality of life." Obes Res. 3(1 ):49-56 (Jan. 1995).
Kolotkin et al., "Development of a brief measure to assess quality of life in obesity." Obes Res. 9(2):102-11 (Feb. 2001).
Kondrat'ev VA Methodical Guidelines, May 7, 2010, p. 5 (in Russian only), found on Mar. 24, 2016, found from Internet: StudFields.ru>preview/4510743).
Korytkowski, "When oral agents fail: practical barriers to starting insulin." Int J Obes Relat Metab Disord. 26 Suppl 3 :S18-24 (Sep. 2002).
Lantus® Drug Description, downloaded Nov. 12, 2015, one page.
Lovshin & Drucker, "Incretin-based therapy for type 2 diabetes mellitus." Nat. Rev. Endocrinol. 5(5):262-69 (May 2009).
Madsbad, "Impact of Postprandial Glucose Control on Diabetes-Related Complications: How is the Evidence Evolving?" Journal of Diabetes and Its Complications, 2016, vol. 30, pp. 374-385, (Available online Oct. 9, 2015).
McFarlane, "Insulin therapy and type 2 diabetes: management of weight gain," J Clin Hypertens (Greenwich). 11 (10):601-7 (Oct. 2009).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Meadows et al, "The diabetes health profile (DHP): a new instrument for assessing the psychosocial profile of insulin requiring patients: development and psychometric evaluation," Qual. Life Res. 5(2):242-54 (Apr. 1996).

Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Meier et al., "Effect of lixisenatide vs liraglutide on glycaemic control, gastric emptying and safety parameters in optimised insuline glargine type 2 diabetes mellitus +/– metformin" Abstract and Poster 926, 5oth EASD Annual Meeting, Vienna, Austria Sep. 15-19, 2014, pp. 1-3.
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Merck Index, "Metformin", The Merck Index, 15th Edition (2013), RSC Publishing, 4 pages submitted, see entry 6009, p. 1102.
Miller et al., "Type 2 diabetes in the child and adolescent", In: Lifshitz F (ed) Pediatric Endocrinology: 5th edition, vol. 1, New York, Marcel Dekker, pp. 169-188 (2007).
Miyazaki et al., "Improved Glycemic Control and Enhanced Insulin Sensitivity in Type 2 Diabetic Subjects Treated with Pioglitazone", Diabetes Care, 24(4):710-19 (Apr. 2001).
Monnier & Colette, "Addition of rapid-acting insulin to basal insulin therapy in type 2 diabetes: indications and modalities." Diabetes Metab 32(1):7-13 (Feb. 2006).
Monnier et al., "Postprandial and Basal Glucose in Type 2 Diabetes: Assessment and Respective Impacts" Diabetes Technology & Therapeutics, 13(Suppl 1):S25-S32 (2011).
Nathan et al., "Modem-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
Nihonn-Iyakuhin-shu Iryoyaku "Pioglitazone hydrochloride, Insulin sensitizing hypoglycemic agent" 2009 Edition, Jiho Inc. p. 1901 (2009). English summary submitted.
Non-Final Rejection in U.S. Appl. No. 13/633,496; dated Apr. 21, 2016, pp. 1-12.
Non-Final Rejection in U.S. Appl. No. 13/509,542; dated Nov. 23, 2016, pp. 1-34.
Nowels et al., "Validation of the EQ-50 quality of life instrument in patients after myocardial infarction." Qual Life Res 14(1):95-105 (Feb. 2005).
Osterbye et al., "Sulfatide Promotes the Folding of Proinsulin, Preserves Insulin Crystals, and Mediates Its Monomerization,"Journal of Glycobiology, 11(6):473-79 (2001).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Park et al., "Long-Term Treatment of Glucagon-Like Peptide-1 Analog Exendin-4 Ameliorates Diabetic Nephropathy through Improving Metabolic Anomalies in db/db Mice." Journal American Society Nephrology, 18(4):1227-38, (Apr. 2007; Epub Mar. 14, 2007).
Partial International Search Report by the ISA for International Application No. PCT/EP2016/055954; dated Jun. 21, 2016, pp. 1-6.
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (2011).
Petersen & Christensen et al., Clinical potential of lixisenatide once daily treatment for type 2 diabetes mellitus Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).

(56) References Cited

OTHER PUBLICATIONS

Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (2013).
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Raman & Heptulla, "New potential adjuncts to treatment of children with type 1 diabetes mellitus" Pediatric Research, 65(4):370-74 (Apr. 2009).
Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Ray et al., "Effect of intensive control of glucose on cardiovascular outcomes and death in patients with diabetes mellitus: a meta-analysis of randomized controlled trials." Lancet 373(9677):1765-72 (May 2009).
Register of medicaments (RM), 2003, issue 10, p. 517.
Remington: The Science and Practice of Pharmacy, Twentieth Edition, Lippincott Williams & Wilkins, USA, "Oral Hypoglycemic and Hyperglycemic Drugs" pp. 1373 and 1375; (2000).
"Remington: The Science and Practice of Pharmacy", Twentieth Edition, Lippincott Williams & Wilkins, USA, "Pancreatic Disorders" pp. 1081-1082 and "Metformin Hydrochloride" p. 1375, (2000, 5 pages).
Rosenstock J et al., Advancing Basal Insulin Glargine with Prandial Lixisenatide QD vs. Insulin Glulisine QD or TID in T2DM: The GetGoaiDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones & Khan, Insulin-associated weight gain in diabetes: causes, effects and coping strategies. Diabetes Obes Metab. 9(6):799-812 (Nov. 2007).
Russell-Jones, "Current developments in the treatment of diabetes: the incretin therapies" Br J Diabetes Vasc Dis. 10:21-30 (Feb. 2010).
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, p. 1-12 (2015). retrieved from the internet: http://en.sanofi.com/img/contentlstudy/PKD11475_summary.pdf (issued Jan. 13, 2015; retrieved on Jun. 16, 2015).
Sanofi Press Release entitled "Sanofi Announces Top-Line Results for Cardiovascular Outcomes Study of Lyxumia® (lixisenatide)." dated Mar. 19, 2015, Paris, France, pp. 1-2.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010 ).
Seino et al., "Lixisenatide significantly improves glycemic control in Asian patients with T2DM insufficiently controlled on basal insulin± SU." Diabetes, Abstract book for 71st Scientific Session. p. A76; Abstract 278-0R (2011).
Shaw et al., "US valuation of the EQ-5D health states: development and testing of the D1 valuation model." Med Care 43(3):203-20 (Mar. 2005).
Shehadeh et al., "Can GLP-1 preparations be used in children and adolescents with diabetes mellitus?" Pediatric Endocrinology Reviews, 11(3):324-27 (Mar. 2014).
Sillars et al., "Sulphonylurea-metformin combination therapy, cardiovascular disease and allcause mortality: the Fremantle Diabetes Study." Diabetes Obes Metab. 12(9):757-65 (Sep. 2010).
Spertus et al., "Monitoring the quality of life in patients with coronary heart disease." Am J Cardiol. 74(12):1240-44 (Dec. 1994).
Spertus et al., "Development and Evaluation of the Seattle Anginal Questionnaire: a New Functional Status Measure for Coronary Artery Disease." Journal American College of Cardiology, 25(2):333-41 (Feb. 1995).
Spertus et al., "Health Status Predicts Long-Term Outcome in Outpatients with Coronary Disease." Circulation, 106(1):43-49 (Jul. 2002).
Standardized Definitions for Cardiovascular Outcomes Trials: Draft Recommendations. Division of Metabolism and Endocrinology Products. Center for Drug Evaluation and Research (CDER). pp. 1-34, Mar. 24, 2010.
Tanner & Davies, "Clinical longitudinal standards for height and height velocity for North American children." J Pediatr. 107(3):317-29 (Sep. 1985).
The Advance Collaborative Group, "Intensive Blood Glucose Control and Vascular Outcomes in Patients with Type 2 Diabetes." New England Journal of Medicine, 358(24):2560-2572 (Jun. 2008).
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group, "Tight Blood Pressure Control and Risk of Macrovascular and Microvascular Complications in Type 2 Diabetes (UKPDS 38)," BMJ, 317:703-713 (Sep. 1998).
Vilsboll et al., "Liraglutide, a Long-Acting Human Glucagon-Like Peptide-1 Analog, Given as Monotherapy Significantly Improves Glycemic Control and Lowers Body Weight Without Risk of Hypoglycemia in Patients With Type 2 Diabetes," Journal of Diabetes Care, 30(6):1608-10 (2007).
Weir "Glucagon-like peptide-1 (7-37) actions on endocrine pancreas." Diabetes 38(3):338-42 (Mar. 1989).
Werner et al., "The GLP-1 Receptor Agonist AVE0010 Abolishes OGTT-Induces Blood Glucose Excursion in Healthy, Normoglycemic Dog without Risk of Hypoglycemia" Diabetes, 56 (Supplement 1): A129 (Jun. 2007). Abstract Submitted.
WHO, World Health Organization Media Center. Diabetes Fact Sheet. Available from: http://www.who.int/mediacentre/factsheets/fs312/en/index.html. Accessed Jun. 13, 2016, pp. 1-6.
WHO, World Health Organization Media Center. Obesity and overweight, Fact Sheet No. 311. Updated Jan. 2015, pp. 1-5.
Wikipedia® Entry for "Body Mass Index" Retrieved from the Internet: https://en.wikipedia.org/wiki/Body mass_index, 2016, pp. 1-14, retrieved Feb. 26, 2016.
Wikipedia® Entry for "Metformin" Retrieved from the Internet: https://en.wikipedia.org/wiki/Metformin 2016, pp. 1-21, retrieved Apr. 11, 2016.
Wikipedia® Entry for "Pioglitazone" Retrieved from the Internet: https://en.wikipedia.org/wiki/Pioglitazone 2016, pp. 1-3, retrieved Apr. 11, 2016.
Wikipedia® Entry for "Lixisenatide" Retrieved from the Internet: https://en.wikipedia.org/wiki/Lixisenatidehttps://en.wikipedia.org/wiki/Lixisenatide, pp. 1-2,updated Dec. 2015.
Wild et al., "Global prevalence of diabetes: estimates for the year 2000 and projections for 2030." Diabetes Care 27 (5):1047-53 (May 2004).
Williams et al., "Macrovascular disease in Diabetes." In handbook of Diabetes. 2nd ed. Williams G, Pickup JC, Eds. Oxford, UK, Blackwell Science pp. 151-158 (1999).
Wivioti et al., "Greater Clinical Benefit of More Intensive Oral Anti platelet Therapy With Prasugrel in Patients With Diabetes Mellitus in the Trial to Assess Improvement in Therapeutic Outcomes by

(56) References Cited

OTHER PUBLICATIONS

Optimizing Platelet Inhibition With Prasugrel-Thrombolysis in Myocardial Infarction 38," Circulation, 118(16):1626-36 (Oct. 2008; Epub Aug. 31, 2008).
Wohlfart et al., "Cardioprotective effects of lixisenatide in rat myocardial ischemia-reperfusion injury studies" Journal of Translational Medicine, 11(1):84, 12 pages (Mar. 2013).
Wolever et al., "Second-meal effect: low-glycemic-index foods eaten at dinner improve subsequent breakfast glycemic response." Am J Clin Nutr 48(4):1041-47 (Oct. 1988).
World Health Organisation Report on "Definition and Diagnosis of Diabetes Mellitus and Intermediate Hyperglycemia: Report of a WHO/IDF Consultation," 2006, pp. 1-50.
Wright et al., U.K. Prospective Diabetes Study Group. "Sulfonylurea inadequacy: efficacy of addition of insulin over years in patients with type 2 diabetes in the UK. Prospective Diabetes Study (UKPDS 57)." Diabetes Care 25 (2):330-36 (Feb. 2002).
Yusuf et al., "Effects of Clopidogrel in Addition to Aspirin in Patients with Acute Coronary Syndromes without ST-Segment Elevation." New England Journal Medical, 345(7):494-502 (Aug. 2001).
Zealand Pharma Company Announcement "Zealand Pharma, Additional positive results from Global Phase III program with-3-lixisenatide for type 2 diabetes", Apr. 12, 2011, pp. 1-3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Zeitler et al., "ISPAD Clinical Practice Consensus Guidelines 2014. Type 2 diabetes in the child and adolescent." Pediatr Diabetes 15(Suppl20):26-46 (Sep. 2014).
Zimmet et al., "Global and societal implications of the diabetes epidemic." Nature 41(6865):782-87 (Dec. 2001).
Zimmet et al., "The metabolic syndrome in children and adolescents." Lancet 369(9579):2059- 61 (Jun. 2007).
Zoungas et al., "Combined Effects of Routine Blood Pressure Lowering and Intensive Glucose Control on Macrovascular and Microvascular Outcomes in Patients With Type 2 Diabetes. New results from the ADVANCE trial." Diabetes Care, 32(11):2068-74, (Nov. 2009; Epub Aug. 3, 2009).
Ahmad & Swann, and Bloomgren "Exenatide and rare adverse events." N Engl J Med 35(18):1969-72 (May 2008).
Albert-Ludwigs University Freiburg, Institute fur Medizinische Biometrie and Statistik "Non-Inferiority Trials" dated Mar. 29, 2017, one page.
American Diabetes Association Annual Scientific Sessions, "New Diabetes Compound AVE0010 Showed Clear Dose Response Results With Once-A-Day Injection in Phase IIb Study", published Jun. 9, 2008, two pages.
American Diabetes Association, "Standards of Medical Care in Diabetes." Diabetes Care 28(Supplement 1): S4-S36 (Jan. 2005).
American Diabetes Association, "Standards of Medical Care in Diabetes 2008." Diabetes Care 31(Supplement 1):S12-S54.
Bastyr et al., "Therapy focused on lowering postprandial glucose, not fasting glucose, may be superior for lowering HbA1c. IOEZ Study Group." Diabetes Care 23(9):1236-41 (Sep. 2000).
Bennett, "Impact of the new WHO classification and diagnostic criteria." Diabetes Obes Metab 1(Supplement 2):S1-S6 (1999).
Buse et al., "Effects of exenatide (Exendin-4) on glycemic control over 30 weeks in sulfonylurea-treated patients with type 2 diabetes." Diabetes Care 27(11):2628-35 (Nov. 2004).
BYETTA® Labeling Revision, pp. 1-24 (Jan. 11, 2008).
BYETTA® European Public Assessment Report (EPAR), pp. 1-36 (Feb. 16, 2012).
BYETTA® Prescribing Information, pp. 1-34 (Revised Oct. 2009).
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
Definition of "prevent" Dictionary.com; last accessed Sep. 29, 2016, pp. 1-6.
Definition of "induce" Dictionary.com; last accessed Sep. 29, 2016, pp. 1-6.
Degn et al., "Effect of Intravenous Infusion of Exenatide (Synthetic Exendin-4) on Glucose-Dependent Insulin Secretion and Counter-regulation During Hypoglycemia." Diabetes 53(9):2397-2403 (Sep. 2004).
De la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).
De Venciana et al., "Postprandial versus preprandial blood glucose monitoring in women with gestational diabetes mellitus requiring insulin therapy." N Engl J Med 333(19):1237-41 (Nov. 1995).
Donahue et al., "Postchallenge glucose concentration and coronary heart disease in men of Japanese ancestry. Honolulu Heart Program." Diabetes 36(6):689-92 (Jun. 1987).
Eckert et al., "Assessing the progression of Parkinson's disease: A metabolic network approach," Lancet Neural. 6(10):926-32 (Oct. 2007).
European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16(9):716-730 (1999).
Forlenza et al., "Diagnosis and biomarkers of predementia in Alzheimer's disease," BMC Medicine 8:89 pp. 1-14 (Dec. 2010).
Ganz et al., "The association of body mass index with the risk of type 2 diabetes: a case-control study nested in an electronic health records system in the United States." Diabetology & Metabolic Syndrome, 6:50, pp. 1-8 (Apr. 2014).
Gerich, "Insulin glargine: long-acting basal insulin analog for improved metabolic control." Curr Med Res Opin. 20(1):31-37 (Jan. 2004).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Halimi, "DPP-4 inhibitors and GLP-1 analogues: for whom? Which place for incretins in the management of type 2 diabetic patients?", Diabetes & Metabolism 34(Supplement 2):S91-S95 (Feb. 2008).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Hollander & Kushner, "Type 2 Diabetes Comorbidities and Treatment Challenges: Rationale for DPP4-Inhibitors" Postgraduate Medicine, 122(3):71-80 (May 2010).
Janka et al., "Comparison of basal insulin added to oral agents versus twice-daily premixed insulin as initial insulin therapy for type 2 diabetes." Diabetes Care 28(2):254-59 (Feb. 2005).
Januvia—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Mac Conell et al., "Exenatide resulted in significantly greater improvements in posprandial glycaemic control compared to sitagliptin," Diabetologia 51(Supplement 1) p. S348, Abstract 872, one page (2008).

(56) References Cited

OTHER PUBLICATIONS

Mainous et al., "Impact of the population at risk of diabetes on projections of diabetes burden in the United States: an epidemic on the way." Diabetologia 50(5):934-40 (May 2007; Epub Nov. 21, 2006).
Matthews et al., "Homeostasis model assessment: insulin resistance and β-cell function from fasting plasma glucose and insulin concentrations in man." Diabetologia 28(7):412-419 (Jul. 1985).
Mokdad et al., "The association of body mass index with the risk of type 2 diabetes: a case-control study nested in an electronic health records system in the United States." JAMA, 289(1):76-79 (Jan. 2003).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Mudaliar & Edelman, "Insulin therapy in type 2 diabetes." Endocrinol Metab Clin North Am. 30(4):935-82 (Dec. 2001).
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31(8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Riddle et al., "The treat-to-target trial: randomized addition of glargine or human NPH insulin to oral therapy of type 2 diabetes patients." Diabetes Care 26(11):3080-86 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Rosenstock J et al., Advancing Basal Insulin Glargine with Prandial Lixisenatide QD vs. Insulin Glulisine QD or TID in T2DM: The GetGoalDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Sacks et al., "Guidelines and Recommendations for Laboratory Analysis in the Diagnosis and Management of Diabetes Mellitus." Clinical Chemistry 48(3):436-72 (Mar. 2002).
Sanofi Presentation, "Natixis Conference on Diabetes" Pierre Chancel, pp. 1-23, Nov. 8, 2011.
Sloop et al., "Glucagon as a target for the treatment of Type 2 diabetes." Expert Opin Ther Targets. 9(3):593-600 (Jun. 2005).
Spasov & Chepurnova, "Scientific Approaches to Combination Therapy for Type 2 Diabetes Mellitus," Bulletin of Volgograd State Medical University,1(37):8-10 (2011). See English Absract.
Stumvoll et al., "Type 2 diabetes: Principles of pathogenesis and therapy." Lancet 365(9467):1333-46 (Apr. 2005).
UK Prospective Diabetes Study (UKPDS) Group 28: A randomized trial of efficacy of early addition of metformin in sulfonylurea-treated type 2 diabetes. Diabetes Care 1998; 21(1):87-92 (Jan. 1998).
van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
van Gaal & De Leeuw, "Rationale and options for combination treatment of type 2 diabetes." Diabletologia 46 (Supplement 1):M44-M50 (Mar. 2003).
Wahlin-Boll et al., "Impaired effect of sulfonylurea following increased dosage." Eur J Clin Pharmacol 22(1):21-25 (1982).
Werner, "Preclinical pharmacology of the new GLP-1 receptor agonist AVE0010", Ann. Endocrinol. (Paris), 69(2):164-65 (Apr. 2008).
Wikipedia® entry for "Stratified sampling" Retrieved on Mar. 28, 2017, pp. 1-4.
Williams et al., "Macrovascular disease in Diabetes." In handbook of Diabetes. 2nd ed. Williams G, Pickup JC, Eds. Oxford, UK, Blackwell Science Chapter 20; pp. 152-160 (2010).
Non-Final Rejection issued in U.S. Appl. No. 13/509,507; dated Sep. 21, 2016, pp. 1-7.
Non-Final Rejection issued in U.S. Appl. No. 14/172,151; dated Jan. 19, 2017, pp. 1-20.
Final Rejection issued in U.S. Appl. No. 14/172,151; dated Jan. 4, 2016, pp. 1-20.
Non-Final Rejection issued in U.S. Appl. No. 13/467,707; dated Jun. 30, 2016, pp. 1-9.
Non-Final Rejection issued in U.S. Appl. No. 13/467,707; dated Nov. 7, 2016, pp. 1-17.
Non-Final Rejection in U.S. Appl. No. 13/633,563; dated Oct. 5, 2016, pp. 1-12.
Non-Final Rejection issued in U.S. Appl. No. 14/303,895; dated Mar. 24, 2017, pp. 1-17.
Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
U.S. Appl. No. 14/965,586, filed Dec. 10, 2015, Souhami et al.
U.S. Appl. No. 14/995,910, filed Jan. 14, 2016, Bergmann et al.
U.S. Appl. No. 15/073,364, filed Mar. 17, 2016, Belder et al.
U.S. Appl. No. 15/068,286, filed Mar. 11, 2016, Roy et al.
Ahren, "GLP-1 for type 2 diabetes", Experimental Cell Research, 317(9):1239-45 (Jan. 2011).
American Diabetes Association, "Standards of Medical Care in Diabetes—2017" Diabetes Care 40(Supplement 1):S1-S142 (Jan. 2017).
Bergenstal et al., "Type 2 Diabetes: Assessing the Relative Risks and Benefits of Glucose-lowering Medications" The American Journal of Medicine 123(4):e9-e18 (Apr. 2010).
Byetta® Summary of Product Characteristics, updated Jul. 22, 2016, last accessed Jul. 31, 2017, pp. 1-13.
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Denker et al., "Exenatide (Exendin-4)-Induced Pancreatitis: A case report" Diabetes Care 29(2):471 (Feb. 2006).
Godoy-Matos, "The role of glucagon on type 2 diabetes at a glance," Diabetology & Metabolic Syndrome 6:91, pp. 1-5 (Aug. 2014).
Home et al., "Management of type 2 diabetes: updated NICE guidance" BMJ 336: 1306-1308 (Jun. 2008).
Ismail-Beigi et al., "Individulaizing Glycemic Targets in Type 2 Diabetes Mellitus: Implications of Recent Clinical Trials" Annals of Internal Medicine 154(8):554-559 (Apr. 2011).
Lee et al., "Goals of Glycemic Control in Frail Older Patients with Diabetes" JAMA 305(13):1350-51 (Apr. 2011).
Nathan et al., "Medical Management of Hyperglycemia in Type 2 Diabetes: A Consensus Algorithm for the Initiation and Adjustment of Therapy" Diabetologia 52:17-30 (2009; Epub Oct. 22, 2008).
NCT00866658 ClinicalTrials.gov, "GLP-1 agonist AVE0010 in patients with type 2 diabetes for glycemic control and safety evaluation, on top of basil insulin +/- sulfonylurea" p. 1-3, accessed Mar. 16, 2016 (updated Aug. 3, 2010).

(56) References Cited

OTHER PUBLICATIONS

NICE, National Institute for Health and Care Excellence, "Type 2 diabetes in adults: management" pp. 1-45 (Dec. 2, 2015).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-59 (Sep./Oct. 2009).
Sanofi-aventis Press Release, "Once Daily Lixisenatide in Combination with Basal Insulin Demonstrates Significant Improvement in Glucose Control" Paris, France (Sep. 30, 2010) pp. 1-3.
Sutter Medical Foundation, "Type 2 Diabetes Adult Outpatient Insulin Guidelines" Feb. 2011, pp. 1-6.
Non-Final Office Action issued in U.S. Appl. No. 15/340,969, dated Jul. 24, 2017, pp. 1-6.
Non-Final Office Action issued in U.S. Appl. No. 15/275,867, dated Jun. 1, 2017; pp. 1-11.
Non-Final Rejection issued in U.S. Appl. No. 15/197,378, dated Jun. 15, 2017, pp. 1-13.
Non-Final Rejection in U.S. Appl. No. 13/633,496; dated May 25, 2017, pp. 1-10.
U.S. Appl. No. 15/340,969, filed Nov. 1, 2016, Werner et al.
U.S. Appl. No. 15/595,929, filed May 15, 2017, Brunner-Schwarz et al.
U.S. Appl. No. 15/275,867, filed Sep. 26, 2016, Silvestre et al.
U.S. Appl. No. 15/237,285, filed Aug. 15, 2016, Boka et al.
U.S. Appl. No. 15/144,270, filed May 2, 2016, Silvestre et al.
U.S. Appl. No. 15/197,378, filed Jun. 29, 2016, Niemöller.
U.S. Appl. No. 15/657,683, filed Jul. 24, 2017, Souhami et al.
U.S. Appl. No. 15/646,760, filed Jul. 11, 2017, Roy et al.
U.S. Appl. No. 15/146,255, filed May 4, 2016, Hess et al.

\* cited by examiner

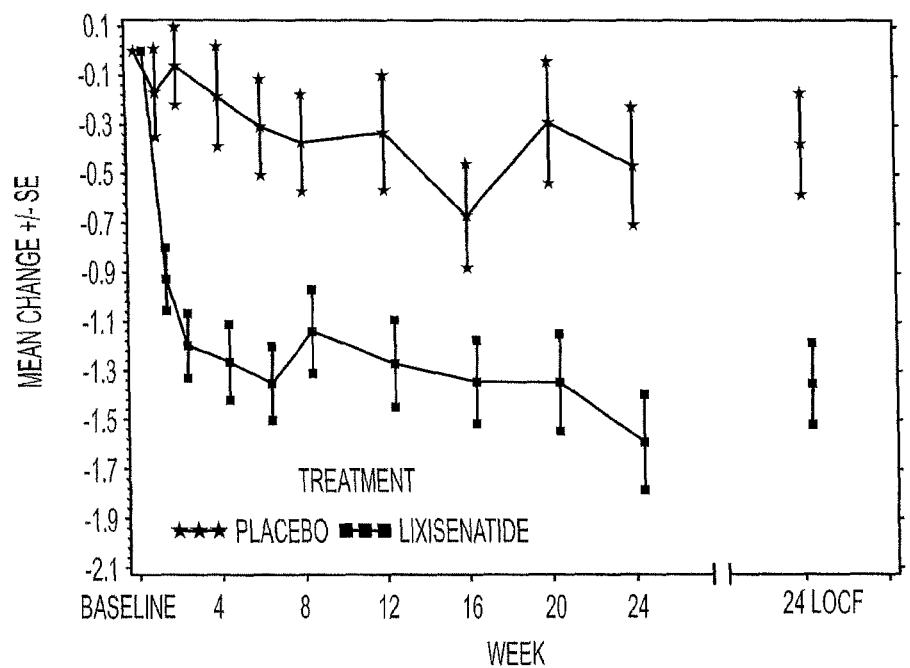

PLOT OF MEAN CHANGE IN AVERAGE 7-POINT SELF MONITORED PLASMA GLUCOSE (SMPG) (mmol/L) FROM BASELINE BY VISIT UP TO WEEK 24 AND AT ENDPOINT - mITT POPULATION

LOCF = LAST OBSERVATION CARRIED FORWARD.

NOTE: THE PLOT INCLUDED MEASUREMENTS OBTAINED BEFORE THE INTRODUCTION OF RESCUE MEDICATION AND UP TO THE DATE OF THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 4

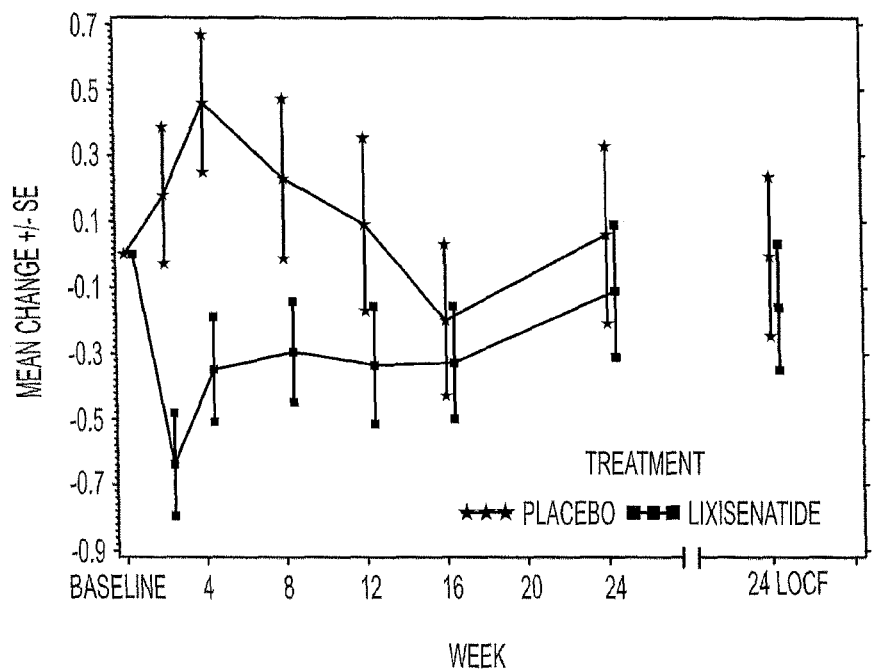

PLOT OF MEAN CHANGE IN FASTING PLASMA GLUCOSE (mmol/L) FROM BASELINE BY VISIT UP TO WEEK 24 AND AT ENDPOINT - mITT POPULATION

LOCF = LAST OBSERVATION CARRIED FORWARD.

NOTE: THE PLOT INCLUDED MEASUREMENTS OBTAINED BEFORE THE INTRODUCTION OF RESCUE MEDICATION AND UP TO 1 DAY AFTER THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 5

LOCF = LAST OBSERVATION CARRIED FORWARD

NOTE: THE PLOT INCLUDED MEASUREMENTS OBTAINED BEFORE THE INTRODUCTION OF RESCUE MEDICATION AND UP TO 3 DAYS AFTER THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

LOCF = LAST OBSERVATION CARRIED FORWARD.

NOTE: THE PLOT INCLUDED MEASUREMENTS OBTAINED BEFORE THE INTRODUCTION OF RESCUE MEDICATION AND UP TO THE DATE OF THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

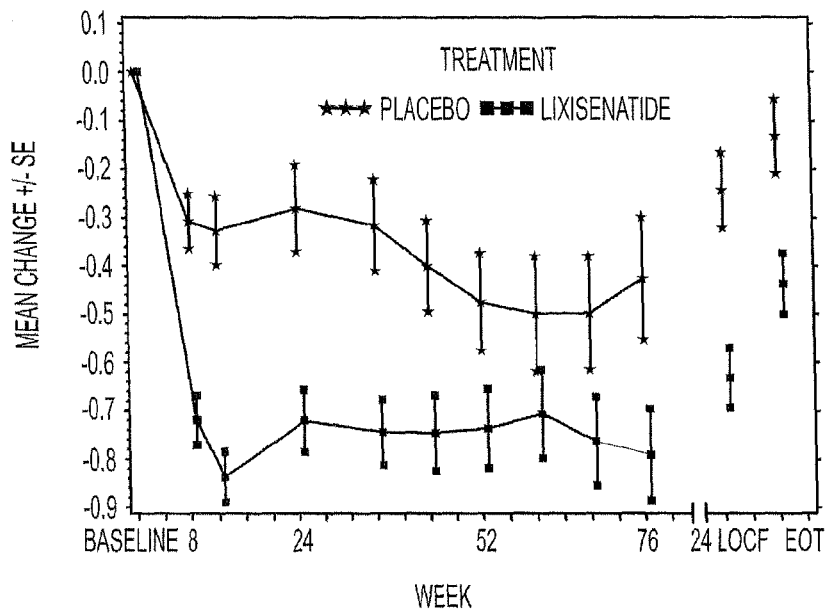

PLOT OF MEAN CHANGE IN HbA$_{1c}$ (%) FROM BASELINE BY VISIT AND AT ENDPOINT - mITT POPULATION

LOCF = LAST OBSERVATION CARRIED FORWARD.

EOT = LAST ON-TREATMENT VALUE.

THE ANALYSIS EXCLUDED MEASUREMENTS OBTAINED AFTER THE INTRODUCTION OF RESCUE MEDICATION AND/OR AFTER THE TREATMENT CESSATION PLUS 3 DAYS.

FOR WEEK 24 (LOCF), THE ANALYSIS INCLUDED MEASUREMENTS OBTAINED UP TO 3 DAYS AFTER THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 8

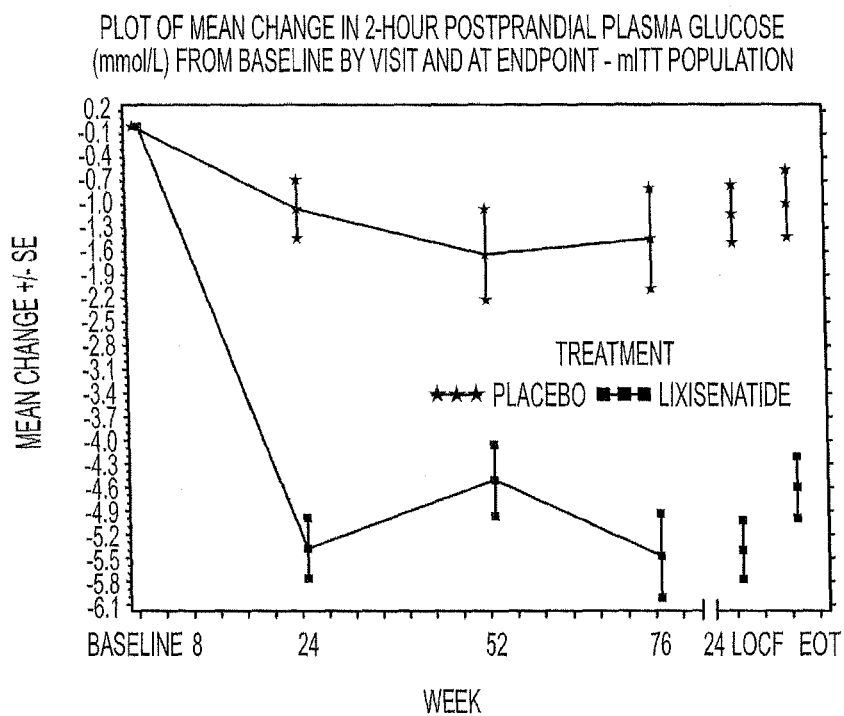

LOCF = LAST OBSERVATION CARRIED FORWARD.

EOT= LAST ON-TREATMENT VALUE.

THE ANALYSIS EXCLUDED MEASUREMENTS OBTAINED AFTER THE INTRODUCTION OF RESCUE MEDICATION AND/OR AFTER THE TREATMENT CESSATION.

FOR WEEK 24 (LOCF), THE ANALYSIS INCLUDED MEASUREMENTS OBTAINED UP TO THE DATE OF THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 9

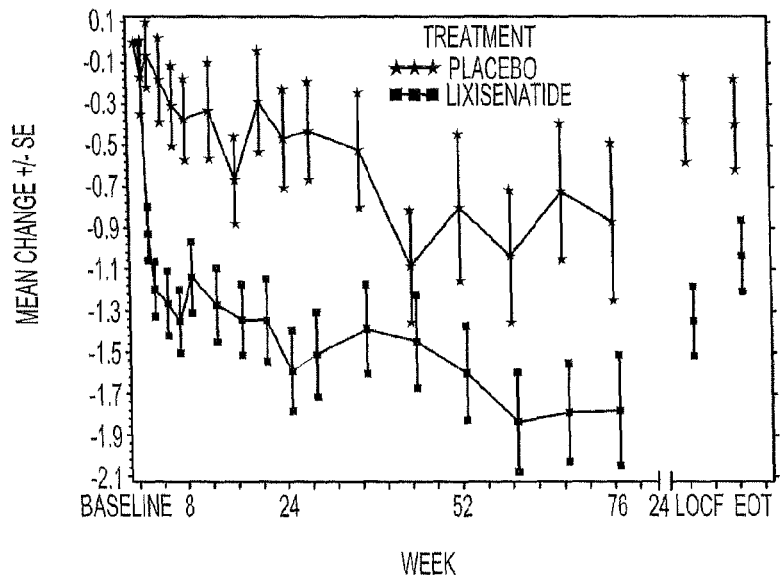

LOCF = LAST OBSERVATION CARRIED FORWARD.

EOT = LAST ON-TREATMENT VALUE.

THE ANALYSIS EXCLUDED MEASUREMENTS OBTAINED AFTER THE INTRODUCTION OF RESCUE MEDICATION AND/OR AFTER THE TREATMENT CESSATION.

FOR WEEK 24 (LOCF), THE ANALYSIS INCLUDED MEASUREMENTS OBTAINED UP TO THE DATE OF THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 10

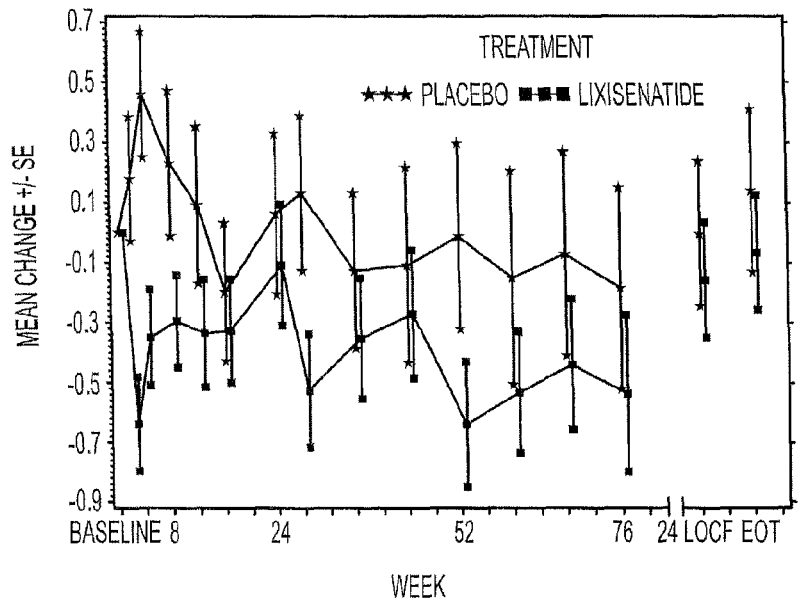

LOCF = LAST OBSERVATION CARRIED FORWARD.

EOT = LAST ON-TREATMENT VALUE.

THE ANALYSIS EXCLUDED MEASUREMENTS OBTAINED AFTER THE INTRODUCTION OF RESCUE MEDICATION AND/OR AFTER THE TREATMENT CESSATION PLUS 1 DAY.

FOR WEEK 24 (LOCF), THE ANALYSIS INCLUDED MEASUREMENTS OBTAINED UP TO ONE DAY AFTER THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 11

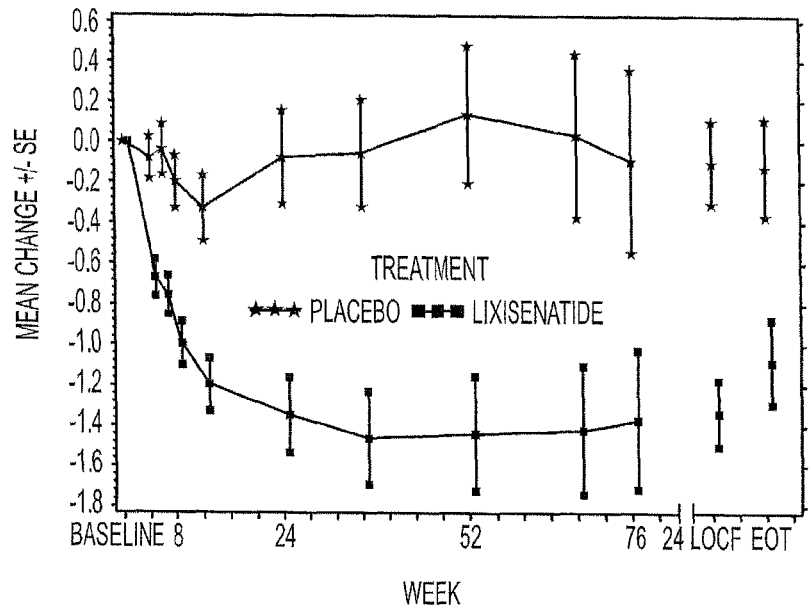

LOCF = LAST OBSERVATION CARRIED FORWARD.

EOT = LAST ON-TREATMENT VALUE.

THE ANALYSIS EXCLUDED MEASUREMENTS OBTAINED AFTER THE INTRODUCTION OF RESCUE MEDICATION AND/OR AFTER THE TREATMENT CESSATION PLUS 3 DAYS.

FOR WEEK 24 (LOCF), THE ANALYSIS INCLUDED MEASUREMENTS OBTAINED UP TO 3 DAYS AFTER THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 12

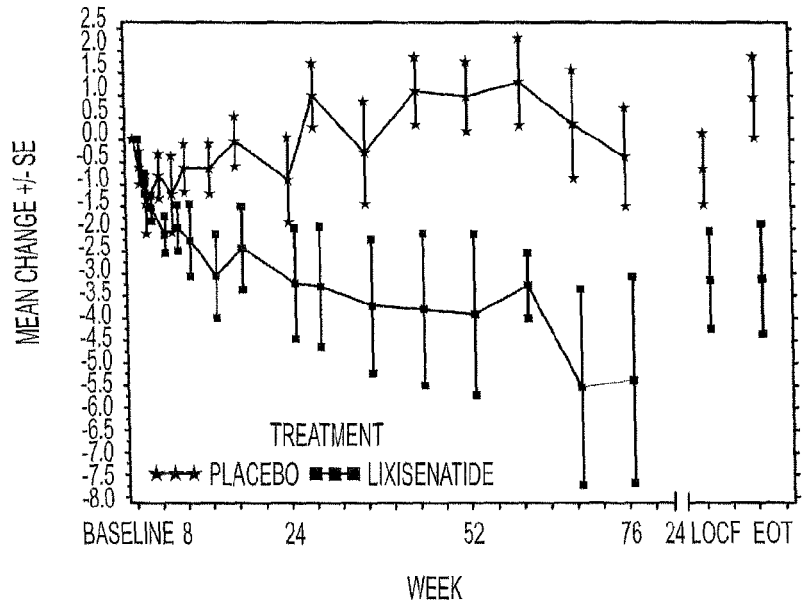

LOCF = LAST OBSERVATION CARRIED FORWARD.

EOT = LAST ON-TREATMENT VALUE.

THE ANALYSIS EXCLUDED MEASUREMENTS OBTAINED AFTER THE INTRODUCTION OF RESCUE MEDICATION AND/OR AFTER THE TREATMENT CESSATION.

FOR WEEK 24 (LOCF), THE ANALYSIS INCLUDED MEASUREMENTS OBTAINED UP TO THE DATE OF THE LAST DOSE OF THE DOUBLE-BLIND INVESTIGATIONAL PRODUCT INJECTION ON OR BEFORE VISIT 12 (WEEK 24), OR DAY 169 IF VISIT 12 (WEEK 24) IS NOT AVAILABLE.

FIG. 13

SEQUENCE LISTING

<160> NUMBER OF SEQ ID NOS: 2

<210> SEQ ID NO 1
<211> LENGTH: 44
<212> TYPE: PRT
<213> ORGANISM: Artificial Sequence
<220> FEATURE:
<223> OTHER INFORMATION: AVE0010, Synthetic or recombination peptide, derivative of Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Lys
            35                  40

```
<210> SEQ ID NO 2
<211> LENGTH: 39
<212> TYPE: PRT
<213> ORGANISM: Artificial Sequence
<220> FEATURE:
<223> OTHER INFORMATION: Exendin-4

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

PHARMACEUTICAL COMBINATION FOR IMPROVING GLYCEMIC CONTROL AS ADD-ON THERAPY TO BASAL INSULIN

Subject of the present invention is a pharmaceutical combination for use in glycemic control in diabetes type 2 patients, said combination comprising (a) desPro$^{36}$Exendin-4(1-39)-Lys$_6$-NH$_2$ (AVE0010, lixisenatide) or/and a pharmaceutically acceptable salt thereof, (b) a basal insulin or/and a pharmaceutically acceptable salt thereof, and (c) optionally metformin or/and a pharmaceutically acceptable salt thereof. A further subject of the present invention is a pharmaceutical combination for use in the prevention of hypoglycemia, said combination comprising (a) desPro$^{36}$Exendin-4(1-39)-Lys$_6$-NH$_2$ or/and a pharmaceutically acceptable salt thereof, (b) a basal insulin or/and a pharmaceutically acceptable salt thereof, and (c) optionally metformin or/and a pharmaceutically acceptable salt thereof. Another subject of the present invention is a pharmaceutical combination for use in inducing weight loss in diabetes type 2 patients or/and for preventing weight gain in diabetes type 2 patients, said combination comprising (a) desPro$^{36}$Exendin-4(1-39)-Lys$_6$-NH$_2$ or/and a pharmaceutically acceptable salt thereof, (b) a basal insulin or/and a pharmaceutically acceptable salt thereof, and (c) optionally metformin or/and a pharmaceutically acceptable salt thereof.

(BMI)≥30. In these patients the risks of diabetes overlap with the risks of overweight, leading e.g. to an increase of cardiovascular diseases compared to diabetes type 2 patients being of a normal weight. Thus, it is particularly necessary to treat diabetes in these patients while reducing the overweight.

Metformin is a biguanide hypoglycemic agent used in the treatment of non-insulin-dependent diabetes mellitus (diabetes mellitus type 2) not responding to dietary modification. Metformin improves glycemic control by improving insulin sensitivity and decreasing intestinal absorption of glucose. Metformin is usually administered orally. However, control diabetes mellitus type 2 in obese patients by metformin may be insufficient. Thus, in these patients, additional measures for controlling diabetes mellitus type 2 may be required.

Insulin is a polypeptide having 51 amino acid residues. Insulin consists of the A chain having 21 amino acid residues, and the B chain having 30 amino acid residues. The chains are coupled by 2 disulfide bridges. Insulin formulations have been used for a long time for therapy of diabetes mellitus type 1 and 2. Recently, insulin derivatives and insulin analogues have been used.

The compound desPro$^{36}$Exendin-4(1-39)-Lys$_6$-NH$_2$ (AVE0010, lixisenatide) is a derivative of Exendin-4. AVE0010 is disclosed as SEQ ID NO:93 in WO 01/04156:

```
SEQ ID NO: 1: AVE0010 (44 AS)
H-G-E-G-T-F-T-S-D-L-S-K-Q-M-E-E-E-A-V-R-L-F-I-E-W-L-K-N-G-G-P-S-S-G-A-P-P-S-
K-K-K-K-K-K-NH2

SEQ ID NO: 2: Exendin-4 (39 AS)
H-G-E-G-T-F-T-S-D-L-S-K-Q-M-E-E-E-A-V-R-L-F-I-E-W-L-K-N-G-G-P-S-S-G-A-P-P-P-
S-NH2
```

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to diabetes type 1, there is not generally a lack of insulin in diabetes type 2 but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macrovascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as closely as possible.

A particular risk exists for overweight patients suffering from diabetes type 2, e.g. patients with a body mass index Exendins are a group of peptides which can lower blood glucose concentration. The Exendin analogue AVE0010 is characterised by C-terminal truncation of the native Exendin-4 sequence. AVE0010 comprises six C-terminal lysine residues not present in Exendin-4.

In the context of the present invention, AVE0010 includes pharmaceutically acceptable salts thereof. The person skilled in the art knows pharmaceutically acceptable salts of AVE0010. A preferred pharmaceutically acceptable salt of AVE0010 employed in the present invention is acetate.

In the Example of the present invention, it has been demonstrated that AVE0010 (Lixisenatide) in an add-on therapy to basal insulin and optionally metformin significantly improved glycemic control and decreased weight:

HbA1c was significantly decreased.

postprandial plasma glucose concentration was significantly improved with lixisenatide.

Significant weight loss was induced.

A significant decrease in daily basal insulin dose could be observed.

No significant increase in the incidence of hypoglycemia was observed.

A first aspect of the present invention is a pharmaceutical combination for use in glycemic control in diabetes type 2 patients, said combination comprising (a) desPro$^{36}$Exendin-4(1-39)-Lys$_6$-NH$_2$ or/and a pharmaceutically acceptable salt thereof, (b) a basal insulin or/and a pharmaceutically acceptable salt thereof, and (c) optionally metformin or/and a pharmaceutically acceptable salt thereof.

As demonstrated by the Example disclosed herein, the combination as described herein can be used for improving glycemic control. In the present invention, "improvement of glycemic control" or "glycemic control" in particular refers to improvement of postprandial plasma glucose concentration, improvement of fasting plasma glucose concentration, or/and improvement of the $HbA_{1c}$ value.

Metformin is the international nonproprietary name of 1,1-dimethylbiguanide (CAS Number 657-24-9). In the present invention, the term "metformin" includes any pharmaceutically acceptable salt thereof.

In the present invention, metformin may be administered orally. The skilled person knows formulations of metformin suitable for treatment of diabetes type 2 by oral administration. Metformin may be administered to a subject in need thereof, in an amount sufficient to induce a therapeutic effect. Metformin may be administered in a dose of at least 1.0 g/day or at least 1.5 g/day. For oral administration, metformin may be formulated in a solid dosage form, such as a tablet or pill. Metformin may be formulated with suitable pharmaceutically acceptable carriers, adjuvants, or/and auxiliary substances.

In the present invention, desPro$^{36}$Exendin-4(1-39)-Lys$_6$-NH$_2$ or/and a pharmaceutically acceptable salt may be administered in an add-on therapy to administration of a basal insulin and optionally metformin.

In the present invention, the terms "add-on", "add-on treatment" and "add-on therapy" relate to treatment of diabetes mellitus type 2 with metformin, AVE0010 and the basal insulin. Metformin, AVE0010 and the basal insulin may be administered within a time interval of 24 h. Metformin, AVE0010 and the basal insulin each may be administered in a once-a-day-dosage. Metformin, AVE0010 and basal insulin may be administered by different administration routes. Metformin may be administered orally, and AVE0010 and the basal insulin may be administered parenterally.

In the present invention, the terms "add-on", "add-on treatment" and "add-on therapy" also relate to treatment of diabetes mellitus type 2 with AVE0010 and the basal insulin. AVE0010 and the basal insulin may be administered within a time interval of 24 h. AVE0010 and the basal insulin each may be administered in a once-a-day-dosage. AVE0010 and basal insulin may be administered parenterally.

In the present invention, "basal insulin" includes suitable pharmaceutically acceptable salts thereof. In the present invention, any basal insulin can be used. In particular, the basal insulin can be selected from insulin Glargine, Detemir, NPH, Lente, Ultralente, Novolin, Humalog and mixtures thereof. The mixture may comprise two different basal insulins. For example, a mixture comprising Detemir and Glargine, or a mixture comprising NPH and Novolin, may be employed. Preferably, the basal insulin is insulin Glargin (Lantus), or a mixture comprising insulin Glargine.

Insulin glargine (Lantus) is Gly(A21)-Arg(B31)-Arg(B32)-human insulin. In the present invention, insulin Glargine includes pharmaceutically acceptable salts thereof.

The basal insulin or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. The basal insulin or/and a pharmaceutically acceptable salt thereof may be administered in a suitable amount, for instance in an amount in the range of 15 to 80 U per dose.

In the present invention, the basal insulin or/and a pharmaceutically acceptable salt thereof may be administered in a daily dose in the range of 15 to 80 U. Insulin glargine or/and a pharmaceutically acceptable salt thereof may be administered once daily, for example by one injection per day.

The skilled person knows formulations of basal insulin, including suitable pharmaceutically acceptable carriers, adjuvants or/and auxiliary substances.

In the present invention, the basal insulin or/and a pharmaceutically acceptable salt thereof may be provided in a liquid composition The skilled person knows liquid compositions of basal insulins suitable for parenteral administration.

In the present invention, the basal insulin or/and the pharmaceutically acceptable salt thereof may be administered to a subject in need thereof, in an amount sufficient to induce a therapeutic effect.

The subject to be treated by the medicament of the present invention suffering from diabetes type 2 may be a subject suffering from diabetes type 2, wherein diabetes type 2 is not adequately controlled by treatment with the basal insulin and optionally metformin alone, for instance with a dose of 15 to 80 U/day insulin for 3 months and optionally with a dose of at least 1.0 g/day metformin or at least 1.5 g/day metformin for 3 months. In the present invention, a subject having diabetes type 2 of which is not adequately controlled may have a HbA1c value in the range of 7% to 10%.

The subject to be treated by the medicament of the present invention suffering from diabetes type 2 may be an obese subject. In the present invention, an obese subject may have a body mass index of at least 30 kg/m$^2$.

The subject to be treated by the medicament of the present invention suffering from diabetes type 2 may have a normal body weight. In the present invention, a subject having normal body weight may have a body mass index in the range of 17 kg/m$^2$ to 25 kg/m$^2$, or 17 kg/m$^2$ to <30 kg/m$^2$.

The subject to be treated by the medicament of the present invention may be an adult subject. The subject may have an age of at least 18 years of may have an age in the range of 18 to 80 years, of 18 to 50 years, or 40 to 80 years, or 50 to 60 years. The subject may be younger than 50 years.

The subject to be treated by the medicament of the present invention may suffer from diabetes mellitus type 2 for at least 1 year or at least 2 years. In particular, in the subject to be treated, diabetes mellitus type 2 has been diagnosed at least 1 year or at least 2 years before onset of therapy by the medicament of the present invention.

The subject to be treated may have a $HbA_{1c}$ value of at least about 8% or at least about 7.5%. The subject may also have a $HbA_{1c}$ value of about 7 to about 10%. The example of the present invention demonstrates that treatment by AVE0010 results in a reduction of the $HbA_{1c}$ value in diabetes type 2 patients.

In yet another aspect of the present invention, the combination as described herein can be used for improving the $HbA_{1c}$ value in a patient suffering from diabetes type 2. Improving the $HbA_{1c}$ value means that the $HbA_{1c}$ value is reduced below 6.5% or 7%, for example after treatment for at least one month, at least two months, or at least three months.

In yet another aspect of the present invention, the combination as described herein can be used for improving glucose tolerance in a patient suffering from diabetes type 2. Improving glucose tolerance means that the postprandial plasma glucose concentration is reduced by the active agent of the present invention. Reduction means in particular that the plasma glucose concentration reaches normoglycemic values or at least approaches these values.

In the present invention, normoglycemic values are blood glucose concentrations of in particular 60-140 mg/dl (corresponding to 3,3 bis 7.8 mM/L). This range refers in particular to blood glucose concentrations under fasting conditions and postprandial conditions.

The subject to be treated may have a 2 hours postprandial plasma glucose concentration of at least 10 mmol/L, at least 12 mmol/L, or at least 14 mmol/L. These plasma glucose concentrations exceed normoglycemic concentrations.

The subject to be treated may have a glucose excursion of at least 2 mmol/L, at least 3 mmol/L, at least 4 mmol/L or at least 5 mmol/L. In the present invention, the glucose excursion is in particular the difference of the 2 hours postprandial plasma glucose concentration and the plasma glucose concentration 30 minutes prior to a meal test.

"Postprandial" is a term that is well known to a person skilled in the art of diabetology. The term "postprandial" describes in particular the phase after a meal or/and exposure to glucose under experimental conditions. In a healthy person this phase is characterised by an increase and subsequent decrease in blood glucose concentration. The term "postprandial" or "postprandial phase" typically ends up to 2 h after a meal or/and exposure to glucose.

The subject to be treated as disclosed herein may have a fasting plasma glucose concentration of at least 8 mmol/L, at least 8.5 mmol/L or at least 9 mmol/L. These plasma glucose concentrations exceed normoglycemic concentrations.

In another aspect of the present invention, the combination as described herein can be used for improving (i.e. reducing) fasting plasma glucose in a patient suffering from diabetes type 2. Reduction means in particular that the plasma glucose concentration reaches normoglycemic values or at least approaches these values.

A further aspect of the present invention is a method for improving glycemic control in diabetes type 2 patients, said method comprising administering desPro$^{36}$Exendin-4(1-39)-Lys$_6$-NH$_2$ or/and a pharmaceutically acceptable salt thereof, in combination with metformin to a subject in need thereof. In particular, the combination as described herein may be administered. In the method of the present invention, the subject may be the subject defined herein.

The combination of the present invention can be used in the treatment of one or more of the medical indications described herein, for example in treatment of diabetes type 2 patients, or for conditions associated with diabetes type 2, such as improvement of glycemic control, reduction of the fasting plasma glucose concentration, for the improvement of glucose excursion, reduction of the postprandial plasma glucose concentration, improvement of glucose tolerance, improving the HbA$_{1c}$ value, for the prevention of hypoglycaemia, for weight loss or/and prevention of weight gain.

In the present invention, desPro$^{36}$Exendin-4(1-39)-Lys$_6$-NH$_2$ or/and the pharmaceutically acceptable salt thereof may be administered to a subject in need thereof, in an amount sufficient to induce a therapeutic effect.

In the present invention, desPro$^{36}$Exendin-4(1-39)-Lys$_6$-NH$_2$ or/and the pharmaceutically acceptable salt thereof may be formulated with suitable pharmaceutically acceptable carriers, adjuvants, or/and auxiliary substances.

The compound desPro$^{36}$Exendin-4(1-39)-Lys$_6$-NH$_2$ or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. The compound desPro$^{36}$Exendin-4(1-39)-Lys$_6$-NH$_2$ or/and a pharmaceutically acceptable salt thereof may be administered in a suitable amount, for instance in an amount in the range of 10 to 15 µg per dose or 15 to 20 µg per dose.

In the present invention, desPro$^{36}$Exendin-4(1-39)-Lys$_6$-NH$_2$ or/and a pharmaceutically acceptable salt thereof may be administered in a daily dose in the range of 10 to 20 µg, in the range of 10 to 15 µg, or in the range of 15 to 20 µg. DesPro$^{36}$Exendin-4(1-39)-Lys$_6$-NH$_2$ or/and a pharmaceutically acceptable salt thereof may be administered by one injection per day.

In the present invention, desPro$^{36}$Exendin-4(1-39)-Lys$_6$-NH$_2$ or/and a pharmaceutically acceptable salt thereof may be provided in a liquid composition. The skilled person knows liquid compositions of AVE0010 suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition comprising desPro$^{36}$Exendin-4(1-39)-Lys$_6$-NH$_2$ or/and a pharmaceutically acceptable salt thereof may comprise a suitable preservative. A suitable preservative may be selected from phenol, m-cresol, benzyl alcohol and p-hydroxybenzoic acid ester. A preferred preservative is m-cresol.

The liquid composition comprising desPro$^{36}$Exendin-4(1-39)-Lys$_6$-NH$_2$ or/and a pharmaceutically acceptable salt thereof may comprise a tonicity agent. A suitable tonicity agent may be selected from glycerol, lactose, sorbitol, mannitol, glucose, NaCl, calcium or magnesium containing compounds such as CaCl$_2$. The concentration of glycerol, lactose, sorbitol, mannitol and glucose may be in the range of 100-250 mM. The concentration of NaCl may be up to 150 mM. A preferred tonicity agent is glycerol.

The liquid composition comprising desPro$^{36}$Exendin-4(1-39)-Lys$_6$-NH$_2$ or/and a pharmaceutically acceptable salt thereof may comprise methionine from 0.5 µg/mL to 20 µg/mL, preferably from 1 µg/ml to 5 µg/ml. Preferably, the liquid composition comprises L-methionine.

Another aspect of the present invention is a pharmaceutical combination for use in inducing weight loss in diabetes type 2 patients or/and for preventing weight gain in diabetes type 2 patients, said combination comprising
  (a) desPro$^{36}$Exendin-4(1-39)-Lys$_6$-NH$_2$ or/and a pharmaceutically acceptable salt thereof,
  (b) a basal insulin or/and a pharmaceutically acceptable salt thereof, and
  (c) optionally metformin or/and a pharmaceutically acceptable salt thereof.

A further aspect of the present invention is a method for inducing weight loss in diabetes type 2 patients or/and for preventing weight gain in diabetes type 2 patients, said method comprising administering desPro$^{36}$Exendin-4(1-39)-Lys$_6$-NH$_2$ or/and a pharmaceutically acceptable salt thereof, in combination with metformin to a subject in need thereof. In particular, the combination as described herein may be administered. In the method of the present invention, the subject may be the subject defined herein.

Yet another aspect of the present invention is a pharmaceutical combination for use in the prevention of hypoglycaemia in diabetes mellitus type 2 patients, said combination comprising
(a) desPro$^{36}$Exendin-4(1-39)-Lys$_6$-NH$_2$ or/and a pharmaceutically acceptable salt thereof,
(b) a basal insulin or/and a pharmaceutically acceptable salt thereof, and
(c) optionally metformin or/and a pharmaceutically acceptable salt thereof.

In particular, the pharmaceutical combination is used for the prevention of symptomatic hypoglycaemia or/and severe symptomatic hypoglycaemia in a diabetes mellitus type 2 patient.

In the present invention, hypoglycaemia is a condition wherein a diabetes mellitus type 2 patient experiences a plasma glucose concentration of below 60 mg/dL (or below 3.3 mmol/L), below 50 mg/dL, below 40 mg/dL, or below 36 mg/dL.

By the method of the present invention, hypoglycaemia can be reduced to below 12%, below 11%, below 10%, below 9%, below 8%, below 7%, below 6% or below 5% of diabetes type 2 patients receiving the combination of lixisenatide or/and a pharmaceutically acceptable salt thereof, basal insulin or/and a pharmaceutically acceptable salt thereof and optionally metformin or/and a pharmaceutically acceptable salt thereof, as described herein.

In the present invention, "symptomatic hypoglycaemia" is a condition associated with a clinical symptom that results from the hypoglycaemia, wherein the plasma glucose concentration is below 60 mg/dL (or below 3.3 mmol/L), below 50 mg/dL, or below 40 mg/dL. A clinical symptoms can be, for example, sweating, palpitations, hunger, restlessness, anxiety, fatigue, irritability, headache, loss of concentration, somnolence, psychiatric disorders, visual disorders, transient sensory defects, transient motor defects, confusion, convulsions, and coma. In the present invention, one or more clinical symptoms of symptomatic hypoglycaemia, as indicated herein, can be selected.

Symptomatic hypoglycaemia may be associated with prompt recovery after oral carbohydrate administration.

In the present invention, "severe symptomatic hypoglycaemia" is a condition with a clinical symptom, as indicated herein, that results from hypoglycaemia, wherein the plasma glucose concentration is below 36 mg/dL (or below 2.0 mmol/L). Severe symptomatic hypoglycaemia can be associated with acute neurological impairment resulting from the hypoglycaemic event. In a severe symptomatic hypoglycaemia, the patient may require the assistance of another person, if, for example, the patient could not treat or help him/herself due to the acute neurological impairment. The definition of severe symptomatic hypoglycaemia may include all episodes in which neurological impairment is severe enough to prevent self-treatment and which were thus thought to place patients at risk for injury to themselves or others. The acute neurological impairment may be at least one selected from somnolence, psychiatric disorders, visual disorders, transient sensory defects, transient motor defects, confusion, convulsions, and coma.

Severe symptomatic hypoglycaemia may be associated with prompt recovery after oral carbohydrate, intravenous glucose, or/and glucagon administration.

A further aspect of the present invention is a method for preventing hypoglycemia in diabetes type 2 patients, said method comprising administering desPro$^{36}$Exendin-4(1-39)-Lys$_6$-NH$_2$ or/and a pharmaceutically acceptable salt thereof, in combination with a basal insulin or/and a pharmaceutically acceptable salt thereof, and optionally with metformin to a subject in need thereof. In particular, the combination as described herein may be administered. In the method of the present invention, the subject may be the subject defined herein.

Yet another aspect of the present invention refers to the use of the combination as described herein for the manufacture of a medicament for the treatment of a medical indication, as described herein. For example, the combination of the present invention can be used for the manufacture of a medicament for the treatment of diabetes type 2 patients, or for the treatment of conditions associated with diabetes type 2, such as improvement of glycemic control, reduction of the fasting plasma glucose concentration, for the improvement of glucose excursion, reduction of the postprandial plasma glucose concentration, improving the HbA$_{1c}$ value, or/and improvement of glucose tolerance. In another example, the combination as described herein can be used for the manufacture of a medicament for inducing weight loss in diabetes type 2 patients or/and for preventing weight gain in diabetes type 2 patients. In yet another example, the combination as described herein can be used for the manufacture of a medicament for preventing hypoglycaemia in diabetes type 2 patients. The medicament can be formulated as described herein. For example the medicament can comprise a parenteral formulation of AVE0010 or/and a pharmaceutically acceptable salt thereof, a parenteral formulation of the basal insulin or/and a pharmaceutically acceptable salt thereof, and an optional oral formulation of metformin or/and a pharmaceutically acceptable salt thereof.

The invention is further illustrated by the following example and figures.

FIGURE LEGENDS

FIG. 1—Study design

Figure 2:
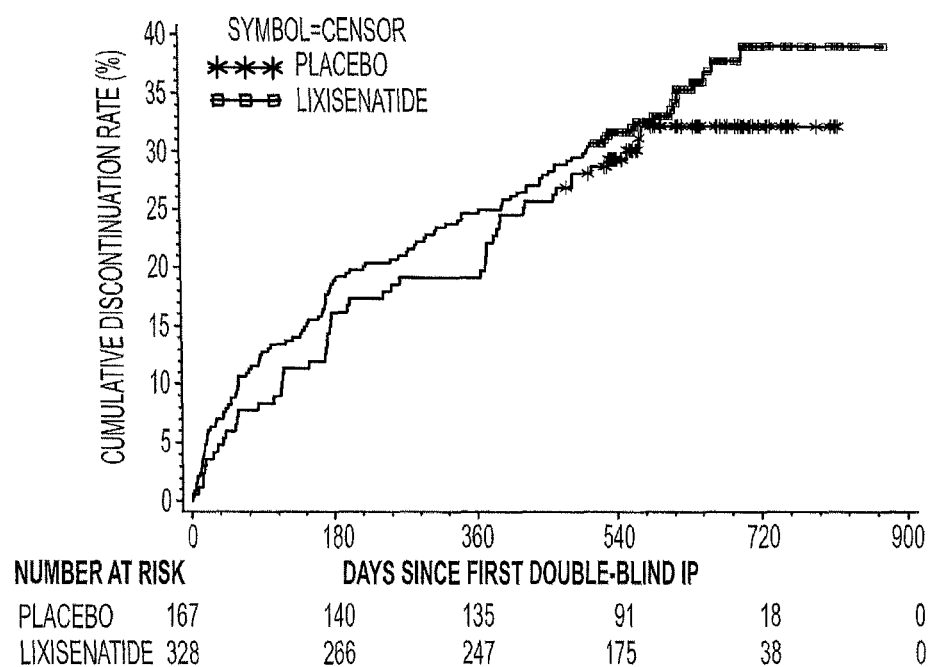
Figure 3:
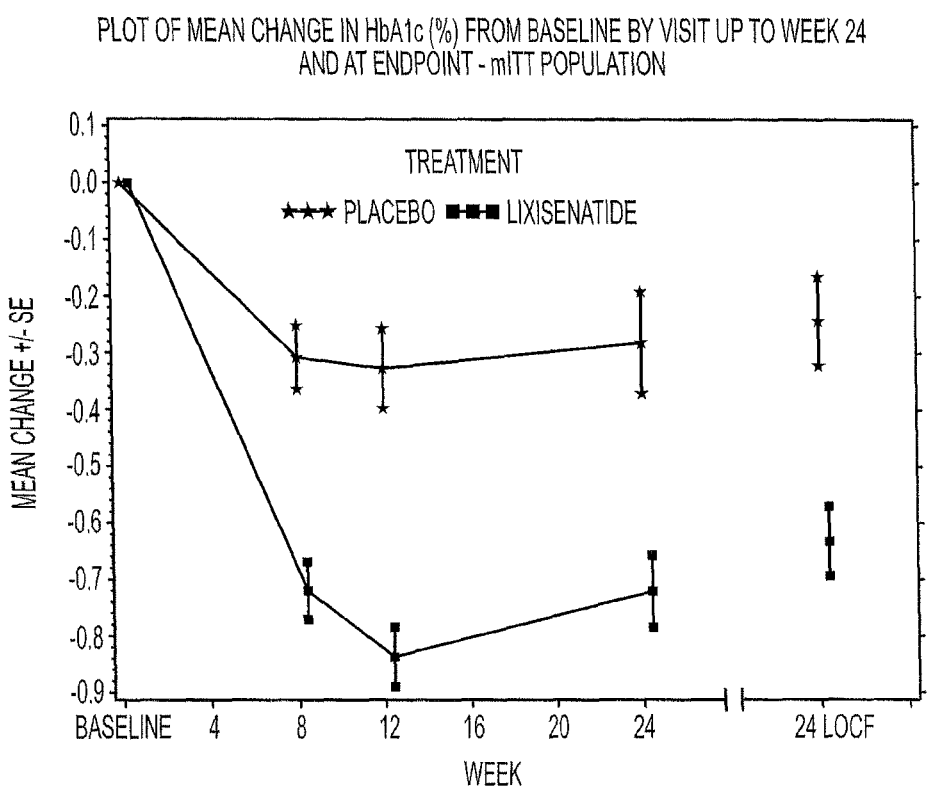
Figure 6:
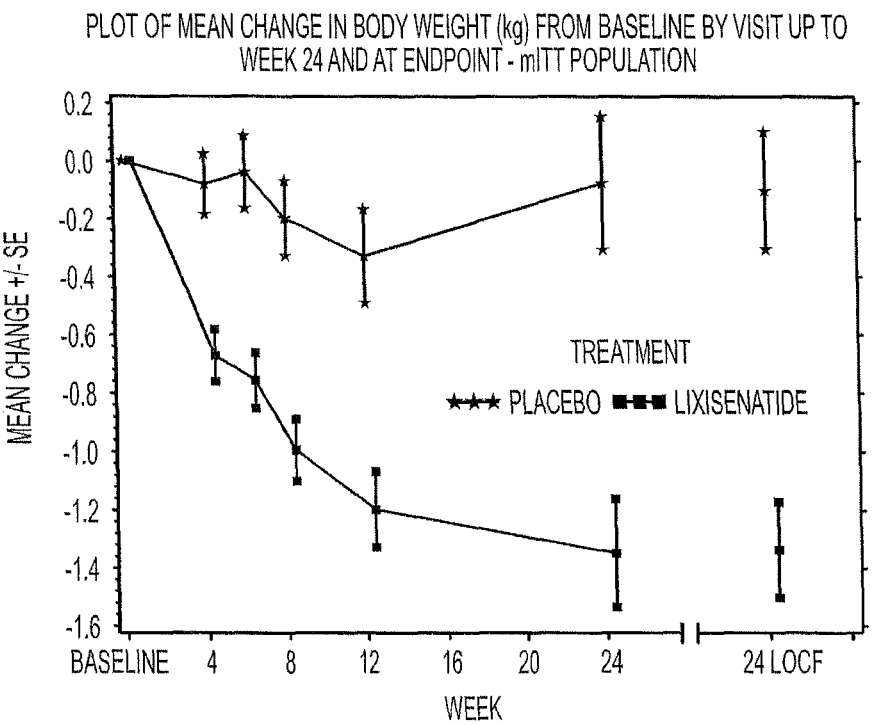
Figure 7:
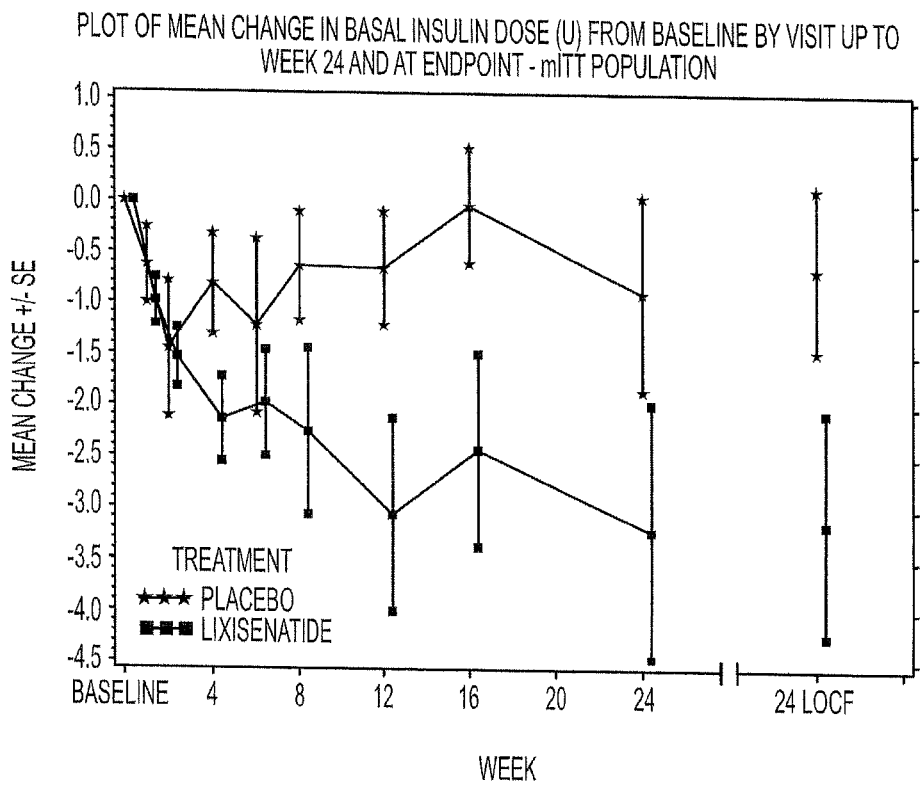

FIG. 2—Kaplan-Meier plot of time to treatment discontinuation due to any reason—Randomized population FIG. 3—Plot of mean change in HbA$_{1c}$ (%) from baseline by visit up to Week 24 and at endpoint—mITT FIG. 4—Plot of mean change in average 7-point Self Monitored Plasma Glucose (SMPG) (mmol/L) from baseline by visit up to Week 24 and at endpoint—mITT population FIG. 5—Plot of mean change in fasting plasma glucose (mmol/L) from baseline by visit up to Week 24 and at endpoint—mITT population FIG. 6—Plot of mean change in body weight (kg) from baseline by visit up to Week 24 and at endpoint—mITT population FIG. 7—Plot of mean change in basal insulin dose (U) from baseline by visit up to Week 24 and at endpoint—mITT population FIG. 8—Plot of mean change in HbA$_{1c}$ (%) from baseline by visit and at endpoint—mITT population FIG. 9—Plot of mean change in 2-hour postprandial plasma glucose (mmol/L) from baseline by visit and at endpoint—mITT population FIG. 10—Plot of mean change in average 7-point Self Monitored Plasma Glucose (SMPG) (mmol/L) from baseline by visit and at endpoint—mITT population FIG. 11—Plot of mean change in fasting plasma glucose (mmol/L) from baseline by visit and at endpoint—mITT population FIG. 12—Plot of mean change in body weight (kg) from baseline by visit and at endpoint—mITT population FIG. 13—Plot of mean change in basal insulin dose (U) from baseline by visit and at endpoint—mITT population

EXAMPLE

The Example refers to a randomized, double-blind, placebo-controlled, 2-arm, parallel-group, multinational study assessing the efficacy and safety of lixisenatide in comparison to placebo as an add-on treatment to basal insulin in combination with or without metformin in patients with type 2 diabetes.

The Example refers to a randomized, double-blind, placebo-controlled, 2-arm, parallel-group, multinational study assessing the efficacy and safety of lixisenatide in comparison to placebo as an add-on treatment to basal insulin in combination with or without metformin in patients with type 2 diabetes. The approximate minimum study duration per patient was 79 weeks (up to 3 weeks screening+24-week main treatment+variable extension+3 days follow-up). The study was conducted in 111 centers in 15 countries. The primary objective of the study was to assess the efficacy of lixisenatide on glycemic control in comparison to placebo in terms of $HbA_{1c}$ reduction (absolute change) over a period of 24 weeks.

A total of 496 patients were randomized to one of the two treatment groups (329 in the lixisenatide group and 167 in the placebo group) and 495 randomized patients were exposed to the investigational product (IP). Demographics and baseline characteristics were generally similar across the treatment groups. Four patients (2 on lixisenatide and 2 on placebo) were excluded from the mITT population for efficacy analyses due to lack of post-baseline efficacy data. During the whole-study treatment period, 115 (35.0%) lixisenatide-treated patients prematurely discontinued the IP, while 52 (31.1%) placebo-treated patients discontinued the IP. For both treatment groups, the main reason for treatment discontinuation was "other reasons" (15.8% for lixisenatide versus 13.2% for placebo) followed by "adverse events" (11.2% for lixisenatide versus 7.2% for placebo).

Efficacy analyses are based on the 24-week treatment: The least squared (LS) mean changes from baseline to Week 24 in $HbA_{1c}$ were −0.74% for the lixisenatide group and −0.38% for the placebo group (LS mean difference vs. placebo=−0.36%; p-value=0.0002). A total of 86 patients (28.3%) in the lixisenatide group achieved $HbA_{1c}$<7% at Week 24 compared to 19 patients (12.0%) in the placebo group, and 44 (14.5%) lixisenatide-treated patients had $HBA_{1c}$, ≤6.5% compared to 6 (3.8%) of placebo-treated patients. The $HbA_{1c}$ responder analysis ($HbA_{1c}$≤6.5 or <7% at Week 24) using Cochran-Mantel-Haenszel (CMH) method showed a significant treatment difference versus placebo for lixisenatide group at Week 24 (p-value=0.0003 and p-value<0.0001, respectively).

Treatment with lixisenatide also improved post-prandial glycemic control as shown by the results for the 2-hour post-prandial plasma glucose (PPG) and glucose excursion assessment. A statistically significant improvement in PPG after a test meal was demonstrated in the lixisenatide group, compared with the placebo group with a LS mean difference of −3.81 mmol/L (p-value<0.0001). Furthermore, treatment with lixisenatide demonstrated a statistically significant improvement in the average of the 7-point self-monitored plasma glucose (SMPG) profile (LS mean difference of −0.88 mmol/L; p-value<0.0001) compared with the placebo group. For fasting plasma glucose, no statistically significant difference was observed between the treatment groups (LS mean difference versus placebo=−0.08 mmol/L; p-value=0.7579). Patients treated with lixisenatide showed a statistically significant decrease in body weight (LS mean difference of −1.28 kg; p-value<0.0001) compared with the placebo group without an adjustment for multiplicity. A total of 30 patients (12 [7.3%] in the placebo group and 18 [5.5%] in the lixisenatide group) received a rescue therapy. While achieving a better glycemic control, patients treated with lixisenatide also showed a statistically significant decrease in daily basal insulin dose compared to the placebo-treated patients. (LS mean difference of −3.69 U, p-value=0.0120).

Safety analyses are based on the whole study treatment: Lixisenatide was well tolerated. The proportions of the patients with treatment emergent adverse events (TEAEs) were generally comparable between the two treatment groups (87.5% in the lixisenatide group versus 85.6% in the placebo group). Two patients in the lixisenatide group and two patients in the placebo group had TEAEs leading to death. The number of patients with serious TEAEs was 46 (14.0%) in the lixisenatide group and 17 (10.2%) in the placebo group. One hundred thirty-eight (42.1%) lixisenatide-treated patients had symptomatic hypoglycemic events as defined in the protocol during the on-treatment period, whereas 65 (38.9%) patients in the placebo group reported symptomatic hypoglycemia. Aside from hypoglycemia, the most frequently reported TEAE was nausea (29.3%) for the lixisenatide group and nasopharyngitis (12.6%) for the placebo group. Seven patients in the lixisenatide group (2.1%) and 1 patient in the placebo group (0.6%) experienced severe symptomatic hypoglycemia per the protocol definition. A total of 11 patients (8 [2.4%] lixisenatide-treated patients and 3 [1.8%] placebo-treated patients) reported 11 TEAEs adjudicated as an allergic reaction by the Allergic Reaction Assessment Committee (ARAC), and three of these events (2 events of anaphylactic reaction in the lixisenatide group and 1 angioedema in the placebo group) were adjudicated as possibly related to the IP. One lixisenatide-treated patient reported an event of pancreatitis, which was assessed as a recurrent pancreatitis and not related to the IP per the investigator.

OBJECTIVES

Primary Objective

The primary objective of this study was to assess the efficacy of lixisenatide on glycemic control in comparison to placebo as an add-on treatment to basal insulin in Type 2 Diabetes patients treated with basal insulin in terms of absolute HbA1c reduction over a period of 24 weeks.

Secondary Objective(s)

The secondary objectives of this study were:
To assess the effects of lixisenatide on:
Body weight,
2-hour postprandial plasma glucose after standardized meal challenge test,
Percentage of patients reaching HbA1c<7%,
Percentage of patients reaching HbA1c≤6.5%,
Fasting Plasma Glucose (FPG),
Change in 7-point Self Monitored Plasma Glucose (SMPG) profiles,
Change in basal insulin and total insulin doses.
To assess lixisenatide safety and tolerability.
To assess lixisenatide PK.
To assess anti-lixisenatide antibody development.

TRIAL DESIGN

This was a double-blind, randomized, placebo-controlled, 2-arm, parallel-group multinational study with an unbalanced 2:1 randomization ratio. The study was double-blind with regard to active and placebo treatments. The study drug volume (i.e., dose of active drug or matching placebo) was not blinded.

The patients were stratified by screening values of glycosylated hemoglobin $A_{1c}$ ($HbA_{1c}$) (<8%, ≥8%) and metformin use at screening (Yes, No). After a screening period, patients were centrally randomized via interactive voice response system (IVRS) in a 2:1 ratio to either lixisenatide or placebo.

The approximate minimum study duration per patient was 79 weeks (up to 3 weeks screening+24 weeks main double-blind treatment+variable extension+3 days follow-up). Patients who completed the 24-week main double-blind period underwent a variable double-blind extension period, which ended for all patients approximately at the scheduled date of week 76 visit (V25) for the last randomized patient.

Patients who prematurely discontinued the IP were continued in the study up to the scheduled date of study completion. They were followed up according to the study procedures as specified in the protocol amendment (except 3-day safety post-treatment follow-up, pharmacokinetics assessment, and meal challenge test).

Primary and Key Secondary Endpoints

Primary Endpoint

The primary efficacy variable was the absolute change in $HbA_{1c}$ from baseline to Week 24, which was defined as: $HbA_{1c}$ at Week 24–$HbA_{1c}$ at baseline.

If a patient discontinued the treatment prematurely or received rescue therapy during the main 24-week double-blind treatment period or did not have $HbA_{1c}$ value at Week 24 visit, the last post-baseline $HbA_{1c}$ measurement during the main 24-week double-blind on-treatment period was used as $HbA_{1c}$ value at Week 24 (Last Observation Carried Forward [LOCF] procedure).

Secondary Endpoints

Efficacy Endpoints

For secondary efficacy variables, the same procedure for handling missing assessment/early discontinuation was applied as for the primary variable.

Continuous Variables

Change in 2-hour postprandial plasma glucose (mmol/L) after a standardized meal from baseline to Week 24

Change in 7-point SMPG profiles (mmol/L) (ie, the average and each time point of the 7 points) from baseline to Week 24;

Change in FPG (mmol/L) from baseline to Week 24

Change in body weight (kg) from baseline to Week 24

Change in glucose excursion (2-hour postprandial plasma glucose—plasma glucose 30 minutes prior to the meal test before study drug administration) (mmol/L) after standardized meal challenge test from baseline to Week 24;

Change in daily basal insulin dose (U) and total insulin dose (U) from baseline to Week 24.

Categorical Variables

Percentage of patients with $HbA_{1c}$<7% at Week 24

Percentage of patients with $HbA_{1c}$≤6.5% at Week 24

Percentage of patients requiring rescue therapy during the main 24-week double-blind treatment period Percentage of patients with ≥5% weight loss (kg) from baseline to Week 24

Safety Endpoints

The safety analysis was based on the reported TEAEs and other safety information including symptomatic hypoglycemia and severe symptomatic hypoglycemia, local tolerability at injection site, allergic events (as adjudicated by ARAC), suspected pancreatitis, increased calcitonin, vital signs, 12-lead ECG and laboratory tests.

Major cardiovascular events were also collected and sent for adjudication by a Cardiovascular Adjudication Committee (CAC). The adjudicated and confirmed events by CAC from this study and other lixisenatide phase 3 studies will be pooled as necessary for analyses and summarized in a separate report based on the statistical analysis plan for the overall cardiovascular assessment of lixisenatide. The KRM/CSR will not present the summary of the adjudicated and confirmed CV events from this study.

SAMPLE SIZE CALCULATION ASSUMPTIONS

The sample size/power calculations were performed based on the primary variable, change from baseline to Week 24 in HbA1c.

Three hundred patients in the lixisenatide treatment and 150 in the placebo treatment arm were expected to provide a power of 96% (or 86%) to detect differences of 0.5% (or 0.4%) in the change from baseline to Week 24 in HbA1c between lixisenatide and placebo, assuming the common standard deviation (SD) was 1.3% with a 2-sided test at the 5% significance level.

STATISTICAL METHODS

Analysis Populations

The mITT population consists of all patients who were randomized, received at least one dose of double-blind IP, and had both a baseline assessment and at least one post-baseline assessment of any primary or secondary efficacy variables, irrespective of compliance with the study protocol and procedures.

The safety population was defined as all randomized patients who took at least one dose of the double-blind IP.

Primary Efficacy Analysis

The primary efficacy variable (change in $HbA_{1c}$ from baseline to Week 24) was analyzed using an analysis of covariance (ANCOVA) model with treatment, randomization strata of screening $HbA_{1c}$ (<8.0, ≥8.0%), randomization strata of metformin use at screening (Yes, No) and country as fixed effects and using the baseline value as a covariate. Difference between lixisenatide and placebo and two-sided 95% confidence interval as wells as p-value were estimated within the framework of ANCOVA.

The LOCF procedure was used by taking the last available post-baseline on-treatment $HbA_{1c}$ measurement (before the initiation of the new medication in the event of rescue therapy) as the $HbA_{1c}$ value at Week 24.

The primary analysis of the primary efficacy variable was performed based on the mITT population and the measurements obtained during the main 24-week double-blind on-treatment period for efficacy variables. The main 24-week double-blind on-treatment period for efficacy variables except those from the meal challenge test, 7-point SMPG, basal insulin dose and total insulin was defined as the time from the first dose of the double-blind IP up to 3 days (except for FPG by central laboratory, which was up to 1 day) after the last dose of the double-blind IP injection on or before V12/Week 24 visit (or D169 if V12/Week 24 visit was missing), or up to the introduction of the rescue therapy, whichever was the earliest. The main 24-week double-blind on-treatment period for efficacy variables from the meal challenge test including 2-hour PPG and glucose excursion, 7-point SMPG, basal insulin dose and total insulin was defined as the time from the first dose of the double-blind IP up to the date of the last dose of the double-blind IP injection on or before V12/Week 24 visit (or D169 if V12/Week 24 visit was missing), or up to the introduction of the rescue therapy, whichever was the earliest.

Secondary Efficacy Analysis

Once the primary variable was statistically significant at α=0.05, the testing procedure was performed to test the following secondary efficacy variables by the following prioritized order. The tests stop as soon as an endpoint was found not statistically significant at α=0.05.

Change in 2-hour postprandial plasma glucose (mmol/L) after a standardized meal test from baseline to Week 24,
Change in the average of the 7-point SMPG from baseline to Week 24,
Change in FPG (mmol/L) from baseline to Week 24,
Change in body weight (kg) from baseline to Week 24,
Percentage of patients requiring rescue therapy during the main 24-week double-blind treatment period.

No multiplicity adjustment will be made on the other secondary efficacy variables, which are not mentioned above.

All continuous secondary efficacy variables at Week 24 as described in Section 3.2.1 were analyzed using the similar approach and ANCOVA model as described above for the primary analysis of the primary efficacy endpoint. The estimates of the treatment mean difference between lixisenatide and placebo and two-sided 95% confidence intervals were provided.

The following categorical secondary efficacy variables at Week 24 were analyzed using a Cochran-Mantel-Haenszel (CMH) method stratified on randomization strata (screening $HbA_{1c}$ [<8.0, ≥8%] and metformin use at screening [Yes, No]):

Percentage of patients with $HbA_{1c}$<7.0% at Week 24,
Percentage of patients with $HbA_{1c}$≤6.5% at Week 24,
Percentage of patients requiring rescue therapy during the main 24-week double-blind treatment period.

Number and percentage of patients with ≥5% weight loss from baseline at Week 24 are presented by treatment groups.

All secondary endpoints at the end of treatment were only evaluated by descriptive statistics (mean, standard deviation, median and ranges provided in CSR).

Safety Analysis

The safety analyses were primarily based on the on-treatment period for the whole study. The on-treatment period for the whole study was defined as the time from the first dose of double-blind IP up to 3 days after the last dose of IP administration during the whole study period regardless of rescue status. The 3-day interval was chosen based on the half-life of the IP (approximately 5 times the half-life).

In addition, the safety analyses for the 24-week double-blind treatment period will be summarized in CSR.

The summary of safety results (descriptive statistics or frequency tables) is presented by treatment groups.

RESULTS

Study Patients

Patient Accountability

The study was conducted in 111 centers in 15 countries (Brazil, Canada, Chile, Egypt, France, Germany, India, Italy, Korea, Mexico, Puerto Rico, Russian Federation, Turkey, United Kingdom and United States). A total of 879 patients were screened and 496 were randomized to one of the two treatment groups. The main reason for screening failure was $HbA_{1c}$ value at the screening visit was out of the protocol defined range (205 [23.3%] out of 879 screened patients).

Of the 496 randomized patients, 495 were exposed to the IP. One patient from lixisenatide group was not exposed to the IP. Four patients (2 in the lixisenatide group and 2 in the placebo group) were excluded from mITT population for efficacy analyses due to lack of post-baseline efficacy data. Table 1 provides the number of patients included in each analysis population.

TABLE 1

| Analysis populations - Randomized population | | | |
|---|---|---|---|
| | Placebo | Lixisenatide | All |
| Randomized population | 167 (100%) | 329 (100%) | 496 (100%) |
| Efficacy population Modified Intent-to-Treat (mITT) | 165 (98.8%) | 326 (99.1%) | 491 (99.0%) |
| Safety population | 167 (100%) | 328 (99.1%) | 495 (99.8%) |

Note:
The Safety patients are tabulated according to treatment actually received (as treated). For the efficacy populations, patients are tabulated according to their randomized treatment (as randomized).

Study Disposition

Table 2 provides the summary of patient disposition for each treatment group.

During the whole-study treatment period, 115 (35.0%) lixisenatide-treated patients prematurely discontinued the IP, while 52 (31.1%) placebo-treated patients discontinued the IP. For both treatment groups, the main reason for treatment discontinuation was "other reasons" (52 patients [15.8%] for lixisenatide and 22 patients [13.2%] for placebo), mostly being personal reasons such as moving out of town, lost job, family issues or too busy to commit to the visit schedules, followed by "adverse events" (37 patients [11.2%] including 2 non-TEAEs for lixisenatide versus 12 patients [7.2%] for placebo).

For the 24-week main treatment period, 53 (16.1%) patients in lixisenatide group and 20 (12.0%) in placebo prematurely discontinued the IP with the main reason being adverse events (26 patients, 7.9%) for lixisenatide group and "other" (8 patients, 4.8%) for placebo group. The time-to-onset of treatment discontinuation due to any reason for the overall treatment period is depicted in FIG. 2. A higher discontinuation rate was observed for the lixisenatide group.

TABLE 2

| Patient disposition - Randomized population | | |
|---|---|---|
| | Placebo (N = 167) | Lixisenatide (N = 329) |
| Randomized and treated | 167 (100%) | 328 (99.7%) |
| Did not complete 24-week double-blind study treatment | 20 (12.0%) | 53 (16.1%) |
| Subject's request for 24-week treatment discontinuation | 15 (9.0%) | 46 (14.0%) |
| Reason for 24-week treatment discontinuation | 20 (12.0%) | 53 (16.1%) |
| Adverse event | 4 (2.4%) | 26 (7.9%) |
| Lack of efficacy | 3 (1.8%) | 3 (0.9%) |
| Poor compliance to protocol | 4 (2.4%) | 6 (1.8%) |
| Lost to follow-up | 1 (0.6%) | 0 |
| Other | 8 (4.8%) | 18 (5.5%) |
| Did not complete double-blind study treatment | 52 (31.1%) | 115 (35.0%) |
| Subject's request for treatment discontinuation | 41 (24.6%) | 93 (28.3%) |

TABLE 2-continued

Patient disposition - Randomized population

|  | Placebo (N = 167) | Lixisenatide (N = 329) |
|---|---|---|
| Reason for study treatment discontinuation | 52 (31.1%) | 115 (35.0%) |
| Adverse event | 12 (7.2%) | 37 (11.2%) |
| Lack of efficacy | 11 (6.6%) | 11 (3.3%) |
| Poor compliance to protocol | 6 (3.6%) | 13 (4.0%) |
| Lost to follow-up | 1 (0.6%) | 2 (0.6%) |
| Other | 22 (13.2%) | 52 (15.8%) |
| Status at last study contact | 167 (100%) | 329 (100%) |
| Alive | 163 (97.6%) | 320 (97.3%) |
| Lost to follow-up | 2 (1.2%) | 6 (1.8%) |
| Dead | 2 (1.2%) | 3 (0.9%) |

Note:
Percentages are calculated using the number of randomized patients as denominator.

Demographics and Baseline Characteristics

The demographic and patient baseline characteristics were generally similar between the two treatment groups for the safety population (Table 3). The median age of the study population was 58.0 years. The majority of the patients were Caucasian (77.6%). The lixisenatide group had more female patients in percentage (55.5% female and 44.5% male) than the placebo group (50.9% female and 49.1% male).

TABLE 3

Demographics and patient characteristics at screening or baseline - Safety population

|  | Placebo (N = 167) | Lixisenatide (N = 328) | All (N = 495) |
|---|---|---|---|
| Age (years) | | | |
| Number | 167 | 328 | 495 |
| Mean (SD) | 56.9 (9.8) | 57.4 (9.5) | 57.2 (9.6) |
| Median | 57.0 | 58.0 | 58.0 |
| Min:Max | 29:81 | 34:80 | 29:81 |
| Age Group (years) [n (%)] | | | |
| Number | 167 | 328 | 495 |
| <50 | 38 (22.8%) | 64 (19.5%) | 102 (20.6%) |
| ≥50 to < 65 | 93 (55.7%) | 194 (59.1%) | 287 (58.0%) |
| ≥65 to < 75 | 32 (19.2%) | 61 (18.6%) | 93 (18.8%) |
| ≥75 | 4 (2.4%) | 9 (2.7%) | 13 (2.6%) |
| Sex [n (%)] | | | |
| Number | 167 | 328 | 495 |
| Male | 82 (49.1%) | 146 (44.5%) | 228 (46.1%) |
| Female | 85 (50.9%) | 182 (55.5%) | 267 (53.9%) |
| Race [n (%)] | | | |
| Number | 167 | 328 | 495 |
| Caucasian/White | 130 (77.8%) | 254 (77.4%) | 384 (77.6%) |
| Black | 6 (3.6%) | 14 (4.3%) | 20 (4.0%) |
| Asian/Oriental | 30 (18.0%) | 53 (16.2%) | 83 (16.8%) |
| Other | 1 (0.6%) | 7 (2.1%) | 8 (1.6%) |
| Ethnicity [n (%)] | | | |
| Number | 167 | 328 | 495 |
| Hispanic | 40 (24.0%) | 94 (28.7%) | 134 (27.1%) |
| Non Hispanic | 127 (76.0%) | 234 (71.3%) | 361 (72.9%) |
| Screening HbA1c (%) | | | |
| Number | 167 | 328 | 495 |
| Mean (SD) | 8.46 (0.81) | 8.49 (0.83) | 8.48 (0.82) |
| Median | 8.50 | 8.50 | 8.50 |
| Min:Max | 7.0:10.0 | 7.0:10.0 | 7.0:10.0 |
| Randomization strata of screening HbA1c (%) [n (%)] | | | |
| Number | 167 | 328 | 495 |
| <8 | 51 (30.5%) | 98 (29.9%) | 149 (30.1%) |
| ≥8 | 116 (69.5%) | 230 (70.1%) | 346 (69.9%) |
| Randomization strata of metformin use at screening [n (%)] | | | |
| Number | 167 | 328 | 495 |
| Yes | 131 (78.4%) | 259 (79.0%) | 390 (78.8%) |
| No | 36 (21.6%) | 69 (21.0%) | 105 (21.2%) |

TABLE 3-continued

Demographics and patient characteristics at screening or baseline - Safety population

| | Placebo (N = 167) | Lixisenatide (N = 328) | All (N = 495) |
|---|---|---|---|
| Baseline BMI (kg/m$^2$) | | | |
| Number | 167 | 328 | 495 |
| Mean (SD) | 32.56 (6.32) | 31.91 (6.17) | 32.13 (6.22) |
| Median | 32.33 | 31.23 | 31.35 |
| Min:Max | 20.1:58.4 | 20.7:64.4 | 20.1:64.4 |
| Baseline BMI Categories (kg/m$^2$) [n (%)] | | | |
| Number | 167 | 328 | 495 |
| <30 | 61 (36.5%) | 137 (41.8%) | 198 (40.0%) |
| ≥30 | 106 (63.5%) | 191 (58.2%) | 297 (60.0%) |

BMI = Body Mass Index.

Disease characteristics including diabetic history were generally comparable between the two treatment groups (Table 4). One placebo-treated patient (#840608010) had Type 1 diabetes and was discontinued from the study shortly after the identification of the diagnosis.

The mean duration of basal insulin treatment for the study population was 3.11 years (Table 5). Majority of the patients took either long-acting insulin analogues (glargine 50.1%, detemir 8.7%) or NPH (40.0%) during screening and continued into the study treatment period with a few exceptions (1.6%) who took pre-mixed insulin instead. Eight patients (5 on lixisenatide and 3 on placebo) took pre-mixed insulin at screening and continued into the study. Two placebo-treated patients took two types of insulin (one on detemir+glargine and another on NPH+Novolin 70/30 mix) during screening and continued into the study. All insulin usage including pre-mixed insulin is displayed in Table 5.

Three hundreds and ninety-two patients (79.2%) were on metformin at the screening visit with a similar usage proportion in the two treatment groups (lixisenatide 79.6% and placebo 78.4%, (Table 6). There were two discrepancies in the number of patients between "randomization strata of metformin use at screening" and actual "metformin use at screening" due to randomization strata errors.

TABLE 4

Disease characteristics at screening or baseline - Safety population

| | Placebo (N = 167) | Lixisenatide (N = 328) | All (N = 495) |
|---|---|---|---|
| Duration of diabetes (years) | | | |
| Number | 167 | 328 | 495 |
| Mean (SD) | 12.43 (6.33) | 12.48 (7.04) | 12.46 (6.80) |
| Median | 11.39 | 11.43 | 11.39 |
| Min:Max | 2.3:34.8 | 1.0:41.6 | 1.0:41.6 |
| Age at onset of Type 2 diabetes (years) | | | |
| Number | 167 | 328 | 495 |
| Mean (SD) | 44.55 (9.16) | 44.85 (9.08) | 44.75 (9.10) |
| Median | 45.22 | 45.00 | 45.00 |
| Min:Max | 15.0:72.0 | 18.0:68.0 | 15.0:72.0 |
| History of gestational diabetes [n (%)] | | | |
| Number (Female) | 85 | 182 | 267 |
| Yes (Female) | 6 (7.1%) | 19 (10.4%) | 25 (9.4%) |
| No (Female) | 79 (92.9%) | 163 (89.6%) | 242 (90.6%) |
| Prior use of GLP-1 receptor agonist [n (%)] | | | |
| Number | 167 | 328 | 495 |
| Yes | 6 (3.6%) | 7 (2.1%) | 13 (2.6%) |
| No | 161 (96.4%) | 321 (97.9%) | 482 (97.4%) |
| Diabetic retinopathy [n (%)] | | | |
| Number | 167 | 328 | 495 |
| Yes | 33 (19.8%) | 66 (20.1%) | 99 (20.0%) |
| No | 132 (79.0%) | 251 (76.5%) | 383 (77.4%) |
| Unknown | 2 (1.2%) | 11 (3.4%) | 13 (2.6%) |

TABLE 4-continued

Disease characteristics at screening or baseline - Safety population

| | Placebo (N = 167) | Lixisenatide (N = 328) | All (N = 495) |
|---|---|---|---|
| Diabetic sensory or motor neuropathy [n (%)] | | | |
| Number | 167 | 328 | 495 |
| Yes | 50 (29.9%) | 99 (30.2%) | 149 (30.1%) |
| No | 116 (69.5%) | 225 (68.6%) | 341 (68.9%) |
| Unknown | 1 (0.6%) | 4 (1.2%) | 5 (1.0%) |
| Diabetic autonomic neuropathy [n (%)] | | | |
| Number | 167 | 328 | 495 |
| Yes | 9 (5.4%) | 8 (2.4%) | 17 (3.4%) |
| No | 156 (93.4%) | 314 (95.7%) | 470 (94.9%) |
| Unknown | 2 (1.2%) | 6 (1.8%) | 8 (1.6%) |
| Diabetic nephropathy [n (%)] | | | |
| Number | 167 | 328 | 495 |
| Yes | 15 (9.0%) | 31 (9.5%) | 46 (9.3%) |
| Microalbuminuria | 6 (3.6%) | 21 (6.4%) | 27 (5.5%) |
| Overt proteinuria | 2 (1.2%) | 1 (0.3%) | 3 (0.6%) |
| Impaired renal function | 3 (1.8%) | 1 (0.3%) | 4 (0.8%) |
| Dialysis or transplantation | 0 | 0 | 0 |
| No | 150 (89.8%) | 291 (88.7%) | 441 (89.1%) |
| Unknown | 2 (1.2%) | 6 (1.8%) | 8 (1.6%) |
| Categorized albuminuria at randomization [n (%)] | | | |
| Number | 36 | 56 | 92 |
| <3 mg/L (Not reportable) | 3 (8.3%) | 5 (8.9%) | 8 (8.7%) |
| ≥3 mg/L (Reportable) | 33 (91.7%) | 51 (91.1%) | 84 (91.3%) |
| <20 mg/L | 17 (47.2%) | 26 (46.4%) | 43 (46.7%) |
| ≥20-<200 mg/L | 10 (27.8%) | 19 (33.9%) | 29 (31.5%) |
| ≥200 mg/L | 6 (16.7%) | 6 (10.7%) | 12 (13.0%) |
| Creatinine clearance at screening (ml/min) | | | |
| Number | 167 | 326 | 493 |
| Mean (SD) | 119.16 (45.81) | 118.05 (45.05) | 118.43 (45.27) |
| Median | 108.66 | 109.13 | 109.03 |
| Min:Max | 22.8:329.6 | 32.4:358.2 | 22.8:358.2 |
| Creatinine clearance categories at screening [n (%)] | | | |
| Number | 167 | 326 | 493 |
| <30 ml/min (severe renal impairment) | 1 (0.6%) | 0 | 1 (0.2%) |
| ≥30-<50 ml/min (moderate renal impairment) | 2 (1.2%) | 4 (1.2%) | 6 (1.2%) |
| ≥50-<80 ml/min (mild renal impairment) | 22 (13.2%) | 51 (15.6%) | 73 (14.8%) |
| >80 ml/min (no renal impairment) | 142 (85.0%) | 271 (83.1%) | 413 (83.8%) |

GLP-1 = Glucagon like peptide-1.
Creatinine clearance value is derived using the equation of Cockroft and Gault.

TABLE 5

Diabetes history - Basal insulin at screening - Safety population

| | Placebo (N = 167) | Lixisenatide (N = 328) | All (N = 495) |
|---|---|---|---|
| Duration of treatment with basal insulin (years) | | | |
| Number | 167 | 328 | 495 |
| Mean (SD) | 3.20 (3.96) | 3.06 (3.37) | 3.11 (3.57) |
| Median | 1.67 | 1.80 | 1.75 |
| Min:Max | 0.2:21.4 | 0.2:20.4 | 0.2:21.4 |

TABLE 5-continued

Diabetes history - Basal insulin at screening - Safety population

|  | Placebo (N = 167) | Lixisenatide (N = 328) | All (N = 495) |
|---|---|---|---|
| Insulin at screening | | | |
| Number | 167 | 328 | 495 |
| Glargine | 83 (49.7%) | 165 (50.3%) | 248 (50.1%) |
| Detemir | 19 (11.4%) | 24 (7.3%) | 43 (8.7%) |
| NPH[1] | 64 (38.3%) | 134 (40.9%) | 198 (40.0%) |
| Lente | 0 | 0 | 0 |
| Ultralente | 0 | 0 | 0 |
| Premix(Mixed insulin)[2,3] | 3 (1.8%) | 5 (1.5%) | 8 (1.6%) |
| Regimen at screening | | | |
| Number | 167 | 328 | 495 |
| Morning | 25 (15.0%) | 54 (16.5%) | 79 (16.0%) |
| Evening | 67 (40.1%) | 137 (41.8%) | 204 (41.2%) |
| Morning and evening | 75 (44.9%) | 137 (41.8%) | 212 (42.8%) |
| Daily dose at screening | | | |
| Total | | | |
| Number | 167 | 328 | 495 |
| Mean (SD) | 57.55 (34.72) | 53.95 (34.08) | 55.16 (34.31) |
| Median | 46.00 | 42.00 | 44.00 |
| Min:Max | 0.0:200.0 | 0.0[4]:400.0 | 0.0[4]:400.0 |
| Glargine | | | |
| Number | 83 | 165 | 248 |
| Mean (SD) | 61.60 (36.77) | 56.53 (39.47) | 58.23 (38.59) |
| Median | 48.00 | 43.00 | 45.00 |
| Min:Max | 30.0:190.0 | 0.0:400.0 | 0.0:400.0 |
| Detemir | | | |
| Number | 19 | 24 | 43 |
| Mean (SD) | 72.53 (49.52) | 57.29 (37.75) | 64.02 (43.47) |
| Median | 60.00 | 40.00 | 44.00 |
| Min:Max | 30.0:200.0 | 25.0:150.0 | 25.0:200.0 |
| NPH[1] | | | |
| Number | 64 | 134 | 198 |
| Mean (SD) | 45.78 (16.83) | 47.42 (19.92) | 46.89 (18.95) |
| Median | 40.00 | 40.00 | 40.00 |
| Min:Max | 30.0:100.0 | 20.0:140.0 | 20.0:140.0 |
| Premix(Mixed insulin)[2,3] | | | |
| Number | 3 | 5 | 8 |
| Mean (SD) | 63.33 (65.06) | 127.60 (33.81) | 103.50 (54.49) |
| Median | 60.00 | 110.00 | 106.00 |
| Min:Max | 0.0:130.0 | 100.0:176.0 | 0.0:176.0 |

[1] NPH included Isophand insulin and Insulin human injection, isophane.
[2] Protocol deviation.
[3] Pre-mixed insulin included Novolin 70/30 mix and Humalog 75/25 mix.
[4] Two patients (840612006 lixisenatide and 630625001 placebo) did not take their basal insulin on the date of screening.

TABLE 6

Disease characteristics - Metformin at screening or baseline - Safety population

|  | Placebo (N = 167) | Lixisenatide (N = 328) | All (N = 495) |
|---|---|---|---|
| Metformin use at screening [n (%)] | | | |
| Number | 167 | 328 | 495 |
| Yes | 131 (78.4%) | 261 (79.6%) | 392 (79.2%) |
| No | 36 (21.6%) | 67 (20.4%) | 103 (20.8%) |
| Duration of metformin treatment (years) | | | |
| Number | 131 | 260 | 391 |
| Mean (SD) | 6.47 (4.89) | 7.01 (5.94) | 6.83 (5.61) |
| Median | 4.84 | 5.74 | 5.40 |
| Min:Max | 0.3:23.1 | 0.1:29.5 | 0.1:29.5 |

TABLE 6-continued

Disease characteristics - Metformin at screening or baseline - Safety population

|  | Placebo (N = 167) | Lixisenatide (N = 328) | All (N = 495) |
|---|---|---|---|
| Daily dose of metformin at baseline (mg) |  |  |  |
| Number | 131 | 261 | 392 |
| Mean (SD) | 2008.02 (441.88) | 1961.02 (459.07) | 1976.72 (453.38) |
| Median | 2000.00 | 2000.00 | 2000.00 |
| Min:Max | 1000.0:3000.0 | 850.0:4200.0 | 850.0:4200.0 |
| Categorized daily dose of metformin at baseline (mg) [n (%)] |  |  |  |
| Number | 131 | 261 | 392 |
| <1500 | 2 (1.5%) | 9 (3.4%) | 11 (2.8%) |
| ≥1500-<2500 | 98 (74.8%) | 203 (77.8%) | 301 (76.8%) |
| ≥2500-<3000 | 22 (16.8%) | 32 (12.3%) | 54 (13.8%) |
| ≥3000 | 9 (6.9%) | 17 (6.5%) | 26 (6.6%) |

Basline efficacy variables including $HbA_{1c}$ were generally comparable between two treatment groups for the safety population (Table 7).

TABLE 7

Baseline efficacy variables - Safety population

|  | Placebo (N = 167) | Lixisenatide (N = 328) | All (N = 495) |
|---|---|---|---|
| HbA1c (%) |  |  |  |
| Number | 167 | 3258 | 495 |
| Mean (SD) | 8.37 (0.84) | 8.42 (0.88) | 8.40 (0.87) |
| Median | 8.40 | 8.40 | 8.40 |
| Min:Max | 6.7:10.5 | 6.0:10.8 | 6.0:10.8 |
| Weight (kg) |  |  |  |
| Number | 167 | 328 | 495 |
| Mean (SD) | 88.94 (20.84) | 87.10 (20.01) | 87.72 (20.29) |
| Median | 86.00 | 84.95 | 85.40 |
| Min:Max | 50.2:160.5 | 46.5:157.8 | 46.5:160.5 |
| FPG (mmol/L) |  |  |  |
| Number | 167 | 328 | 495 |
| Mean (SD) | 8.05 (2.65) | 8.13 (2.83) | 8.10 (2.76) |
| Median | 7.60 | 7.90 | 7.80 |
| Min:Max | 2.6:15.5 | 2.5:23.9 | 2.5:23.9 |
| 2-hour postprandial plasma glucose (mmol/L) |  |  |  |
| Number | 153 | 302 | 455 |
| Mean (SD) | 16.11 (3.86) | 16.47 (4.30) | 16.35 (4.15) |
| Median | 16.10 | 16.40 | 16.30 |
| Min:Max | 4.5:27.1 | 5.6:29.3 | 4.5:29.3 |
| Glucose excursion (mmol/L) |  |  |  |
| Number | 153 | 301 | 454 |
| Mean (SD) | 7.32 (3.43) | 7.59 (3.60) | 7.50 (3.54) |
| Median | 7.20 | 7.70 | 7.50 |
| Min:Max | −4.7:15.5 | −1.9:17.8 | −4.7:17.8 |
| Average 7-point SMPG (mmol/L) |  |  |  |
| Number | 155 | 301 | 456 |
| Mean (SD) | 10.58 (2.69) | 10.76 (2.61) | 10.70 (2.64) |
| Median | 10.16 | 10.53 | 10.45 |
| Min:Max | 6.8:23.4 | 5.3:21.4 | 5.3:23.4 |
| Basal insulin dose (U) |  |  |  |
| Number | 167 | 328 | 495 |
| Mean (SD) | 57.73 (34.54) | 53.43 (33.89) | 54.88 (34.14) |
| Median | 46.00 | 41.00 | 42.00 |
| Min:Max | 30.0:200.0 | 20.0:400.0 | 20.0:400.0 |
| Total insulin dose (U) |  |  |  |
| Number | 167 | 328 | 495 |
| Mean (SD) | 57.73 (34.54) | 53.43 (33.89) | 54.88 (34.14) |
| Median | 46.00 | 41.00 | 42.00 |
| Min:Max | 30.0:200.0 | 20.0:400.0 | 20.0:400.0 |

FPG = Fasting Plasma Glucose.
SMPG = Self-Monitored Blood Glucose.
Glucose excursion = 2-hour postprandial plasma glucose − plasma glucose 30 minutes prior to the meal test before study drug administration.

Dosage and Duration

The average treatment exposure was 491.5 days (70.2 weeks) for the lixisenatide group and 510.4 days (72.9 weeks) for the placebo group (Table 8). Of the 495 patients, 270 (82.3%) patients in the lixisenatide group and 146 (87.4%) patients in the placebo group received at least 169 days (24 weeks) of treatment; moreover, 171 (52.1%) patients in the lixisenatide group and 89 (53.3%) patients in the placebo group had at least 547 days (18 months) of treatment. Six patients (3 for lixisenatide and 3 for placebo) had a missing last administration date; of them, three were lost to follow-up (2 for lixisenatide and 1 for placebo) and hence their treatment durations were set to missing following the SAP data handling convention.

For the lixisenatide group, 286 (87.2%) patients were at the target total daily dose of 20 µg both at the end of the 24-week double-blind treatment period and at the end of whole double-blind treatment (Tables 9 and 10). For the placebo group, 161 (96.4%) patients and 162 (97.0%) patients were at the target total daily dose of 20 µg at the end of 24-week double-blind treatment period and at the end of whole double-blind treatment, respectively (Tables 9 and 10).

TABLE 8

Exposure - Safety population

|  | Placebo (N = 167) | Lixisenatide (N = 328) |
|---|---|---|
| Cumulative duration of treatment exposure (patient years) | 229.2 | 437.4 |
| Duration of study treatment (days) | | |
| Number | 164 | 325 |
| Mean (SD) | 510.4 (210.6) | 491.5 (233.9) |
| Median | 559.0 | 560.0 |
| Min:Max | 1:817 | 1:875 |
| Duration of study treatment by category [n (%)] | | |
| Missing duration | 3 (1.8%) | 3 (0.9%) |
| 1-14 days | 3 (1.8%) | 12 (3.7%) |
| 15-28 days | 3 (1.8%) | 9 (2.7%) |
| 29-56 days | 4 (2.4%) | 9 (2.7%) |
| 57-84 days | 3 (1.8%) | 9 (2.7%) |
| 85-168 days | 5 (3.0%) | 16 (4.9%) |
| 169-364 days | 11 (6.6%) | 25 (7.6%) |
| 365-546 days | 46 (27.5%) | 74 (22.6%) |
| 547-728 days | 72 (43.1%) | 137 (41.8%) |
| >728 days | 17 (10.2%) | 34 (10.4%) |
| Cumulative duration of study treatment by category [n (%)] | | |
| Missing duration | 3 (1.8%) | 3 (0.9%) |
| ≥1 day | 164 (98.2%) | 325 (99.1%) |
| ≥15 days | 161 (96.4%) | 313 (95.4%) |
| ≥29 days | 158 (94.6%) | 304 (92.7%) |
| ≥57 days | 154 (92.2%) | 295 (89.9%) |
| ≥85 days | 151 (90.4%) | 286 (87.2%) |
| ≥169 days | 146 (87.4%) | 270 (82.3%) |
| ≥365 days | 135 (80.8%) | 245 (74.7%) |
| ≥547 days | 89 (53.3%) | 171 (52.1%) |
| ≥729 days | 17 (10.2%) | 34 (10.4%) |

Duration of exposure = (date of the last double-blind investigational product injection – date of the first double-blind investigational product injection) + 1.

TABLE 9

Number (%) of patients by dose at the end of titration -Safety population

| Dose at the end of titration | Placebo (N = 167) | Lixisenatide (N = 328) |
|---|---|---|
| 10 μg | 2 (1.2%) | 16 (4.9%) |
| 15 μg | 10 (6.0%) | 31 (9.5%) |
| 20 μg | 155 (92.8%) | 281 (85.7%) |

Dose = Dose of active drug or volume-matched placebo.
The scheduled visit for end of titration per protocol would be Visit 5/Week 2.
Note:
Percentages are calculated using the number of safety patients as the denominator.

TABLE 10

Number (%) of patients by final total daily dose at the end of the 24-week treatment - Safety population

| Dose at the end of the 24-week | Placebo (N = 167) | Lixisenatide (N = 328) |
|---|---|---|
| 10 μg | 2 (1.2%) | 25 (7.6%) |
| 15 μg | 4 (2.4%) | 17 (5.2%) |
| 20 μg | 161 (96.4%) | 286 (87.2%) |

Dose = Dose of active drug or volume-matched placebo.
Note:
Percentages are calculated using the number of safety patients as the denominator.

TABLE 11

Number (%) of patients by final total daily dose at the end of the treatment - Safety population

| Final Dose | Placebo (N = 167) | Lixisenatide (N = 328) |
|---|---|---|
| 10 μg | 2 (1.2%) | 23 (7.0%) |
| 15 μg | 3 (1.8%) | 19 (5.8%) |
| 20 μg | 162 (97.0%) | 286 (87.2%) |

Dose = Dose of active drug or volume-matched placebo.
Note:
Percentages are calculated using the number of safety patients as the denominator.

Efficacy
Primary Efficacy Endpoint
Main Analysis table 11 summarizes the results of the primary efficacy parameter, change from baseline to Week 24 (LOCF) in $HbA_{1c}$ using an ANCOVA analysis.

The pre-specified primary analysis showed that treatment with lixisenatide resulted in a statistically significant decrease in $HbA_{1c}$ from Baseline to Week 24, compared with the placebo group (LS mean difference versus the placebo group=−0.36%; p-value=0.0002).

TABLE 12

Mean change in $HbA_{1c}$ (%) from baseline to Week 24 - mITT population

| HbA1c (%) | Placebo (N = 165) | Lixisenatide (N = 326) |
|---|---|---|
| Baseline | | |
| Number | 158 | 304 |
| Mean (SD) | 8.38 (0.83) | 8.39 (0.86) |
| Median | 8.40 | 8.40 |
| Min:Max | 6.8:10.5 | 6.0:10.8 |
| Week 24 (LOCF) | | |
| Number | 158 | 304 |
| Mean (SD) | 8.13 (1.17) | 7.76 (1.18) |
| Median | 7.90 | 7.60 |
| Min:Max | 6.0:11.6 | 5.6:14.1 |
| Change from baseline to Week 24 (LOCF) | | |
| Number | 158 | 304 |
| Mean (SD) | −0.24 (0.98) | −0.63 (1.08) |
| Median | −0.30 | −0.60 |
| Min:Max | −2.7:2.7 | −3.5:5.7 |
| LS Mean (SE)[a] | −0.38 (0.107) | −0.74 (0.090) |
| LS Mean difference (SE) vs. placebo[a] | — | −0.36 (0.096) |
| 95% CI | — | (−0.550 to −0.174) |
| p-value | — | 0.0002 |

LOCF = Last observation carried forward.
[a]Analysis of covariance (ANCOVA) model with treatment groups (lixisenatide and placebo), randomization strata of screening HbA1c (<8.0, ☐8.0%), randomization strata of metformin use at screening (Yes, No), country as fixed effects and baseline HbA1c value as a covariate.
The analysis included measurements obtained before the introduction of rescue medication and up to 3 days after the last dose of the double-blind investigational product injection on or before Visit 12 (Week 24), or Day 169 if Visit 12 (Week 24) is not available. Patients with both baseline and Week 24 (LOCF) measurements are included.

Table 13 summarizes the proportion of patients with treatment response in $HbA_{1c} \leq 6.5\%$ or <7% at Week 24, respectively. The analysis of $HbA_{1c}$ responders using the CMH method showed a significant treatment difference versus placebo for the lixisenatide-treated group (p-value=0.0003 and p-value<0.0001, respectively) for both categories. At Week 24, 14.5% of lixisenatide-treated patients and 3.8% of placebo-treated patients had achieved $HbA_{1c}$ values≤6.5%; 28.3% of patients in the lixisenatide group and 12.0% of patients in the placebo group had achieved $HbA_{1c}$ values<7%.

TABLE 13

Number (%) of patients with HbA$_{1c}$ value ≤6.5% or <7% respectively at Week 24 - mITT population

| HbA1c (%) | Placebo (N = 165) | Lixisenatide (N = 326) |
|---|---|---|
| Number | 158 | 304 |
| ≤6.5% | 6 (3.8%) | 44 (14.5%) |
| >6.5% | 152 (96.2%) | 260 (85.5%) |
| p-value vs. placebo[a] | — | 0.0003 |
| Number | 158 | 304 |
| <7.0% | 19 (12.0%) | 86 (28.3%) |
| ≥7.0% | 139 (88.0%) | 218 (71.7%) |
| p-value vs. placebo[a] | — | <0.0001 |

[a]Cochran-Mantel-Haenszel (CMH) method stratified by randomization strata of screening HbA1c (<8.0 or ≥8.0%) and randomization strata of metformin use at screening (Yes or No).
The analysis included measurements obtained before the introduction of rescue medication and up to 3 days after the last dose of the double-blind investigational product injection on or before Visit 12 (Week 24), or Day 169 if Visit 12 (Week 24) is not available.

Secondary Efficacy Endpoints

Table 14-18, and Table 20-21 summarize the ANCOVA analyses of 2-hour post-prandial plasma glucose, average 7-point SMPG, FPG, body weight, basal insulin, and glucose excursion respectively. FIG. 4-7 illustrate the Mean (±SE) change from baseline in average 7-point SMPG, FPG, body weight, and basal insulin over time during the main 24 week double-blind treatment period. FIG. 9-13 in the appendix illustrate the Mean (±SE) change from baseline in 2-hour post-prandial plasma glucose, average 7-point SMPG, FPG, body weight, and basal insulin over time up to Week 76.

The results of the 2-hour post-prandial plasma glucose after a test meal showed a statistically significant improvement from baseline to Week 24 in lixisenatide group compared with the placebo group (LS mean difference versus placebo=−3.81 mmol/L; p-value<0.0001). More over, treatment with lixisenatide substantially decreased post-prandial plasma glucose excursion from Baseline to Week 24 compared with the placebo group (LS mean difference=−3.80 mmol/L, 95% CI=−4.57 to −3.03) (Table 21).

For the average 7-point SMPG, a statistically significant improvement from baseline to Week 24 was observed in lixisenatide group compared with the placebo group (LS mean difference versus placebo=−0.88 mmol/L; p-value<0.0001) (Table 15). Patients in both treatment groups showed a modest decrease in FPG from baseline to Week 24 (LSmean −0.63 for lixisenatide versus −0.55 for placebo) with no statistically significant difference observed between the lixisenatide and placebo group (LS mean difference versus placebo=−0.08 mmol/L; p-value=0.7579) (Table 16).

As per the testing strategy adjusting for multiplicity, inferential testing for body weight loss from baseline at Week 24 and the percentages of patients requiring rescue therapy at Week 24 were exploratory since the preceding test (FPG) failed to show statistically significant group difference.

The LS mean body weight loss from baseline to Week 24 was −1.80 kg for the lixisenatide-treated patients and −0.52 kg for the placebo-treated patients, with statistically significant difference observed between the two treatment groups (LS mean difference versus placebo=−1.28 kg, p-value<0.0001) without an adjustment for multiplicity (Table 17). More lixisenatide-treated patients (13.2%) than placebo-treated patients (3.1%) had a weight loss of 5% or more from baseline to Week 24 (Table 18).

The percentages of patients requiring rescue therapy at Week 24 was slightly lower in the lixisenatide group than in the placebo group (18 patients [5.5%] in the lixisenatide group and 12 patients [7.3%] in the placebo group) (Table 19).

While achieving a greater HbA1C reduction, patients in lixisenatide group showed a steady reduction in daily basal insulin dose over the treatment period (FIG. 7) and reached a statistically significant decrease in mean change at the endpoint (Week 24) compared to the placebo group (LS mean difference versus placebo=−3.09 U; p-value=0.0412) (Table 20). The results from the analysis of the change in "total insulin dose" (not shown) are identical to those from the analysis on "basal insulin dose" due to the fact that the rescue insulin usage was excluded from the analysis.

TABLE 14

Mean change in 2-hour postprandial plasma glucose (mmol/L) from baseline to Week 24 - mITT population

| 2-hour post-prandial plasma glucose (mmol/L) | Placebo (N = 165) | Lixisenatide (N = 326) |
|---|---|---|
| Baseline | | |
| Number | 123 | 235 |
| Mean (SD) | 15.85 (3.71) | 16.44 (4.29) |
| Median | 15.60 | 16.30 |
| Min:Max | 4.5:25.2 | 5.6:29.3 |
| Week 24 (LOCF) | | |
| Number | 123 | 235 |
| Mean (SD) | 14.73 (3.61) | 11.04 (4.38) |
| Median | 14.40 | 10.80 |
| Min:Max | 5.8:28.7 | 3.0:24.4 |
| Change from baseline to Week 24 (LOCF) | | |
| Number | 123 | 235 |
| Mean (SD) | −1.13 (4.10) | −5.40 (5.76) |
| Median | −1.40 | −5.30 |
| Min:Max | −12.3:8.9 | −23.3:13.1 |
| LS Mean (SE)[a] | −1.72 (0.543) | −5.54 (0.468) |
| LS Mean difference (SE) vs. placebo[a] | — | −3.81 (0.451) |
| 95% CI | — | (−4.699 to −2.925) |
| p-value | — | <.0001 |

LOCF = Last observation carried forward.
[a]Analysis of covariance (ANCOVA) model with treatment groups (lixisenatide and placebo), randomization strata of screening HbA1c (<8.0, ☐8.0%), randomization strata of metformin use at screening (Yes, No), country as fixed effects and baseline 2-hour postprandial plasma glucose value as a covariate.
The analysis included measurements obtained before the introduction of rescue medication and up to the date of the last dose of the double-blind investigational product injection on or before Visit 12 (Week 24), or Day 169 if Visit 12 (Week 24) is not available. Patients with both baseline and Week 24 (LOCF) measurements are included.

TABLE 15

Mean change in average 7-point Self Monitored Plasma Glucose (SMPG) (mmol/L) from baseline to Week 24 - mITT population

| Average 7-point SMPG (mmol/L) | Placebo (N = 165) | Lixisenatide (N = 326) |
|---|---|---|
| Baseline | | |
| Number | 153 | 294 |
| Mean (SD) | 10.57 (2.69) | 10.74 (2.57) |
| Median | 10.16 | 10.53 |
| Min:Max | 6.8:23.4 | 5.3:21.4 |
| Week 24 (LOCF) | | |
| Number | 153 | 294 |
| Mean (SD) | 10.19 (2.44) | 9.39 (2.39) |

TABLE 15-continued

Mean change in average 7-point Self Monitored Plasma Glucose (SMPG) (mmol/L) from baseline to Week 24 - mITT population

| Average 7-point SMPG (mmol/L) | Placebo (N = 165) | Lixisenatide (N = 326) |
|---|---|---|
| Median | 9.74 | 9.17 |
| Min:Max | 5.9:21.7 | 5.2:20.6 |
| Change from baseline to Week 24 (LOCF) | | |
| Number | 153 | 294 |
| Mean (SD) | −0.37 (2.55) | −1.35 (2.86) |
| Median | −0.36 | −1.12 |
| Min:Max | −11.2:5.0 | −9.7:8.4 |
| LS Mean (SE)[a] | −0.61 (0.238) | −1.49 (0.201) |
| LS Mean difference (SE) vs. placebo[a] | — | −0.88 (0.219) |
| 95% CI | — | (−1.312 to −0.449) |
| p-value | — | <.0001 |

LOCF = Last observation carried forward.

[a]Analysis of covariance (ANCOVA) model with treatment groups (lixisenatide and placebo), randomization strata of screening HbA1c (<8.0, ☐8.0%), randomization strata of metformin use at screening (Yes, No), country as fixed effects and baseline average 7-point SMPG value as a covariate.
The analysis included measurements obtained before the introduction of rescue medication and up to the date of the last dose of the double-blind investigational product injection on or before Visit 12 (Week 24), or Day 169 if Visit 12 (Week 24) is not available. Patients with both baseline and Week 24 (LOCF) measurements are included.

TABLE 16

Mean change in fasting plasma glucose (mmol/L) from baseline to Week 24 - mITT population

| Fasting plasma glucose (mmol/L) | Placebo (N = 165) | Lixisenatide (N = 326) |
|---|---|---|
| Baseline | | |
| Number | 163 | 317 |
| Mean (SD) | 8.03 (2.65) | 8.11 (2.84) |
| Median | 7.60 | 7.90 |
| Min:Max | 2.6:15.5 | 2.5:23.9 |
| Week 24 (LOCF) | | |
| Number | 163 | 317 |
| Mean (SD) | 8.02 (2.66) | 7.96 (2.97) |
| Median | 7.60 | 7.40 |
| Min:Max | 2.7:15.5 | 3.1:26.6 |
| Change from baseline to Week 24 (LOCF) | | |
| Number | 163 | 317 |
| Mean (SD) | −0.00 (3.07) | −0.16 (3.41) |
| Median | 0.00 | −0.10 |
| Min:Max | −8.6:8.8 | −12.3:18.3 |
| LS Mean (SE)[a] | −0.55 (0.281) | −0.63 (0.233) |
| LS Mean difference (SE) vs. placebo[a] | — | −0.08 (0.259) |
| 95% CI | — | (−0.590 to 0.430) |
| p-value | — | 0.7579 |

LOCF = Last observation carried forward.
[a]Analysis of covariance (ANCOVA) model with treatment groups (lixisenatide and placebo), randomization strata of screening HbA1c (<8.0, ☐8.0%), randomization strata of metformin use at screening (Yes, No), country as fixed effects and baseline fasting plasma glucose as a covariate.
The analysis included measurements obtained before the introduction of rescue medication and up to 1 day after the last dose of the double-blind investigational product injection on or before Visit 12 (Week 24), or Day 169 if Visit 12 (Week 24) is not available. Patients with both baseline and Week 24 (LOCF) measurements are included.

TABLE 17

Mean change in body weight (kg) from baseline to Week 24 - mITT population

| Body weight (kg) | Placebo (N = 165) | Lixisenatide (N = 326) |
|---|---|---|
| Baseline | | |
| Number | 161 | 311 |
| Mean (SD) | 89.11 (21.00) | 87.39 (20.00) |
| Median | 85.90 | 85.70 |
| Min:Max | 50.2:160.5 | 46.5:157.8 |
| Week 24 (LOCF) | | |
| Number | 161 | 311 |
| Mean (SD) | 89.01 (20.86) | 86.05 (19.84) |
| Median | 84.50 | 84.00 |
| Min:Max | 52.0:160.0 | 46.0:158.5 |
| Change from baseline to Week 24 (LOCF) | | |
| Number | 161 | 311 |
| Mean (SD) | −0.10 (2.57) | −1.33 (2.90) |
| Median | 0.00 | −1.00 |
| Min:Max | −10.9:9.4 | −11.5:6.7 |
| LS Mean (SE)[a] | −0.52 (0.293) | −1.80 (0.246) |
| LS Mean difference (SE) vs. placebo[a] | — | −1.28 (0.269) |
| 95% CI | — | (−1.803 to −0.747) |
| p-value | — | <.0001 |

LOCF = Last observation carried forward.

[a]Analysis of covariance (ANCOVA) model with treatment groups (lixisenatide and placebo), randomization strata of screening HbA1c (<8.0, ☐8.0%), randomization strata of metformin use at screening (Yes, No), country as fixed effects and baseline body weight as a covariate.
The analysis included measurements obtained before the introduction of rescue medication and up to 3 days after the last dose of the double-blind investigational product injection on or before Visit 12 (Week 24), or Day 169 if Visit 12 (Week 24) is not available. Patients with both baseline and Week 24 (LOCF) measurements are included.

TABLE 18

Number (%) of patients with >=5% weight loss from baseline to Week 24 - mITT population

| Weight loss | Placebo (N = 165) | Lixisenatide (N = 326) |
|---|---|---|
| Number | 161 | 311 |
| ≥5% | 5 (3.1%) | 41 (13.2%) |
| <5%[a] | 156 (96.9%) | 270 (86.8%) |

[a]Patients with less than 5% weight loss are included in this category, including patients who gained weight.
The analysis included measurements obtained before the introduction of rescue medication and up to 3 days after the last dose of the double-blind investigational product injection on or before Visit 12 (Week 24), or Day 169 if Visit 12 (Week 24) is not available. Patients with both baseline and Week 24 (LOCF) measurements are included.

TABLE 19

Number (%) of patients requiring rescue therapy during the 24-week treatment period - mITT population

| Requiring rescue therapy | Placebo (N = 165) | Lixisenatide (N = 326) |
|---|---|---|
| Number | 165 | 326 |
| Yes | 12 (7.3%) | 18 (5.5%) |
| No | 153 (92.7%) | 308 (94.5%) |
| p-value vs. placebo[a] | — | 0.4433 |

[a]Cochran-Mantel-Haenszel (CMH) method stratified by randomization strata of screening HbA1c (<8.0 or ≥8.0%) and metformin use at screening (Yes, No).

TABLE 20

Mean change in basal insulin dose (U) from baseline to Week 24 - mITT population

| Daily basal insulin dose (U) | Placebo (N = 165) | Lixisenatide (N = 326) |
|---|---|---|
| Baseline | | |
| Number | 165 | 325 |
| Mean (SD) | 57.65 (34.73) | 53.62 (33.97) |
| Median | 45.00 | 42.00 |
| Min:Max | 30.0:200.0 | 20.0:400.0 |
| Week 24 (LOCF) | | |
| Number | 165 | 325 |
| Mean (SD) | 56.99 (34.98) | 50.47 (28.09) |
| Median | 45.00 | 40.00 |
| Min:Max | 0.0:200.0 | 0.0:200.0 |
| Change from baseline to Week 24 (LOCF) | | |
| Number | 165 | 325 |
| Mean (SD) | −0.66 (10.24) | −3.15 (19.62) |
| Median | 0.00 | 0.00 |
| Min:Max | −72.0:35.0 | −300.0:33.0 |
| LS Mean (SE)[a] | −1.93 (1.589) | −5.62 (1.317) |
| LS Mean difference (SE) vs. placebo[a] | — | −3.69 (1.464) |
| 95% CI | — | (−6.568 to −0.815) |
| p-value | — | 0.0120 |

LOCF = Last observation carried forward.
[a]Analysis of covariance (ANCOVA) model with treatment groups (lixisenatide and placebo), randomization strata of screening HbA1c (<8.0, ≥8.0%), randomization strata of metformin use at screening (Yes, No), country as fixed effects and baseline basal insulin dose as a covariate.
The analysis included measurements obtained before the introduction of rescue medication and up to the date of the last dose of the double-blind investigational product injection on or before Visit 12 (Week 24), or Day 169 if Visit 12 (Week 24) is not available. Patients with both baseline and Week 24 (LOCF) measurements are included.

TABLE 21

Mean change in glucose excursion (mmol/L) from baseline to Week 24 - mITT population

| Glucose excursion(mmol/L) | Placebo (N = 165) | Lixisenatide (N = 326) |
|---|---|---|
| Baseline | | |
| Number | 123 | 233 |
| Mean (SD) | 7.21 (3.44) | 7.69 (3.47) |
| Median | 7.20 | 7.70 |
| Min:Max | −4.7:15.0 | −1.3:15.9 |
| Week 24 (LOCF) | | |
| Number | 123 | 233 |
| Mean (SD) | 6.97 (3.56) | 3.35 (3.90) |
| Median | 6.70 | 3.10 |
| Min:Max | −0.2:20.2 | −6.3:13.9 |
| Change from baseline to Week 24 (LOCF) | | |
| Number | 123 | 233 |
| Mean (SD) | −0.25 (3.66) | −4.34 (4.39) |
| Median | −0.40 | −4.10 |
| Min:Max | −11.6:11.1 | −17.1:8.0 |
| LS Mean (SE)[a] | −0.34 (0.469) | −4.14 (0.408) |
| LS Mean difference (SE) vs. placebo[a] | — | −3.80 (0.392) |
| 95% CI | — | (−4.572 to −3.031) |
| p-value | — | <.0001 |

LOCF = Last observation carried forward.
[a]Analysis of covariance (ANCOVA) model with treatment groups (lixisenatide and placebo), randomization strata of screening HbA1c (<8.0, ☐8.0%), randomization strata of metformin use at screening (Yes, No), country as fixed effects and baseline glucose excursion value as a covariate.
Glucose excursion = 2-hour postprandial plasma glucose - plasma glucose 30 minutes prior to the meal test before study drug administration.
The analysis included measurements obtained before the introduction of rescue medication and up to the date of the last dose of the double-blind investigational product injection on or before Visit 12 (Week 24), or Day 169 if Visit 12 (Week 24) is not available. Patients with both baseline and Week 24 (LOCF) measurements are included.

Safety

An overview of the adverse events observed during the on-treatment period for the whole study is provided in Table 22. The proportions of the patients with treatment emergent adverse events (TEAEs) were generally comparable between the two treatment groups (87.5% for lixisenatide versus 85.6% for placebo). Four patients (2 in lixisenatide group and 2 in placebo) had TEAEs leading to death. The percentage of patients who experienced serious TEAEs was higher in the lixisenatide group (14.0%) than in the placebo group (10.2%). The percentage of patients with TEAEs leading to treatment discontinuation was 10.7% in the lixisenatide group compared with 7.2% in the placebo group. Tables 23, 24, and 25 summarize TEAEs leading to death, serious TEAEs, and TEAEs leading to treatment discontinuation by primary SOC, HLGT, HLT and PT, respectively. The most common TEAE leading to treatment discontinuation was nausea in the lixisenatide group (11 patients [3.4%]), while no patient in the placebo group discontinued the treatment due to nausea.

Table 35 in the appendix presents the incidences of TEAEs occurring in at least 1% of patients in any treatment group during the on-treatment period for the whole study. Hypoglycaemia was the most frequently reported TEAE for both the lixisenatide (138 [42.1%]) and placebo groups (68 [40.7%]). Aside from hypoglycemia, the most common TEAE in the lixisenatide group was nausea (96 patients [29.3%] for lixisenatide versus 16 patients [9.6%] for placebo) followed by headache (41 patients [12.5%] for lixisenatide versus 17 [10.2%] for placebo) and diarrhoea (37 patients [11.3%] for lixisenatide versus 10 [6.0%] for placebo).

TABLE 22

Overview of adverse event profile: treatment emergent adverse events during the on-treatment period for the whole study - Safety population

| | Placebo (N = 167) | Lixisenatide (N = 328) |
|---|---|---|
| Patients with any TEAE | 143 (85.6%) | 287 (87.5%) |
| Patients with any serious TEAE | 17 (10.2%) | 46 (14.0%) |
| Patients with any TEAE leading to death | 2 (1.2%) | 2 (0.6%) |
| Patients with any TEAE leading to permanent treatment discontinuation | 12 (7.2%) | 35 (10.7%) |

TEAE: Treatment emergent adverse event.
On-treatment period for the whole study = the time from the first dose of double-blind study medication up to 3 days after the last dose administration.
n (%) = number and percentage of patients with at least one adverse event.

TABLE 23

Number (%) of patients experiencing TEAE(s) leading to death during the overall treatment period by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| Any class | 2 (1.2%) | 2 (0.6%) |
| NEOPLASMS BENIGN, MALIGNANT AND UNSPECIFIED (INCL CYSTS AND POLYPS) | 1 (0.6%) | 0 |
| HLGT: Nervous system neoplasms malignant and unspecified NEC | 1 (0.6%) | 0 |
| HLT: Nervous system neoplasms unspecified malignancy NEC | 1 (0.6%) | 0 |
| Glioma | 1 (0.6%) | 0 |
| CARDIAC DISORDERS | 0 | 1 (0.3%) |
| HLGT: Coronary artery disorders | 0 | 1 (0.3%) |
| HLT: Ischaemic coronary artery disorders | 0 | 1 (0.3%) |
| Myocardial infarction | 0 | 1 (0.3%) |
| RESPIRATORY, THORACIC AND MEDIASTINAL DISORDERS | 1 (0.6%) | 0 |
| HLGT: Respiratory disorders NEC | 1 (0.6%) | 0 |
| HLT: Respiratory failures (excl neonatal) | 1 (0.6%) | 0 |
| Respiratory failure | 1 (0.6%) | 0 |
| GENERAL DISORDERS AND ADMINISTRATION SITE CONDITIONS | 0 | 1 (0.3%) |
| HLGT: Fatal outcomes | 0 | 1 (0.3%) |
| HLT: Death and sudden death | 0 | 1 (0.3%) |
| Sudden cardiac death | 0 | 1 (0.3%) |

TEAE: Treatment emergent adverse event,
SOC: System Organ Class,
HLGT: High Level Group Term,
HLT: High Level Term,
PT: Preferred Term.
On-treatment period for the whole study = the time from the first dose of double-blind study medication up to 3 days after the last dose administration.
MedDRA version: 13.1.
n (%) = number and percentage of patients with at least one TEAE leading to death.
Note:
Table sorted by SOC internationally agreed order and HLGT, HLT, PT alphabetic order.

TABLE 24

Number (%) of patients experiencing serious TEAE(s) during the overall treatment period presented by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| Any class | 17 (10.2%) | 46 (14.0%) |
| INFECTIONS AND INFESTATIONS | 2 (1.2%) | 11 (3.4%) |
| HLGT: Bacterial infectious disorders | 1 (0.6%) | 1 (0.3%) |
| HLT: Bacterial infections NEC | 1 (0.6%) | 1 (0.3%) |
| Cellulitis | 0 | 1 (0.3%) |
| Incision site cellulitis | 1 (0.6%) | 0 |
| HLGT: Infections - pathogen unspecified | 2 (1.2%) | 8 (2.4%) |
| HLT: Infections NEC | 0 | 1 (0.3%) |
| Localised infection | 0 | 1 (0.3%) |
| HLT: Lower respiratory tract and lung infections | 2 (1.2%) | 3 (0.9%) |
| Bronchitis | 1 (0.6%) | 0 |
| Pneumonia | 2 (1.2%) | 3 (0.9%) |
| HLT: Sepsis, bacteraemia, viraemia and fungaemia NEC | 1 (0.6%) | 0 |
| Septic shock | 1 (0.6%) | 0 |
| HLT: Upper respiratory tract infections | 0 | 1 (0.3%) |
| Pharyngeal abscess | 0 | 1 (0.3%) |
| HLT: Urinary tract infections | 0 | 3 (0.9%) |
| Pyelonephritis | 0 | 1 (0.3%) |
| Urinary tract infection | 0 | 2 (0.6%) |
| HLGT: Viral infectious disorders | 0 | 3 (0.9%) |
| HLT: Coxsackie viral infections | 0 | 1 (0.3%) |
| Coxsackie viral infection | 0 | 1 (0.3%) |
| HLT: Papilloma viral infections | 0 | 1 (0.3%) |
| Anogenital warts | 0 | 1 (0.3%) |
| HLT: Viral infections NEC | 0 | 1 (0.3%) |
| Pneumonia viral | 0 | 1 (0.3%) |
| NEOPLASMS BENIGN, MALIGNANT AND UNSPECIFIED (INCL CYSTS AND POLYPS) | 3 (1.8%) | 6 (1.8%) |
| HLGT: Breast neoplasms malignant and unspecified (incl nipple) | 0 | 1 (0.3%) |
| HLT: Breast and nipple neoplasms malignant | 0 | 1 (0.3%) |
| Breast cancer | 0 | 1 (0.3%) |
| HLGT: Gastrointestinal neoplasms malignant and unspecified | 0 | 1 (0.3%) |
| HLT: Pancreatic neoplasms malignant (excl islet cell and carcinoid) | 0 | 1 (0.3%) |
| Pancreatic carcinoma | 0 | 1 (0.3%) |
| HLGT: Nervous system neoplasms malignant and unspecified NEC | 1 (0.6%) | 0 |
| HLT: Nervous system neoplasms unspecified malignancy NEC | 1 (0.6%) | 0 |
| Glioma | 1 (0.6%) | 0 |
| HLGT: Renal and urinary tract neoplasms malignant and unspecified | 1 (0.6%) | 0 |
| HLT: Renal neoplasms malignant | 1 (0.6%) | 0 |
| Renal cell carcinoma | 1 (0.6%) | 0 |
| HLGT: Reproductive neoplasms female malignant and unspecified | 0 | 1 (0.3%) |
| HLT: Cervix neoplasms malignant | 0 | 1 (0.3%) |
| Cervix carcinoma | 0 | 1 (0.3%) |
| HLGT: Reproductive neoplasms male malignant and unspecified | 1 (0.6%) | 0 |
| HLT: Prostatic neoplasms malignant | 1 (0.6%) | 0 |
| Prostate cancer | 1 (0.6%) | 0 |
| HLGT: Respiratory and mediastinal neoplasms malignant and unspecified | 0 | 3 (0.9%) |
| HLT: Respiratory tract and pleural neoplasms malignant cell type unspecified NEC | 0 | 2 (0.6%) |
| Lung cancer metastatic | 0 | 1 (0.3%) |
| Lung neoplasm malignant | 0 | 1 (0.3%) |
| HLT: Respiratory tract small cell carcinomas | 0 | 1 (0.3%) |
| Small cell lung cancer stage unspecified | 0 | 1 (0.3%) |
| BLOOD AND LYMPHATIC SYSTEM DISORDERS | 1 (0.6%) | 0 |
| HLGT: Platelet disorders | 1 (0.6%) | 0 |
| HLT: Thrombocytopenias | 1 (0.6%) | 0 |
| Thrombocytopenia | 1 (0.6%) | 0 |
| ENDOCRINE DISORDERS | 0 | 1 (0.3%) |
| HLGT: Thyroid gland disorders | 0 | 1 (0.3%) |
| HLT: Thyroid disorders NEC | 0 | 1 (0.3%) |
| Goitre | 0 | 1 (0.3%) |
| METABOLISM AND NUTRITION DISORDERS | 1 (0.6%) | 2 (0.6%) |
| HLGT: Glucose metabolism disorders (incl diabetes mellitus) | 1 (0.6%) | 2 (0.6%) |
| HLT: Hypoglycaemic conditions NEC | 1 (0.6%) | 2 (0.6%) |
| Hypoglycaemia | 1 (0.6%) | 1 (0.3%) |
| Hypoglycaemic unconsciousness | 0 | 1 (0.3%) |
| NERVOUS SYSTEM DISORDERS | 1 (0.6%) | 3 (0.9%) |
| HLGT: Central nervous system vascular disorders | 0 | 2 (0.6%) |
| HLT: Central nervous system vascular disorders NEC | 0 | 1 (0.3%) |
| Carotid artery stenosis | 0 | 1 (0.3%) |
| HLT: Transient cerebrovascular events | 0 | 1 (0.3%) |
| Transient ischaemic attack | 0 | 1 (0.3%) |
| HLGT: Headaches | 0 | 1 (0.3%) |

TABLE 24-continued

Number (%) of patients experiencing serious TEAE(s) during the overall treatment period presented by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| HLT: Migraine headaches | 0 | 1 (0.3%) |
| Migraine | 0 | 1 (0.3%) |
| HLGT: Neurological disorders NEC | 1 (0.6%) | 2 (0.6%) |
| HLT: Disturbances in consciousness NEC | 0 | 1 (0.3%) |
| Somnolence | 0 | 1 (0.3%) |
| HLT: Neurological signs and symptoms NEC | 0 | 1 (0.3%) |
| Presyncope | 0 | 1 (0.3%) |
| HLT: Sensory abnormalities NEC | 1 (0.6%) | 0 |
| Intercostal neuralgia | 1 (0.6%) | 0 |
| EYE DISORDERS | 0 | 4 (1.2%) |
| HLGT: Anterior eye structural change, deposit and degeneration | 0 | 2 (0.6%) |
| HLT: Cataract conditions | 0 | 1 (0.3%) |
| Cataract | 0 | 1 (0.3%) |
| HLT: Lens structural change, deposit and degeneration (excl cataracts) | 0 | 1 (0.3%) |
| Lens dislocation | 0 | 1 (0.3%) |
| HLGT: Retina, choroid and vitreous haemorrhages and vascular disorders | 0 | 2 (0.6%) |
| HLT: Retinal bleeding and vascular disorders (excl retinopathy) | 0 | 1 (0.3%) |
| Retinal haemorrhage | 0 | 1 (0.3%) |
| HLT: Retinopathies NEC | 0 | 1 (0.3%) |
| Retinopathy haemorrhagic | 0 | 1 (0.3%) |
| CARDIAC DISORDERS | 9 (5.4%) | 5 (1.5%) |
| HLGT: Cardiac arrhythmias | 1 (0.6%) | 1 (0.3%) |
| HLT: Supraventricular arrhythmias | 1 (0.6%) | 1 (0.3%) |
| Atrial fibrillation | 1 (0.6%) | 0 |
| Atrial flutter | 0 | 1 (0.3%) |
| HLGT: Coronary artery disorders | 8 (4.8%) | 4 (1.2%) |
| HLT: Coronary artery disorders NEC | 4 (2.4%) | 2 (0.6%) |
| Coronary artery disease | 4 (2.4%) | 2 (0.6%) |
| HLT: Ischaemic coronary artery disorders | 6 (3.6%) | 2 (0.6%) |
| Acute myocardial infarction | 2 (1.2%) | 1 (0.3%) |
| Angina pectoris | 2 (1.2%) | 0 |
| Myocardial infarction | 1 (0.6%) | 1 (0.3%) |
| Myocardial ischaemia | 1 (0.6%) | 0 |
| HLGT: Myocardial disorders | 1 (0.6%) | 1 (0.3%) |
| HLT: Cardiomyopathies | 1 (0.6%) | 0 |
| Ischaemic cardiomyopathy | 1 (0.6%) | 0 |
| HLT: Myocardial disorders NEC | 0 | 1 (0.3%) |
| Left ventricular dysfunction | 0 | 1 (0.3%) |
| HLGT: Pericardial disorders | 1 (0.6%) | 0 |
| HLT: Pericardial disorders NEC | 1 (0.6%) | 0 |
| Pericardial effusion | 1 (0.6%) | 0 |
| VASCULAR DISORDERS | 0 | 2 (0.6%) |
| HLGT: Arteriosclerosis, stenosis, vascular insufficiency and necrosis | 0 | 1 (0.3%) |
| HLT: Aortic necrosis and vascular insufficiency | 0 | 1 (0.3%) |
| Leriche syndrome | 0 | 1 (0.3%) |
| HLGT: Embolism and thrombosis | 0 | 1 (0.3%) |
| HLT: Peripheral embolism and thrombosis | 0 | 1 (0.3%) |
| Deep vein thrombosis | 0 | 1 (0.3%) |
| RESPIRATORY, THORACIC AND MEDIASTINAL DISORDERS | 2 (1.2%) | 0 |
| HLGT: Pulmonary vascular disorders | 1 (0.6%) | 0 |
| HLT: Pulmonary thrombotic and embolic conditions | 1 (0.6%) | 0 |
| Pulmonary embolism | 1 (0.6%) | 0 |
| HLGT: Respiratory disorders NEC | 1 (0.6%) | 0 |
| HLT: Respiratory failures (excl neonatal) | 1 (0.6%) | 0 |
| Respiratory failure | 1 (0.6%) | 0 |
| GASTROINTESTINAL DISORDERS | 0 | 3 (0.9%) |
| HLGT: Exocrine pancreas conditions | 0 | 1 (0.3%) |
| HLT: Acute and chronic pancreatitis | 0 | 1 (0.3%) |
| Pancreatitis | 0 | 1 (0.3%) |
| HLGT: Gastrointestinal haemorrhages NEC | 0 | 1 (0.3%) |
| HLT: Non-site specific gastrointestinal haemorrhages | 0 | 1 (0.3%) |
| Upper gastrointestinal haemorrhage | 0 | 1 (0.3%) |
| HLGT: Gastrointestinal ulceration and perforation | 0 | 1 (0.3%) |
| HLT: Gastric ulcers and perforation | 0 | 1 (0.3%) |
| Gastric ulcer | 0 | 1 (0.3%) |
| SKIN AND SUBCUTANEOUS TISSUE DISORDERS | 2 (1.2%) | 1 (0.3%) |
| HLGT: Epidermal and dermal conditions | 1 (0.6%) | 0 |
| HLT: Dermatitis ascribed to specific agent | 1 (0.6%) | 0 |
| Toxic skin eruption | 1 (0.6%) | 0 |
| HLGT: Skin and subcutaneous tissue disorders NEC | 1 (0.6%) | 1 (0.3%) |
| HLT: Skin and subcutaneous tissue ulcerations | 1 (0.6%) | 1 (0.3%) |
| Neuropathic ulcer | 1 (0.6%) | 0 |
| Skin ulcer | 0 | 1 (0.3%) |
| MUSCULOSKELETAL AND CONNECTIVE TISSUE DISORDERS | 0 | 2 (0.6%) |
| HLGT: Joint disorders | 0 | 1 (0.3%) |
| HLT: Osteoarthropathies | 0 | 1 (0.3%) |
| Osteoarthritis | 0 | 1 (0.3%) |
| HLGT: Musculoskeletal and connective tissue disorders NEC | 0 | 1 (0.3%) |
| HLT: Musculoskeletal and connective tissue pain and discomfort | 0 | 1 (0.3%) |
| Musculoskeletal chest pain | 0 | 1 (0.3%) |
| RENAL AND URINARY DISORDERS | 2 (1.2%) | 2 (0.6%) |
| HLGT: Bladder and bladder neck disorders (excl calculi) | 0 | 1 (0.3%) |
| HLT: Bladder neoplasms | 0 | 1 (0.3%) |
| Urinary bladder polyp | 0 | 1 (0.3%) |
| HLGT: Nephropathies | 1 (0.6%) | 0 |
| HLT: Nephropathies and tubular disorders NEC | 1 (0.6%) | 0 |
| Diabetic nephropathy | 1 (0.6%) | 0 |
| HLGT: Renal disorders (excl nephropathies) | 1 (0.6%) | 0 |
| HLT: Renal failure and impairment | 1 (0.6%) | 0 |
| Renal failure | 1 (0.6%) | 0 |
| HLGT: Urethral disorders (excl calculi) | 0 | 1 (0.3%) |
| HLT: Structural and obstructive urethral disorders (excl congenital) | 0 | 1 (0.3%) |
| Urethral stenosis | 0 | 1 (0.3%) |
| REPRODUCTIVE SYSTEM AND BREAST DISORDERS | 0 | 1 (0.3%) |
| HLGT: Prostatic disorders (excl infections and inflammations) | 0 | 1 (0.3%) |
| HLT: Prostatic neoplasms and hypertrophy | 0 | 1 (0.3%) |
| Benign prostatic hyperplasia | 0 | 1 (0.3%) |
| GENERAL DISORDERS AND ADMINISTRATION SITE CONDITIONS | 1 (0.6%) | 5 (1.5%) |
| HLGT: Fatal outcomes | 0 | 1 (0.3%) |
| HLT: Death and sudden death | 0 | 1 (0.3%) |
| Sudden cardiac death | 0 | 1 (0.3%) |
| HLGT: General system disorders NEC | 1 (0.6%) | 4 (1.2%) |
| HLT: Pain and discomfort NEC | 1 (0.6%) | 4 (1.2%) |
| Non-cardiac chest pain | 1 (0.6%) | 4 (1.2%) |
| INJURY, POISONING AND PROCEDURAL COMPLICATIONS | 1 (0.6%) | 2 (0.6%) |
| HLGT: Bone and joint injuries | 1 (0.6%) | 1 (0.3%) |
| HLT: Spinal fractures and dislocations | 0 | 1 (0.3%) |
| Spinal compression fracture | 0 | 1 (0.3%) |
| HLT: Thoracic cage fractures and dislocations | 0 | 1 (0.3%) |
| Rib fracture | 0 | 1 (0.3%) |
| HLT: Upper limb fractures and dislocations | 1 (0.6%) | 0 |
| Wrist fracture | 1 (0.6%) | 0 |
| HLGT: Procedural related injuries and complications NEC | 0 | 1 (0.3%) |

TABLE 24-continued

Number (%) of patients experiencing serious TEAE(s) during the overall treatment period presented by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| HLT: Non-site specific procedural complications | 0 | 1 (0.3%) |
| Procedural pain | 0 | 1 (0.3%) |
| SURGICAL AND MEDICAL PROCEDURES | 5 (3.0%) | 1 (0.3%) |
| HLGT: Vascular therapeutic procedures | 5 (3.0%) | 1 (0.3%) |
| HLT: Arterial therapeutic procedures (excl aortic) | 5 (3.0%) | 1 (0.3%) |
| Coronary angioplasty | 2 (1.2%) | 0 |
| Coronary arterial stent insertion | 1 (0.6%) | 0 |
| Coronary artery bypass | 2 (1.2%) | 1 (0.3%) |
| Coronary revascularisation | 1 (0.6%) | 0 |
| SOCIAL CIRCUMSTANCES | 1 (0.6%) | 0 |
| HLGT: Legal issues | 1 (0.6%) | 0 |
| HLT: Crime victims | 1 (0.6%) | 0 |
| Victim of crime | 1 (0.6%) | 0 |

TEAE: Treatment emergent adverse event,
SOC: System Organ Class,
HLGT: High Level Group Term,
HLT: High Level Term,
PT: Preferred Term.
On-treatment period for the whole study = the time from the first dose of double-blind study medication up to 3 days after the last dose administration.
MedDRA version: 13.1.
n (%) = number and percentage of patients with at least one serious TEAE.
Note:
Table sorted by SOC internationally agreed order and HLGT, HLT, PT alphabetic order.

TABLE 25

Number (%) of patients experiencing TEAE(s) leading to permanent treatment discontinuation during the overall treatment period by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| Any class | 12 (7.2%) | 35 (10.7%) |
| INFECTIONS AND INFESTATIONS | 1 (0.6%) | 1 (0.3%) |
| HLGT: Infections - pathogen unspecified | 1 (0.6%) | 1 (0.3%) |
| HLT: Abdominal and gastrointestinal infections | 0 | 1 (0.3%) |
| Gastroenteritis | 0 | 1 (0.3%) |
| HLT: Lower respiratory tract and lung infections | 1 (0.6%) | 0 |
| Pneumonia | 1 (0.6%) | 0 |
| HLT: Sepsis, bacteraemia, viraemia and fungaemia NEC | 1 (0.6%) | 0 |
| Septic shock | 1 (0.6%) | 0 |
| NEOPLASMS BENIGN, MALIGNANT AND UNSPECIFIED (INCL CYSTS AND POLYPS) | 1 (0.6%) | 3 (0.9%) |
| HLGT: Breast neoplasms malignant and unspecified (incl nipple) | 0 | 1 (0.3%) |
| HLT: Breast and nipple neoplasms malignant | 0 | 1 (0.3%) |
| Breast cancer | 0 | 1 (0.3%) |
| HLGT: Gastrointestinal neoplasms malignant and unspecified | 0 | 1 (0.3%) |
| HLT: Pancreatic neoplasms malignant (excl islet cell and carcinoid) | 0 | 1 (0.3%) |
| Pancreatic carcinoma | 0 | 1 (0.3%) |
| HLGT: Nervous system neoplasms malignant and unspecified NEC | 1 (0.6%) | 0 |
| HLT: Nervous system neoplasms unspecified malignancy NEC | 1 (0.6%) | 0 |
| Glioma | 1 (0.6%) | 0 |
| HLGT: Respiratory and mediastinal neoplasms malignant and unspecified | 0 | 1 (0.3%) |
| HLT: Respiratory tract small cell carcinomas | 0 | 1 (0.3%) |
| Small cell lung cancer stage unspecified | 0 | 1 (0.3%) |
| BLOOD AND LYMPHATIC SYSTEM DISORDERS | 1 (0.6%) | 0 |
| HLGT: Platelet disorders | 1 (0.6%) | 0 |
| HLT: Thrombocytopenias | 1 (0.6%) | 0 |
| Thrombocytopenia | 1 (0.6%) | 0 |
| IMMUNE SYSTEM DISORDERS | 0 | 2 (0.6%) |
| HLGT: Allergic conditions | 0 | 2 (0.6%) |
| HLT: Allergic conditions NEC | 0 | 2 (0.6%) |
| Hypersensitivity | 0 | 2 (0.6%) |
| METABOLISM AND NUTRITION DISORDERS | 0 | 3 (0.9%) |
| HLGT: Appetite and general nutritional disorders | 0 | 1 (0.3%) |
| HLT: Appetite disorders | 0 | 1 (0.3%) |
| Decreased appetite | 0 | 1 (0.3%) |
| HLGT: Glucose metabolism disorders (incl diabetes mellitus) | 0 | 2 (0.6%) |
| HLT: Hypoglycaemic conditions NEC | 0 | 2 (0.6%) |
| Hypoglycaemia | 0 | 1 (0.3%) |
| Hypoglycaemic unconsciousness | 0 | 1 (0.3%) |
| NERVOUS SYSTEM DISORDERS | 0 | 3 (0.9%) |
| HLGT: Central nervous system vascular disorders | 0 | 1 (0.3%) |
| HLT: Central nervous system vascular disorders NEC | 0 | 1 (0.3%) |

TABLE 25-continued

Number (%) of patients experiencing TEAE(s) leading to permanent treatment discontinuation during the overall treatment period by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| Carotid arteriosclerosis | 0 | 1 (0.3%) |
| HLGT: Headaches | 0 | 1 (0.3%) |
| HLT: Headaches NEC | 0 | 1 (0.3%) |
| Headache | 0 | 1 (0.3%) |
| HLGT: Neurological disorders NEC | 0 | 1 (0.3%) |
| HLT: Neurological signs and symptoms NEC | 0 | 1 (0.3%) |
| Dizziness | 0 | 1 (0.3%) |
| EYE DISORDERS | 0 | 1 (0.3%) |
| HLGT: Retina, choroid and vitreous haemorrhages and vascular disorders | 0 | 1 (0.3%) |
| HLT: Retinopathies NEC | 0 | 1 (0.3%) |
| Retinopathy haemorrhagic | 0 | 1 (0.3%) |
| EAR AND LABYRINTH DISORDERS | 0 | 1 (0.3%) |
| HLGT: Inner ear and VIIIth cranial nerve disorders | 0 | 1 (0.3%) |
| HLT: Inner ear signs and symptoms | 0 | 1 (0.3%) |
| Tinnitus | 0 | 1 (0.3%) |
| Vertigo | 0 | 1 (0.3%) |
| CARDIAC DISORDERS | 4 (2.4%) | 2 (0.6%) |
| HLGT: Cardiac arrhythmias | 1 (0.6%) | 0 |
| HLT: Supraventricular arrhythmias | 1 (0.6%) | 0 |
| Atrial fibrillation | 1 (0.6%) | 0 |
| HLGT: Coronary artery disorders | 4 (2.4%) | 2 (0.6%) |
| HLT: Coronary artery disorders NEC | 2 (1.2%) | 1 (0.3%) |
| Coronary artery disease | 2 (1.2%) | 1 (0.3%) |
| HLT: Ischaemic coronary artery disorders | 2 (1.2%) | 1 (0.3%) |
| Acute myocardial infarction | 2 (1.2%) | 0 |
| Myocardial infarction | 0 | 1 (0.3%) |
| HLGT: Myocardial disorders | 0 | 1 (0.3%) |
| HLT: Myocardial disorders NEC | 0 | 1 (0.3%) |
| Left ventricular dysfunction | 0 | 1 (0.3%) |
| VASCULAR DISORDERS | 0 | 1 (0.3%) |
| HLGT: Arteriosclerosis, stenosis, vascular insufficiency and necrosis | 0 | 1 (0.3%) |
| HLT: Aortic necrosis and vascular insufficiency | 0 | 1 (0.3%) |
| Leriche syndrome | 0 | 1 (0.3%) |
| RESPIRATORY, THORACIC AND MEDIASTINAL DISORDERS | 1 (0.6%) | 0 |
| HLGT: Respiratory disorders NEC | 1 (0.6%) | 0 |
| HLT: Respiratory failures (excl neonatal) | 1 (0.6%) | 0 |
| Respiratory failure | 1 (0.6%) | 0 |
| GASTROINTESTINAL DISORDERS | 2 (1.2%) | 17 (5.2%) |
| HLGT: Exocrine pancreas conditions | 0 | 1 (0.3%) |
| HLT: Acute and chronic pancreatitis | 0 | 1 (0.3%) |
| Pancreatitis | 0 | 1 (0.3%) |
| HLGT: Gastrointestinal haemorrhages NEC | 0 | 1 (0.3%) |
| HLT: Non-site specific gastrointestinal haemorrhages | 0 | 1 (0.3%) |
| Upper gastrointestinal haemorrhage | 0 | 1 (0.3%) |
| HLGT: Gastrointestinal motility and defaecation conditions | 0 | 4 (1.2%) |
| HLT: Diarrhoea (excl infective) | 0 | 3 (0.9%) |
| Diarrhoea | 0 | 3 (0.9%) |
| HLT: Gastrointestinal atonic and hypomotility disorders NEC | 0 | 1 (0.3%) |
| Gastrooesophageal reflux disease | 0 | 1 (0.3%) |
| HLGT: Gastrointestinal signs and symptoms | 1 (0.6%) | 13 (4.0%) |
| HLT: Dyspeptic signs and symptoms | 0 | 2 (0.6%) |
| Dyspepsia | 0 | 2 (0.6%) |
| HLT: Flatulence, bloating and distension | 0 | 1 (0.3%) |
| Abdominal distension | 0 | 1 (0.3%) |
| HLT: Gastrointestinal and abdominal pains (excl oral and throat) | 0 | 1 (0.3%) |
| Abdominal pain | 0 | 1 (0.3%) |
| HLT: Gastrointestinal signs and symptoms NEC | 1 (0.6%) | 0 |
| Faecal incontinence | 1 (0.6%) | 0 |
| HLT: Nausea and vomiting symptoms | 0 | 11 (3.4%) |
| Nausea | 0 | 11 (3.4%) |
| Vomiting | 0 | 2 (0.6%) |
| HLGT: Tongue conditions | 1 (0.6%) | 0 |
| HLT: Tongue signs and symptoms | 1 (0.6%) | 0 |
| Tongue oedema | 1 (0.6%) | 0 |
| SKIN AND SUBCUTANEOUS TISSUE DISORDERS | 0 | 2 (0.6%) |
| HLGT: Epidermal and dermal conditions | 0 | 1 (0.3%) |
| HLT: Erythemas | 0 | 1 (0.3%) |
| Rash erythematous | 0 | 1 (0.3%) |
| HLGT: Skin appendage conditions | 0 | 1 (0.3%) |
| HLT: Apocrine and eccrine gland disorders | 0 | 1 (0.3%) |
| Hyperhidrosis | 0 | 1 (0.3%) |
| MUSCULOSKELETAL AND CONNECTIVE TISSUE DISORDERS | 1 (0.6%) | 0 |

TABLE 25-continued

Number (%) of patients experiencing TEAE(s) leading to permanent treatment discontinuation during the overall treatment period by primary SOC, HLGT, HLT, and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| HLGT: Musculoskeletal and connective tissue deformities (incl intervertebral disc disorders) | 1 (0.6%) | 0 |
|     HLT: Spine and neck deformities | 1 (0.6%) | 0 |
|         Spondylolisthesis | 1 (0.6%) | 0 |
| RENAL AND URINARY DISORDERS | 2 (1.2%) | 2 (0.6%) |
|   HLGT: Nephropathies | 1 (0.6%) | 1 (0.3%) |
|     HLT: Nephropathies and tubular disorders NEC | 1 (0.6%) | 1 (0.3%) |
|         Diabetic nephropathy | 1 (0.6%) | 1 (0.3%) |
|   HLGT: Renal disorders (excl nephropathies) | 1 (0.6%) | 1 (0.3%) |
|     HLT: Renal failure and impairment | 1 (0.6%) | 1 (0.3%) |
|         Renal failure | 1 (0.6%) | 0 |
|         Renal failure acute | 0 | 1 (0.3%) |
| PREGNANCY, PUERPERIUM AND PERINATAL CONDITIONS | 1 (0.6%) | 0 |
|   HLGT: Pregnancy, labour, delivery and postpartum conditions | 1 (0.6%) | 0 |
|     HLT: Normal pregnancy, labour and delivery | 1 (0.6%) | 0 |
|         Pregnancy | 1 (0.6%) | 0 |
| GENERAL DISORDERS AND ADMINISTRATION SITE CONDITIONS | 0 | 3 (0.9%) |
|   HLGT: Fatal outcomes | 0 | 1 (0.3%) |
|     HLT: Death and sudden death | 0 | 1 (0.3%) |
|         Sudden cardiac death | 0 | 1 (0.3%) |
|   HLGT: General system disorders NEC | 0 | 2 (0.6%) |
|     HLT: Asthenic conditions | 0 | 2 (0.6%) |
|         Asthenia | 0 | 2 (0.6%) |
| INVESTIGATIONS | 2 (1.2%) | 1 (0.3%) |
|   HLGT: Endocrine investigations (incl sex hormones) | 1 (0.6%) | 1 (0.3%) |
|     HLT: Gastrointestinal, pancreatic and APUD hormone analyses | 1 (0.6%) | 1 (0.3%) |
|         Blood calcitonin increased | 1 (0.6%) | 1 (0.3%) |
|   HLGT: Hepatobiliary investigations | 1 (0.6%) | 0 |
|     HLT: Liver function analyses | 1 (0.6%) | 0 |
|         Liver function test abnormal | 1 (0.6%) | 0 |

TEAE: Treatment emergent adverse event, SOC: System Organ Class, HLGT: High Level Group Term, HLT: High Level Term, PT: Preferred Term.
On-treatment period for the whole study = the time from the first dose of double-blind study medication up to 3 days after the last dose administration.
MedDRA version: 13.1.
n (%) = number and percentage of patients with at least one TEAE leading to permanent treatment discontinuation.
Note:
Table sorted by SOC internationally agreed order and HLGT, HLT, PT alphabetic order.

According to the protocol definition for symptomatic hypoglycemia, 138 (42.1%) lixisenatide-treated patients and 65 (38.9%) placebo-treated patients reported at least one symptomatic hypoglycemic event during the on-treatment period for the whole study (Table 26). Of these patients having the symptomatic hypoglycemia events per protocol definition, 4 lixisenatide-treated patients had investigator reported AE terms other than hypoglycemia (hypoglycaemic unconsciousness, hypoglycemia unawareness, blood glucose decreased, and tremor), which are not displayed as the hypoglycemia PT in the TEAE summary table (Table 35). Conversely, 7 patients (4 for lixisenatide and 3 for placebo) who reported hypoglycemia TEAEs are excluded from the protocol defined symptomatic hypoglycemia events in Table 26 because of either not fulfilling the hypoglycemia per protocol definition (the event glucose values≥60 mg/dL) or missing relevant information for analysis (the complementary form was missing for one placebo-treated patient).

Seven (2.1%) lixisenatide-treated patients reported 8 severe symptomatic hypoglycemia events per protocol definition, whereas 1 (0.6%) placebo-treated patients reported 1 severe symptomatic hypoglycemia event during the same period (Table 27).

TABLE 26

Summary of symptomatic hypoglycemia during the on-treatment period for the whole study - Safety population

| Type | Placebo<br>(N = 167) | Lixisenatide<br>(N = 328) |
|---|---|---|
| Total patient years | 231.22 | 442.71 |
| Any symptomatic hypoglycemia | | |
| Number of patients with events, n (%) | 65 (38.9%) | 138 (42.1%) |
| Number of patients with events per 100 patient years[1] | 28.1 | 31.2 |
| Blood glucose <60 mg/dL | | |
| Number of patients with events, n (%) | 64 (38.3%) | 134 (40.9%) |
| Number of patients with events per 100 patient years[1] | 27.7 | 30.3 |
| No blood glucose reported | | |
| Number of patients with events, n (%) | 2 (1.2%) | 20 (6.1%) |
| Number of patients with events per 100 patient years[1] | 0.9 | 4.5 |

Symptomatic hypoglycemia = symptomatic hypoglycemia as defined per protocol.
On-treatment period for the whole study = the time from the first dose of double-blind study medication up to 3 days after the last dose administration.
[1]Calculated as (number of patients with events*100 divided by total exposure + 3 days in patient years).

TABLE 27

Summary of severe symptomatic hypoglycemia during the on-treatment period for the whole study - Safety population

| Type | Placebo (N = 167) | Lixisenatide (N = 328) |
|---|---|---|
| Total patient years | 231.22 | 442.71 |
| Any severe symptomatic hypoglycemia | | |
| Number of patients with events, n (%) | 1 (0.6%) | 7 (2.1%) |
| Number of patients with events per 100 patient years[1] | 0.4 | 1.6 |
| Blood glucose <36 mg/dL | | |
| Number of patients with events, n (%) | 1 (0.6%) | 5 (1.5%) |
| Number of patients with events per 100 patient years[1] | 0.4 | 1.1 |
| No blood glucose reported | | |
| Number of patients with events, n (%) | 0 | 2 (0.6%) |
| Number of patients with events per 100 patient years[1] | 0 | 0.5 |

Severe symptomatic hypoglycemia = severe symptomatic hypoglycemia as defined per protocol.
On-treatment period for the whole study = the time from the first dose of double-blind study medication up to 3 days after the last dose administration.
[1]Calculated as (number of patients with events*100 divided by total exposure + 3 days in patient years).

Eight patients (2.4%) from lixisenatide group and one patient (0.6%) from placebo group experienced injection site reaction AEs (Table 28). The injection site reaction AEs were identified by searching for the term "injection site" in either the investigator reported AE PTs or PTs from the ARAC diagnosis after the allergic reaction adjudication. None of the reactions were serious or severe in intensity, nor did these AEs lead to IP discontinuation.

TABLE 28

Number (%) of patients experiencing injection site reactions during the on-treatment period for the whole study- Safety population

| Event Source Preferred Term | Placebo (N = 167) | Lixisenatide (N = 328) |
|---|---|---|
| Any injection site reactions | 1 (0.6%) | 8 (2.4%) |
| Investigator reported PTs | 1 (0.6%) | 7 (2.1%) |
| Injection site haematoma | 1 (0.6%) | 0 |
| Injection site haemorrhage | 0 | 1 (0.3%) |
| Injection site induration | 0 | 1 (0.3%) |
| Injection site infection | 0 | 1 (0.3%) |
| Injection site nodule | 0 | 1 (0.3%) |
| Injection site pain | 0 | 2 (0.6%) |
| Injection site pruritus | 0 | 1 (0.3%) |
| PTs by ARAC diagnosis | 0 | 1 (0.3%) |
| Injection site reaction | 0 | 1 (0.3%) |

On-treatment period for the whole study = the time from the first dose of double-blind study medication up to 3 days after the last dose administration.
ARAC = Allergic Reaction Assessment Committee.

A total of 33 cases were reported for 28 patients as suspected allergic events by investigators and sent to ARAC for adjudication during the on-treatment period for the whole study. Of these, 11 events from 11 patients (8 [2.4%] lixisenatide-treated patients and 3 [1.8%] placebo-treated patients) were adjudicated as allergic reactions by the ARAC, but only 3 events from 3 patients (two anaphylactic reaction events from lixisenatide group and one angioedema event from placebo group) were adjudicated as possibly related to the IP (Table 29).

Patient 840635031 (lixisenatide): A 52-year-old female patient with a medical history of dyslipidemia, asthma, allergic rhinitis, allergies to drug, food, pollen and dust, as well as urticaria and angioedema in the past, reported a mild injection site reactions with each dose since 8 Jun. 2009 (21 days on the IP). The patient complained of local and generalized itching, and swelling at the injection site with erythema. She also presented with hoarseness, change in pitch of voice, wheezing and chest tightness. The vital signs during a reaction (17 Jun. 2009, 9:08) were: BP129/62 mmHg, HR 67 bpm. She was treated with oral Benadryl and recovered on 18 Jun. 2009. The IP was discontinued on 17 Jun. 2009. The causal assessment was related per the investigator. The allergic reaction was adjudicated as anaphylactic reaction and possibly related to the IP by the ARAC.

Patient 840635033 (lixisenatide): A 58-year-old female patient with a medical history of hypertension, dyslipidemia, asthma, allergic rhinitis and allergies to drug and house dust, as well as rash in the past, developed pruritus and urticaria of severe intensity on 19 Jul. 2009 (25 days on the IP) following administration with the IP and oral metoclopramide, (newly started on 19 Jul. 2009 and stopped on 20 Jul. 2009). The patient complained of generalized itching, flushing, swelling in lips, eyes and face, nasal congestion and feeling nausea. The vital signs during a reaction (23 Jul. 2009, 10:10) were: BP134/66 mmHg, HR 95 bpm. She was treated with oral Benadryl and rapidly improved. The IP was discontinued on 23 Jul. 2009. The causal assessment was related to the IP but also possibly to metoclopramide per the investigator. The allergic reaction was adjudicated as anaphylactic reaction and possibly related to the IP by the ARAC.

TABLE 29

Number (%) of patients with events adjudicated as allergic reaction by ARAC during the on-treatment period of the whole study - Safety population

| Relationship to study treatment (by ARAC) | MedDRA coded term (PT) for ARAC diagnosis | ARAC diagnosis | Placebo (N = 167) | Lixisenatide (N = 328) |
|---|---|---|---|---|
| All | Events adjudicated as allergic reaction by ARAC | | 3 (1.8%) | 8 (2.4%) |
| | Anaphylactic reaction | ANAPHYLACTIC REACTION | 0 | 2 (0.6%) |
| | Angioedema | ANGIOEDEMA | 2 (1.2%) | 0 |
| | Asthma | ASTHMA EXACERBATION | 0 | 1 (0.3%) |

TABLE 29-continued

Number (%) of patients with events adjudicated as allergic reaction by ARAC during the on-treatment period of the whole study - Safety population

| Relationship to study treatment (by ARAC) | MedDRA coded term (PT) for ARAC diagnosis | ARAC diagnosis | Placebo (N = 167) | Lixisenatide (N = 328) |
|---|---|---|---|---|
| | Dermatitis contact | ALLERGIC CONTACT DERMATITIS | 0 | 1 (0.3%) |
| | Dermatitis | DRUG-INDUCED DERMATITIS | 1 (0.6%) | 0 |
| | Pruritus | PRURITUS | 0 | 1 (0.3%) |
| | Rhinitis allergic | ALLERGIC RHINITIS | 0 | 1 (0.3%) |
| | Urticaria | URTICARIA (HIVES) | 0 | 2 (0.6%) |
| Possibly Related to IP | Events adjudicated as allergic reaction by ARAC | | 1 (0.6%) | 2 (0.6%) |
| | Anaphylactic reaction | ANAPHYLACTIC REACTION | 0 | 2 (0.6%) |
| | Angioedema | ANGIOEDEMA | 1 (0.6%) | 0 |
| Not related to IP | Events adjudicated as allergic reaction by ARAC | | 2 (1.2%) | 6 (1.8%) |
| | Angioedema | ANGIOEDEMA | 1 (0.6%) | 0 |
| | Asthma | ASTHMA EXACERBATION | 0 | 1 (0.3%) |
| | Dermatitis contact | ALLERGIC CONTACT DERMATITIS | 0 | 1 (0.3%) |
| | Dermatitis | DRUG-INDUCED DERMATITIS | 1 (0.6%) | 0 |
| | Pruritus | PRURITUS | 0 | 1 (0.3%) |
| | Rhinitis allergic | ALLERGIC RHINITIS | 0 | 1 (0.3%) |
| | Urticaria | URTICARIA (HIVES) | 0 | 2 (0.6%) |

ARAC = Allergic Reaction Assessment Committee.
IP = Investigational product.
On-treatment period for the whole study = the time from the first dose of double-blind study medication up to 3 days after the last dose administration.

Per protocol, any increase in amylase and/or lipase above twice the upper limit of normal range (ULN) that had been confirmed by a repeat measurement was to be monitored and documented on a pre-specified form: "adverse event form for suspected pancreatitis". During the on-treatment period for the whole study, 6 (1.8%) lixisenatide-treated patients and 1 (0.6%) placebo-treated patient reported 7 TEAEs with the pre-specified AE form (Table 30). Among these 7 patients, one lixisenatide-treated patient (#840614004) had an AE of pancreatitis.

Patient 840614004 (lixisenatide): A 60-year-old male patient with a medical history of prostatic hyperplasia, dislocated lumbar disc (L4), acid reflux, hypertension, depression, liver resection due to liver abscess and chronic smoking, was on insulin glargine, metformin and other concomitant medications including anti-hypertensive, antacids, and anti-inflammatory and pain medications.

On 5 Apr. 2010 (272 days on the IP), the patient was hospitalized for pancreatitis of severe intensity and the IP was discontinued. The patient complained of on-and-off recurrent diarrhea associated with nausea, vomiting and cramping epigastric pain for one week. The amylase was 166 IU/L and lipase was 40 U/L. His symptoms improved and he was discharged from the hospital on 8 Apr. 2010, but his lipase continued to increase. On 6 May 2010, the patient had a gastroenterology evaluation and a computed tomography (CT) revealed dilatation of the pancreatic ducts, apparently due to chronic pancreatitis. On 24 Jun. 2010, 11 weeks after the last dose of the IP, the patient developed severe exacerbation of pancreatitis and was hospitalized. The patient presented with acute abdominal pain with multiple episodes of vomiting. The patient's amylase level was 159 U/L and lipase was 1108 U/L. The patient recovered from the pancreatitis exacerbation on 27 Jun. 2010 and the causal assessment was not related to the IP per the investigator.

Patients who had at least one value of lipase or amylase≥3 ULN during the on-treatment period are summarized in Table 31. Ten patients (7 [2.2%] patients in the lixisenatide group and 3 [1.8%] in the placebo group) with elevated lipase 3 ULN) were observed. One patient in the lixisenatide group had elevated amylase 3 ULN), and none did in the placebo group.

TABLE 30

Number (%) of patients with TEAE suspected pancreatitis during the on-treatment period for the whole study - Safety population

| Preferred Term | Placebo (N = 167) | Lixisenatide (N = 328) |
|---|---|---|
| Any | 1 (0.6%) | 6 (1.8%) |
| Hyperamylasaemia | 0 | 1 (0.3%) |
| Lipase increased | 1 (0.6%) | 3 (0.9%) |

TABLE 30-continued

Number (%) of patients with TEAE suspected pancreatitis during the on-treatment period for the whole study - Safety population

| Preferred Term | Placebo (N = 167) | Lixisenatide (N = 328) |
|---|---|---|
| Pancreatic enzymes increased | 0 | 1 (0.3%) |
| Pancreatitis | 0 | 1 (0.3%) |

On-treatment period for the whole study = the time from the first dose of double-blind study medication up to 3 days after the last dose administration.
n (%) = number and percentage of patients with any cases reported on the AE form for suspected pancreatitis along with complementary form.

TABLE 31

Pancreatic enzymes: Number (%) of patients with at least one post-baseline PCSA during the on-treatment period for the whole study according to baseline status - Safety population

| Laboratory criteria Baseline By PCSA criteria n/N1 (%) | Placebo (N = 167) | Lixisenatide (N = 328) |
|---|---|---|
| Lipase | | |
| Total* | | |
| ≥3 ULN | 3/163 (1.8%) | 7/321 (2.2%) |
| Normal/Missing | | |
| ≥3 ULN | 3/162 (1.9%) | 7/321 (2.2%) |
| Amylase | | |
| Total* | | |
| ≥3 ULN | 0/163 | 1/321 (0.3%) |
| Normal/Missing | | |
| ≥3 ULN | 0/163 | 1/321 (0.3%) |

Note:
PCSA: Potentially Clinically Significant Abnormalities, ULN = Upper limit of normal.
On-treatment period for the whole study = the time from the first dose of double-blind study medication up to 3 days after the last dose administration.
*Regardless of baseline.
Note:
The number (n) represents the subset of the total number of patients who met the criterion in question at least once. The denominator (/N1) for each parameter within a treatment group is the number of patients for the treatment group who had that parameter assessed post-baseline by baseline PCSA status. Only the worsening of the worst case for each patient is presented by baseline status.

Per protocol, any calcitonin value≥20 pg/mL confirmed by a repeat measurement was to be monitored and reported on the pre-specified adverse event form for "increased calcitonin≥20 pg/mL". During the on-treatment period for whole study, 5 patients (4 [1.2%] for lixisenatide and 1 [0.6%] for placebo) reported 5 TEAEs of blood calcitonin increase (Table 32). Of these patients, 1 lixisenatide-treated patient (#840636032) had calcitonin values≥50 ng/L and 4 others had calcitonin values≥20 ng/L but<50 ng/L. In addition, one placebo-treated patient had a TEAE of "blood calcitonin increased" reported by the investigator (Table 35) although the values were <20 ng/L. This AE was not documented in the pre-specified AE form per protocol and therefore is not included in Table 32. A description of the case with calcitonin value≥50 ng/L is provided below:

Patient 840636032 (lixisenatide): A 55-year-old male patient with a medical history of depression, dyslipidemia and hypertension was on insulin glargine, metformin and other concomitant medications including multivitamins, gemfibrozil, valsartan, bupropion, fluoxetine and methylphenidate. On 24 Sep. 2009 (Week 24), an AE of "blood calcitonin increased" was reported for a value of 47.5 ng/L, which was the result of the first calcitonin measurement for this patient. The AE was not accompanied with any symptoms. Calcitonin rose to 75.9 and 70.7 ng/L in January and February, 2010 so the IP was discontinued. On 23 Feb. 2010, the patient saw a thyroid specialist and underwent a thyroid ultrasound scan, which revealed a "normal" result. The follow-up calcitonin (27 May 2010) was 50 ng/L. A repeat thyroid ultrasound (28 Jul. 2010) was again "normal". The thyroid specialist assessed the event as "an incidentally discovered elevation in calcitonin level is of unknown significance" and recommended serial monitoring of calcitonin through time and a repeat ultrasound in one year. The causal relationship was not related to the IP per the investigator. A post-study calcitonin on 23 Dec. 2010 was 60 pg/mL (local laboratory reference<11 pg/mL).

TABLE 32

Number (%) of patients with TEAE increased calcitonin during the on-treatment period for the whole study - Safety population

| Preferred Term | Placebo (N = 167) | Lixisenatide (N = 328) |
|---|---|---|
| Any | 1 (0.6%) | 4 (1.2%) |
| Blood calcitonin increased | 1 (0.6%) | 4 (1.2%) |

On-treatment period for the whole study = the time from the first dose of double-blind study medication up to 3 days after the last dose administration.
n (%) = number and percentage of patients with any cases reported on the AE form for increased calcitonin ≥ 20 pg/mL.

Patients with at least one serum calcitonin measured during the on-treatment period of the whole study are summarized in Table 33 according to the 4 categories of calcitonin level at baseline. Eight (2.8%) patients in the lixisenatide group and 1 (0.7%) patient in the placebo group had calcitonin values≥20 ng/L (Table 33) including those 5 patients (4 on lixisenatide) who reported a TEAE with the pre-specified AE form (Table 32). Four out of the 8 lixisenatide-treated patients with a calcitonin value≥20 ng/L (Table 33) did not report a TEAE with the pre-specified AE form because of an unconfirmed elevation; 2 had a single value≥50 ng/L (all other measurements≤20 ng/L) and 2 had a value between ≥20-<50 ng/L. It should be pointed out that calcitonin measurement was introduced into the protocol via a protocol amendment after most patients had been randomized. Therefore, baseline values are missing for the majority of the patients (209 [88.2%] for lixisenatide and 101 [88.6%] for placebo).

TABLE 33

Serum calcitonin - Number (%) of patients by pre-defined categories during the on-treatment period of the whole study according to baseline category - Safety population

| Laboratory criteria Baseline status Post-baseline | Placebo (N = 167) | Lixisenatide (N = 328) |
|---|---|---|
| Calcitonin (ng/L) | | |
| Total* | | |
| ≤ULN | 127/147 (86.4%) | 246/281 (87.5%) |
| >ULN-<20 ng/L | 19/147 (12.9%) | 27/281 (9.6%) |
| ≥20 ng/L-<50 ng/L | 1/147 (0.7%) | 5/281 (1.8%) |
| ≥50 ng/L | 0/147 | 3/281 (1.1%) |
| Missing | | |
| ≤ULN | 101/114 (88.6%) | 209/237 (88.2%) |
| >ULN-<20 ng/L | 13/114 (11.4%) | 22/237 (9.3%) |
| ≥20 ng/L-<50 ng/L | 0/114 | 3/237 (1.3%) |
| ≥50 ng/L | 0/114 | 3/237 (1.3%) |
| ≤ULN | | |
| ≤ULN | 26/29 (89.7%) | 37/39 (94.9%) |
| >ULN-<20 ng/L | 3/29 (10.3%) | 2/39 (5.1%) |
| ≥20 ng/L-<50 ng/L | 0/29 | 0/39 |
| ≥50 ng/L | 0/29 | 0/39 |
| >ULN-<20 ng/L | | |
| ≤ULN | 0/4 | 0/4 |
| >ULN-<20 ng/L | 3/4 (75.0%) | 3/4 (75.0%) |
| ≥20 ng/L-<50 ng/L | 1/4 (25.0%) | 1/4 (25.0%) |
| ≥50 ng/L | 0/4 | 0/4 |

TABLE 33-continued

Serum calcitonin - Number (%) of patients by pre-defined categories during the on-treatment period of the whole study according to baseline category - Safety population

| Laboratory criteria<br>Baseline status<br>Post-baseline | Placebo<br>(N = 167) | Lixisenatide<br>(N = 328) |
|---|---|---|
| ≥20 ng/L-<50 ng/L | | |
| ≤ULN | 0/0 | 0/1 |
| >ULN-<20 ng/L | 0/0 | 0/1 |
| ≥20 ng/L-<50 ng/L | 0/0 | 1/1 (100%) |
| ≥50 ng/L | 0/0 | 0/1 |
| ≥50 ng/L | | |
| ≤ULN | 0/0 | 0/0 |
| >ULN-<20 ng/L | 0/0 | 0/0 |
| ≥20 ng/L-<50 ng/L | 0/0 | 0/0 |
| ≥50 ng/L | 0/0 | 0/0 |

ULN = Upper limit of normal.
On-treatment period for the whole study = the time from the first dose of double-blind study medication up to 3 days after the last dose administration.
*Regardless of baseline.
Note:
The numerator represents the number of patients who were in the pre-specified categories in each baseline category. The denominator for each parameter within a treatment group is the number of patients for the treatment group who had that parameter assessed post-baseline by baseline status.
A patient is counted only in the worst category.

APPENDIX

TABLE 34

Mean change in HbA1c (%) from baseline by visit - mITT population

| Treatment | Observed data | | | | | | | Change from baseline | | | | | | |
|---|---|---|---|---|---|---|---|---|---|---|---|---|---|---|
| Time point | N | Mean | SD | SE | Median | Min | Max | N | Mean | SD | SE | Median | Min | Max |
| Placebo (N = 165) | | | | | | | | | | | | | | |
| Screening | 165 | 8.46 | 0.81 | 0.063 | 8.50 | 7.0 | 10.0 | | | | | | | |
| Baseline | 165 | 8.37 | 0.84 | 0.065 | 8.40 | 6.7 | 10.5 | | | | | | | |
| Week 8 | 147 | 8.09 | 1.02 | 0.084 | 8.00 | 6.1 | 11.6 | 147 | −0.31 | 0.68 | 0.056 | −0.30 | −2.1 | 1.4 |
| Week 12 | 145 | 8.04 | 1.12 | 0.093 | 7.90 | 5.9 | 11.6 | 145 | −0.33 | 0.85 | 0.070 | −0.30 | −2.5 | 1.9 |
| Week 24 | 134 | 8.07 | 1.16 | 0.101 | 7.80 | 6.0 | 11.6 | 134 | −0.28 | 1.04 | 0.090 | −0.40 | −2.7 | 2.7 |
| Week 24 (LOCF) | 158 | 8.13 | 1.17 | 0.093 | 7.90 | 6.0 | 11.6 | 158 | −0.24 | 0.98 | 0.078 | −0.30 | −2.7 | 2.7 |
| Week 36 | 115 | 7.98 | 1.08 | 0.101 | 7.90 | 5.6 | 11.3 | 115 | −0.32 | 1.01 | 0.094 | −0.30 | −3.0 | 3.0 |
| Week 44 | 103 | 7.83 | 1.00 | 0.099 | 7.70 | 6.0 | 11.7 | 103 | −0.40 | 0.95 | 0.094 | −0.40 | −2.9 | 2.9 |
| Week 52 | 94 | 7.71 | 0.99 | 0.102 | 7.65 | 5.7 | 12.1 | 94 | −0.47 | 0.98 | 0.101 | −0.45 | −2.8 | 3.6 |
| Week 60 | 81 | 7.70 | 1.15 | 0.128 | 7.50 | 5.8 | 12.3 | 81 | −0.50 | 1.08 | 0.119 | −0.50 | −3.1 | 4.5 |
| Week 68 | 76 | 7.64 | 1.02 | 0.117 | 7.50 | 5.8 | 11.2 | 76 | −0.50 | 1.03 | 0.118 | −0.50 | −2.9 | 2.5 |
| Week 76 | 67 | 7.69 | 1.00 | 0.123 | 7.40 | 6.0 | 11.6 | 67 | −0.43 | 1.04 | 0.127 | −0.40 | −2.8 | 2.9 |
| Week 84 | 29 | 7.82 | 1.19 | 0.221 | 7.80 | 5.7 | 11.2 | 29 | −0.35 | 0.99 | 0.184 | −0.40 | −1.7 | 2.4 |
| Week 92 | 21 | 7.87 | 1.06 | 0.232 | 7.70 | 5.7 | 10.2 | 21 | −0.20 | 1.07 | 0.235 | 0.10 | −1.8 | 2.1 |
| Week 100 | 11 | 7.98 | 0.87 | 0.261 | 7.60 | 7.1 | 9.6 | 11 | 0.02 | 0.84 | 0.254 | −0.10 | −1.3 | 1.4 |
| Week 108 | 5 | 7.76 | 0.30 | 0.133 | 7.80 | 7.3 | 8.1 | 5 | −0.22 | 0.40 | 0.180 | −0.20 | −0.8 | 0.2 |
| Last on-treatment value | 158 | 8.24 | 1.12 | 0.089 | 8.20 | 5.7 | 12.0 | 158 | −0.13 | 0.96 | 0.076 | −0.10 | −2.8 | 2.7 |
| Lixisenatide (N = 326) | | | | | | | | | | | | | | |
| Screening | 326 | 8.49 | 0.83 | 0.046 | 8.50 | 7.0 | 10.0 | | | | | | | |
| Baseline | 326 | 8.42 | 0.88 | 0.049 | 8.40 | 6.0 | 10.8 | | | | | | | |
| Week 8 | 286 | 7.68 | 1.00 | 0.059 | 7.60 | 5.5 | 14.1 | 286 | −0.72 | 0.86 | 0.051 | −0.70 | −2.8 | 5.7 |
| Week 12 | 272 | 7.54 | 0.94 | 0.057 | 7.40 | 5.5 | 10.9 | 272 | −0.84 | 0.86 | 0.052 | −0.90 | −3.0 | 2.5 |
| Week 24 | 251 | 7.65 | 1.11 | 0.070 | 7.50 | 5.6 | 11.3 | 251 | −0.72 | 1.01 | 0.064 | −0.80 | −3.5 | 2.9 |
| Week 24 (LOCF) | 304 | 7.76 | 1.18 | 0.068 | 7.60 | 5.6 | 14.1 | 304 | −0.63 | 1.08 | 0.062 | −0.60 | −3.5 | 5.7 |
| Week 36 | 220 | 7.60 | 1.09 | 0.073 | 7.40 | 5.5 | 12.0 | 220 | −0.74 | 1.01 | 0.068 | −0.80 | −3.6 | 2.6 |
| Week 44 | 191 | 7.52 | 1.11 | 0.080 | 7.50 | 5.3 | 11.7 | 191 | −0.75 | 1.07 | 0.078 | −0.80 | −3.8 | 2.9 |
| Week 52 | 183 | 7.49 | 1.16 | 0.086 | 7.40 | 5.3 | 11.8 | 183 | −0.74 | 1.10 | 0.081 | −0.80 | −3.5 | 2.9 |
| Week 60 | 163 | 7.50 | 1.18 | 0.092 | 7.30 | 5.4 | 12.4 | 163 | −0.71 | 1.16 | 0.091 | −0.70 | −3.5 | 4.0 |
| Week 68 | 155 | 7.43 | 1.19 | 0.095 | 7.30 | 5.1 | 12.5 | 155 | −0.76 | 1.14 | 0.092 | −0.80 | −3.1 | 4.0 |
| Week 76 | 150 | 7.39 | 1.15 | 0.094 | 7.30 | 5.3 | 13.7 | 150 | −0.79 | 1.16 | 0.094 | −0.95 | −2.9 | 5.5 |
| Week 84 | 87 | 7.30 | 1.04 | 0.111 | 7.30 | 5.3 | 10.9 | 87 | −0.90 | 1.10 | 0.118 | −1.00 | −3.2 | 2.4 |
| Week 92 | 58 | 7.06 | 0.92 | 0.120 | 7.05 | 5.0 | 9.5 | 58 | −1.05 | 0.94 | 0.124 | −1.10 | −2.9 | 1.4 |
| Week 100 | 29 | 6.91 | 0.93 | 0.173 | 6.80 | 5.5 | 9.6 | 29 | −0.98 | 0.96 | 0.179 | −1.00 | −3.0 | 0.9 |
| Week 108 | 18 | 6.77 | 0.85 | 0.201 | 6.65 | 5.4 | 8.6 | 18 | −1.01 | 0.97 | 0.228 | −1.10 | −2.5 | 1.4 |
| Week 116 | 6 | 7.05 | 1.26 | 0.516 | 7.05 | 5.5 | 9.0 | 6 | −0.68 | 1.01 | 0.414 | −0.75 | −2.3 | 0.7 |
| Week 124 | 2 | 7.15 | 1.77 | 1.250 | 7.15 | 5.9 | 8.4 | 2 | −0.45 | 0.78 | 0.550 | −0.45 | −1.0 | 0.1 |

TABLE 34-continued

Mean change in HbA1c (%) from baseline by visit - mITT population

| Treatment | Observed data | | | | | | | Change from baseline | | | | | | |
|---|---|---|---|---|---|---|---|---|---|---|---|---|---|---|
| Time point | N | Mean | SD | SE | Median | Min | Max | N | Mean | SD | SE | Median | Min | Max |
| Last on-treatment value | 304 | 7.96 | 1.18 | 0.067 | 7.90 | 5.3 | 14.1 | 304 | −0.44 | 1.10 | 0.063 | −0.45 | −3.1 | 5.7 |

LOCF = Last observation carried forward.
The analysis excluded measurements obtained after the introduction of rescue medication and/or after the treatment cessation plus 3 days.
For Week 24 (LOCF), the analysis included measurements obtained up to 3 days after the last dose of the double-blind investigational product injection on or before Visit 12 (Week24), or Day 169 if Visit 12 (Week 24) is not available.

TABLE 35

Number (%) of patients experiencing common TEAE(s) (PT ≥ 1% in any treatment group) during the overall treatment period presented by primary SOC, HLGT, HLT and PT - Safety population

| PRIMARY SYSTEM ORGAN CLASS<br>  HLGT: High Level Group Term<br>    HLT: High Level Term<br>      Preferred Term | Placebo<br>(N = 167) | Lixisenatide<br>(N = 328) |
|---|---|---|
| Any class | 143 (85.6%) | 287 (87.5%) |
| INFECTIONS AND INFESTATIONS | 72 (43.1%) | 148 (45.1%) |
|   HLGT: Fungal infectious disorders | 3 (1.8%) | 12 (3.7%) |
|     HLT: Fungal infections NEC | 3 (1.8%) | 8 (2.4%) |
|       Fungal skin infection | 2 (1.2%) | 0 |
|       Onychomycosis | 0 | 4 (1.2%) |
|   HLGT: Infections - pathogen unspecified | 60 (35.9%) | 125 (38.1%) |
|     HLT: Abdominal and gastrointestinal infections | 5 (3.0%) | 14 (4.3%) |
|       Gastroenteritis | 4 (2.4%) | 12 (3.7%) |
|     HLT: Dental and oral soft tissue infections | 4 (2.4%) | 7 (2.1%) |
|       Tooth infection | 2 (1.2%) | 5 (1.5%) |
|     HLT: Ear infections | 3 (1.8%) | 6 (1.8%) |
|       Ear infection | 2 (1.2%) | 0 |
|     HLT: Infections NEC | 3 (1.8%) | 5 (1.5%) |
|       Localised infection | 2 (1.2%) | 3 (0.9%) |
|     HLT: Lower respiratory tract and lung infections | 15 (9.0%) | 26 (7.9%) |
|       Bronchitis | 13 (7.8%) | 22 (6.7%) |
|       Pneumonia | 2 (1.2%) | 5 (1.5%) |
|     HLT: Upper respiratory tract infections | 40 (24.0%) | 84 (25.6%) |
|       Laryngitis | 3 (1.8%) | 0 |
|       Nasopharyngitis | 21 (12.6%) | 32 (9.8%) |
|       Pharyngitis | 5 (3.0%) | 12 (3.7%) |
|       Pharyngotonsillitis | 3 (1.8%) | 1 (0.3%) |
|       Rhinitis | 2 (1.2%) | 3 (0.9%) |
|       Sinusitis | 5 (3.0%) | 12 (3.7%) |
|       Upper respiratory tract infection | 6 (3.6%) | 24 (7.3%) |
|     HLT: Urinary tract infections | 7 (4.2%) | 26 (7.9%) |
|       Urinary tract infection | 6 (3.6%) | 21 (6.4%) |
|   HLGT: Viral infectious disorders | 22 (13.2%) | 41 (12.5%) |
|     HLT: Herpes viral infections | 3 (1.8%) | 1 (0.3%) |
|       Herpes zoster | 3 (1.8%) | 1 (0.3%) |
|     HLT: Influenza viral infections | 9 (5.4%) | 28 (8.5%) |
|       Influenza | 9 (5.4%) | 28 (8.5%) |
|     HLT: Viral infections NEC | 11 (6.6%) | 11 (3.4%) |
|       Gastroenteritis viral | 4 (2.4%) | 4 (1.2%) |
|       Respiratory tract infection viral | 5 (3.0%) | 3 (0.9%) |
| NEOPLASMS BENIGN, MALIGNANT AND UNSPECIFIED (INCL CYSTS AND POLYPS) | 7 (4.2%) | 11 (3.4%) |
|   HLGT: Endocrine neoplasms malignant and unspecified | 2 (1.2%) | 2 (0.6%) |
|     HLT: Endocrine neoplasms malignant and unspecified NEC | 2 (1.2%) | 2 (0.6%) |
|       Thyroid neoplasm | 2 (1.2%) | 2 (0.6%) |
| BLOOD AND LYMPHATIC SYSTEM DISORDERS | 6 (3.6%) | 9 (2.7%) |
|   HLGT: Anaemias nonhaemolytic and marrow depression | 5 (3.0%) | 7 (2.1%) |
|     HLT: Anaemias NEC | 4 (2.4%) | 6 (1.8%) |
|       Anaemia | 3 (1.8%) | 6 (1.8%) |
| METABOLISM AND NUTRITION DISORDERS | 72 (43.1%) | 151 (46.0%) |
|   HLGT: Appetite and general nutritional disorders | 3 (1.8%) | 13 (4.0%) |
|     HLT: Appetite disorders | 3 (1.8%) | 13 (4.0%) |
|       Decreased appetite | 2 (1.2%) | 11 (3.4%) |

TABLE 35-continued

Number (%) of patients experiencing common TEAE(s) (PT ≥ 1% in any treatment group) during the overall treatment period presented by primary SOC, HLGT, HLT and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| HLGT: Glucose metabolism disorders (incl diabetes mellitus) | 68 (40.7%) | 141 (43.0%) |
| HLT: Hypoglycaemic conditions NEC | 68 (40.7%) | 141 (43.0%) |
| Hypoglycaemia | 68 (40.7%) | 138 (42.1%) |
| Hypoglycaemia unawareness | 2 (1.2%) | 9 (2.7%) |
| HLGT: Lipid metabolism disorders | 2 (1.2%) | 8 (2.4%) |
| HLT: Elevated triglycerides | 2 (1.2%) | 6 (1.8%) |
| Hypertriglyceridaemia | 2 (1.2%) | 6 (1.8%) |
| HLGT: Purine and pyrimidine metabolism disorders | 1 (0.6%) | 7 (2.1%) |
| HLT: Purine metabolism disorders NEC | 1 (0.6%) | 7 (2.1%) |
| Hyperuricaemia | 0 | 5 (1.5%) |
| PSYCHIATRIC DISORDERS | 13 (7.8%) | 25 (7.6%) |
| HLGT: Anxiety disorders and symptoms | 7 (4.2%) | 11 (3.4%) |
| HLT: Anxiety symptoms | 7 (4.2%) | 10 (3.0%) |
| Anxiety | 4 (2.4%) | 7 (2.1%) |
| Stress | 3 (1.8%) | 0 |
| HLGT: Depressed mood disorders and disturbances | 3 (1.8%) | 8 (2.4%) |
| HLT: Depressive disorders | 3 (1.8%) | 8 (2.4%) |
| Depression | 3 (1.8%) | 8 (2.4%) |
| HLGT: Sleep disorders and disturbances | 5 (3.0%) | 5 (1.5%) |
| HLT: Disturbances in initiating and maintaining sleep | 5 (3.0%) | 4 (1.2%) |
| Insomnia | 5 (3.0%) | 4 (1.2%) |
| NERVOUS SYSTEM DISORDERS | 48 (28.7%) | 95 (29.0%) |
| HLGT: Headaches | 17 (10.2%) | 44 (13.4%) |
| HLT: Headaches NEC | 17 (10.2%) | 41 (12.5%) |
| Headache | 17 (10.2%) | 41 (12.5%) |
| HLT: Migraine headaches | 0 | 4 (1.2%) |
| Migraine | 0 | 4 (1.2%) |
| HLGT: Movement disorders (incl parkinsonism) | 6 (3.6%) | 18 (5.5%) |
| HLT: Tremor (excl congenital) | 6 (3.6%) | 18 (5.5%) |
| Tremor | 6 (3.6%) | 18 (5.5%) |
| HLGT: Neurological disorders NEC | 19 (11.4%) | 45 (13.7%) |
| HLT: Disturbances in consciousness NEC | 0 | 6 (1.8%) |
| Somnolence | 0 | 5 (1.5%) |
| HLT: Neurological signs and symptoms NEC | 11 (6.6%) | 28 (8.5%) |
| Dizziness | 11 (6.6%) | 26 (7.9%) |
| HLT: Paraesthesias and dysaesthesias | 5 (3.0%) | 10 (3.0%) |
| Paraesthesia | 4 (2.4%) | 10 (3.0%) |
| HLT: Sensory abnormalities NEC | 6 (3.6%) | 4 (1.2%) |
| Hypoaesthesia | 2 (1.2%) | 3 (0.9%) |
| Restless legs syndrome | 2 (1.2%) | 0 |
| HLGT: Peripheral neuropathies | 9 (5.4%) | 10 (3.0%) |
| HLT: Chronic polyneuropathies | 6 (3.6%) | 3 (0.9%) |
| Diabetic neuropathy | 6 (3.6%) | 3 (0.9%) |
| HLT: Mononeuropathies | 1 (0.6%) | 5 (1.5%) |
| Carpal tunnel syndrome | 1 (0.6%) | 4 (1.2%) |
| HLGT: Spinal cord and nerve root disorders | 2 (1.2%) | 7 (2.1%) |
| HLT: Lumbar spinal cord and nerve root disorders | 2 (1.2%) | 7 (2.1%) |
| Sciatica | 2 (1.2%) | 7 (2.1%) |
| EYE DISORDERS | 18 (10.8%) | 38 (11.6%) |
| HLGT: Anterior eye structural change, deposit and degeneration | 4 (2.4%) | 9 (2.7%) |
| HLT: Cataract conditions | 4 (2.4%) | 8 (2.4%) |
| Cataract | 4 (2.4%) | 8 (2.4%) |
| HLGT: Eye disorders NEC | 4 (2.4%) | 1 (0.3%) |
| HLT: Ocular disorders NEC | 4 (2.4%) | 0 |
| Eye pain | 4 (2.4%) | 0 |
| HLGT: Glaucoma and ocular hypertension | 0 | 5 (1.5%) |
| HLT: Glaucomas (excl congenital) | 0 | 5 (1.5%) |
| Glaucoma | 0 | 5 (1.5%) |
| HLGT: Ocular infections, irritations and inflammations | 2 (1.2%) | 7 (2.1%) |
| HLT: Conjunctival infections, irritations and inflammations | 2 (1.2%) | 4 (1.2%) |
| Conjunctivitis | 2 (1.2%) | 4 (1.2%) |
| HLGT: Retina, choroid and vitreous haemorrhages and vascular disorders | 4 (2.4%) | 10 (3.0%) |
| HLT: Retinopathies NEC | 4 (2.4%) | 8 (2.4%) |
| Diabetic retinopathy | 3 (1.8%) | 6 (1.8%) |
| HLGT: Vision disorders | 4 (2.4%) | 12 (3.7%) |
| HLT: Visual disorders NEC | 3 (1.8%) | 9 (2.7%) |

TABLE 35-continued

Number (%) of patients experiencing common TEAE(s) (PT ≥ 1% in any treatment group) during the overall treatment period presented by primary SOC, HLGT, HLT and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| Vision blurred | 2 (1.2%) | 9 (2.7%) |
| EAR AND LABYRINTH DISORDERS | 5 (3.0%) | 14 (4.3%) |
| HLGT: Inner ear and VIIIth cranial nerve disorders | 4 (2.4%) | 10 (3.0%) |
| HLT: Inner ear signs and symptoms | 4 (2.4%) | 10 (3.0%) |
| Tinnitus | 2 (1.2%) | 3 (0.9%) |
| Vertigo | 2 (1.2%) | 7 (2.1%) |
| CARDIAC DISORDERS | 14 (8.4%) | 21 (6.4%) |
| HLGT: Cardiac arrhythmias | 3 (1.8%) | 13 (4.0%) |
| HLT: Rate and rhythm disorders NEC | 1 (0.6%) | 6 (1.8%) |
| Tachycardia | 0 | 6 (1.8%) |
| HLGT: Coronary artery disorders | 11 (6.6%) | 6 (1.8%) |
| HLT: Coronary artery disorders NEC | 5 (3.0%) | 2 (0.6%) |
| Coronary artery disease | 5 (3.0%) | 2 (0.6%) |
| HLT: Ischaemic coronary artery disorders | 9 (5.4%) | 4 (1.2%) |
| Acute myocardial infarction | 2 (1.2%) | 1 (0.3%) |
| Angina pectoris | 5 (3.0%) | 2 (0.6%) |
| VASCULAR DISORDERS | 14 (8.4%) | 34 (10.4%) |
| HLGT: Vascular hypertensive disorders | 12 (7.2%) | 23 (7.0%) |
| HLT: Accelerated and malignant hypertension | 3 (1.8%) | 6 (1.8%) |
| Hypertensive crisis | 3 (1.8%) | 6 (1.8%) |
| HLT: Vascular hypertensive disorders NEC | 9 (5.4%) | 17 (5.2%) |
| Hypertension | 9 (5.4%) | 17 (5.2%) |
| RESPIRATORY, THORACIC AND MEDIASTINAL DISORDERS | 18 (10.8%) | 39 (11.9%) |
| HLGT: Respiratory disorders NEC | 13 (7.8%) | 26 (7.9%) |
| HLT: Breathing abnormalities | 4 (2.4%) | 1 (0.3%) |
| Dyspnoea | 2 (1.2%) | 0 |
| Dyspnoea exertional | 2 (1.2%) | 1 (0.3%) |
| HLT: Coughing and associated symptoms | 3 (1.8%) | 14 (4.3%) |
| Cough | 3 (1.8%) | 14 (4.3%) |
| HLT: Upper respiratory tract signs and symptoms | 5 (3.0%) | 17 (5.2%) |
| Oropharyngeal pain | 2 (1.2%) | 13 (4.0%) |
| HLGT: Upper respiratory tract disorders (excl infections) | 2 (1.2%) | 12 (3.7%) |
| HLT: Paranasal sinus disorders (excl infections and neoplasms) | 0 | 4 (1.2%) |
| Sinus congestion | 0 | 4 (1.2%) |
| GASTROINTESTINAL DISORDERS | 43 (25.7%) | 153 (46.6%) |
| HLGT: Dental and gingival conditions | 7 (4.2%) | 12 (3.7%) |
| HLT: Dental pain and sensation disorders | 4 (2.4%) | 5 (1.5%) |
| Toothache | 4 (2.4%) | 5 (1.5%) |
| HLGT: Gastrointestinal inflammatory conditions | 4 (2.4%) | 4 (1.2%) |
| HLT: Gastritis (excl infective) | 2 (1.2%) | 4 (1.2%) |
| Gastritis | 2 (1.2%) | 3 (0.9%) |
| HLGT: Gastrointestinal motility and defaecation conditions | 14 (8.4%) | 52 (15.9%) |
| HLT: Diarrhoea (excl infective) | 10 (6.0%) | 38 (11.6%) |
| Diarrhoea | 10 (6.0%) | 37 (11.3%) |
| HLT: Gastrointestinal atonic and hypomotility disorders NEC | 4 (2.4%) | 19 (5.8%) |
| Constipation | 4 (2.4%) | 16 (4.9%) |
| Gastrooesophageal reflux disease | 0 | 4 (1.2%) |
| HLGT: Gastrointestinal signs and symptoms | 23 (13.8%) | 126 (38.4%) |
| HLT: Dyspeptic signs and symptoms | 1 (0.6%) | 17 (5.2%) |
| Dyspepsia | 1 (0.6%) | 17 (5.2%) |
| HLT: Flatulence, bloating and distension | 1 (0.6%) | 11 (3.4%) |
| Abdominal distension | 1 (0.6%) | 6 (1.8%) |
| Flatulence | 0 | 7 (2.1%) |
| HLT: Gastrointestinal and abdominal pains (excl oral and throat) | 5 (3.0%) | 21 (6.4%) |
| Abdominal pain | 2 (1.2%) | 9 (2.7%) |
| Abdominal pain upper | 3 (1.8%) | 13 (4.0%) |
| HLT: Gastrointestinal signs and symptoms NEC | 3 (1.8%) | 5 (1.5%) |
| Abdominal discomfort | 2 (1.2%) | 3 (0.9%) |
| HLT: Nausea and vomiting symptoms | 17 (10.2%) | 104 (31.7%) |
| Nausea | 16 (9.6%) | 96 (29.3%) |
| Vomiting | 2 (1.2%) | 32 (9.8%) |
| SKIN AND SUBCUTANEOUS TISSUE DISORDERS | 21 (12.6%) | 37 (11.3%) |
| HLGT: Angioedema and urticaria | 0 | 6 (1.8%) |
| HLT: Urticarias | 0 | 6 (1.8%) |
| Urticaria | 0 | 6 (1.8%) |

TABLE 35-continued

Number (%) of patients experiencing common TEAE(s) (PT ≥ 1% in any treatment group) during the overall treatment period presented by primary SOC, HLGT, HLT and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| HLGT: Epidermal and dermal conditions | 11 (6.6%) | 17 (5.2%) |
| HLT: Dermatitis and eczema | 4 (2.4%) | 3 (0.9%) |
| Dermatitis | 2 (1.2%) | 0 |
| HLT: Pruritus NEC | 3 (1.8%) | 7 (2.1%) |
| Pruritus | 3 (1.8%) | 5 (1.5%) |
| HLT: Rashes, eruptions and exanthems NEC | 2 (1.2%) | 2 (0.6%) |
| Rash | 2 (1.2%) | 2 (0.6%) |
| HLGT: Skin appendage conditions | 8 (4.8%) | 13 (4.0%) |
| HLT: Apocrine and eccrine gland disorders | 5 (3.0%) | 11 (3.4%) |
| Cold sweat | 2 (1.2%) | 1 (0.3%) |
| Hyperhidrosis | 3 (1.8%) | 10 (3.0%) |
| HLT: Rosaceas | 2 (1.2%) | 0 |
| Rosacea | 2 (1.2%) | 0 |
| MUSCULOSKELETAL AND CONNECTIVE TISSUE DISORDERS | 38 (22.8%) | 90 (27.4%) |
| HLGT: Joint disorders | 13 (7.8%) | 27 (8.2%) |
| HLT: Joint related signs and symptoms | 11 (6.6%) | 16 (4.9%) |
| Arthralgia | 11 (6.6%) | 16 (4.9%) |
| HLT: Osteoarthropathies | 2 (1.2%) | 9 (2.7%) |
| Osteoarthritis | 2 (1.2%) | 9 (2.7%) |
| HLGT: Muscle disorders | 7 (4.2%) | 16 (4.9%) |
| HLT: Muscle pains | 4 (2.4%) | 8 (2.4%) |
| Myalgia | 4 (2.4%) | 5 (1.5%) |
| HLT: Muscle related signs and symptoms NEC | 2 (1.2%) | 7 (2.1%) |
| Muscle spasms | 2 (1.2%) | 7 (2.1%) |
| HLGT: Musculoskeletal and connective tissue disorders NEC | 23 (13.8%) | 55 (16.8%) |
| HLT: Musculoskeletal and connective tissue pain and discomfort | 23 (13.8%) | 52 (15.9%) |
| Back pain | 11 (6.6%) | 24 (7.3%) |
| Musculoskeletal pain | 6 (3.6%) | 10 (3.0%) |
| Pain in extremity | 7 (4.2%) | 15 (4.6%) |
| HLGT: Tendon, ligament and cartilage disorders | 1 (0.6%) | 7 (2.1%) |
| HLT: Tendon disorders | 1 (0.6%) | 7 (2.1%) |
| Tendonitis | 1 (0.6%) | 6 (1.8%) |
| RENAL AND URINARY DISORDERS | 8 (4.8%) | 16 (4.9%) |
| HLGT: Nephropathies | 2 (1.2%) | 1 (0.3%) |
| HLT: Nephropathies and tubular disorders NEC | 2 (1.2%) | 1 (0.3%) |
| Diabetic nephropathy | 2 (1.2%) | 1 (0.3%) |
| HLGT: Renal disorders (excl nephropathies) | 3 (1.8%) | 3 (0.9%) |
| HLT: Renal failure and impairment | 3 (1.8%) | 3 (0.9%) |
| Renal failure | 2 (1.2%) | 0 |
| HLGT: Urinary tract signs and symptoms | 2 (1.2%) | 8 (2.4%) |
| HLT: Bladder and urethral symptoms | 1 (0.6%) | 4 (1.2%) |
| Dysuria | 1 (0.6%) | 4 (1.2%) |
| GENERAL DISORDERS AND ADMINISTRATION SITE CONDITIONS | 34 (20.4%) | 69 (21.0%) |
| HLGT: Body temperature conditions | 3 (1.8%) | 5 (1.5%) |
| HLT: Febrile disorders | 3 (1.8%) | 5 (1.5%) |
| Pyrexia | 3 (1.8%) | 5 (1.5%) |
| HLGT: General system disorders NEC | 30 (18.0%) | 59 (18.0%) |
| HLT: Asthenic conditions | 17 (10.2%) | 34 (10.4%) |
| Asthenia | 10 (6.0%) | 18 (5.5%) |
| Fatigue | 6 (3.6%) | 15 (4.6%) |
| Malaise | 2 (1.2%) | 3 (0.9%) |
| HLT: Feelings and sensations NEC | 2 (1.2%) | 7 (2.1%) |
| Hunger | 2 (1.2%) | 2 (0.6%) |
| HLT: Oedema NEC | 7 (4.2%) | 12 (3.7%) |
| Oedema peripheral | 7 (4.2%) | 8 (2.4%) |
| HLT: Pain and discomfort NEC | 7 (4.2%) | 12 (3.7%) |
| Chest pain | 4 (2.4%) | 1 (0.3%) |
| Non-cardiac chest pain | 1 (0.6%) | 6 (1.8%) |
| Pain | 1 (0.6%) | 4 (1.2%) |
| INVESTIGATIONS | 20 (12.0%) | 38 (11.6%) |
| HLGT: Endocrine investigations (incl sex hormones) | 2 (1.2%) | 4 (1.2%) |
| HLT: Gastrointestinal, pancreatic and APUD hormone analyses | 2 (1.2%) | 4 (1.2%) |
| Blood calcitonin increased | 2 (1.2%) | 4 (1.2%) |
| HLGT: Gastrointestinal investigations | 2 (1.2%) | 6 (1.8%) |
| HLT: Digestive enzymes | 2 (1.2%) | 6 (1.8%) |
| Lipase increased | 2 (1.2%) | 5 (1.5%) |

TABLE 35-continued

Number (%) of patients experiencing common TEAE(s) (PT ≥ 1% in any treatment group) during the overall treatment period presented by primary SOC, HLGT, HLT and PT - Safety population

| PRIMARY SYSTEM ORGAN CLASS<br>HLGT: High Level Group Term<br>HLT: High Level Term<br>Preferred Term | Placebo<br>(N = 167) | Lixisenatide<br>(N = 328) |
|---|---|---|
| HLGT: Hepatobiliary investigations | 4 (2.4%) | 3 (0.9%) |
| HLT: Liver function analyses | 4 (2.4%) | 3 (0.9%) |
| Alanine aminotransferase increased | 2 (1.2%) | 2 (0.6%) |
| HLGT: Metabolic, nutritional and blood gas investigations | 8 (4.8%) | 20 (6.1%) |
| HLT: Carbohydrate tolerance analyses (incl diabetes) | 7 (4.2%) | 19 (5.8%) |
| Blood glucose decreased | 7 (4.2%) | 19 (5.8%) |
| INJURY, POISONING AND PROCEDURAL COMPLICATIONS | 16 (9.6%) | 43 (13.1%) |
| HLGT: Bone and joint injuries | 6 (3.6%) | 13 (4.0%) |
| HLT: Upper limb fractures and dislocations | 3 (1.8%) | 1 (0.3%) |
| Wrist fracture | 3 (1.8%) | 0 |
| HLGT: Injuries NEC | 11 (6.6%) | 29 (8.8%) |
| HLT: Muscle, tendon and ligament injuries | 4 (2.4%) | 3 (0.9%) |
| Muscle strain | 3 (1.8%) | 3 (0.9%) |
| HLT: Non-site specific injuries NEC | 3 (1.8%) | 16 (4.9%) |
| Fall | 2 (1.2%) | 12 (3.7%) |
| HLT: Site specific injuries NEC | 3 (1.8%) | 4 (1.2%) |
| Tooth fracture | 2 (1.2%) | 2 (0.6%) |
| HLT: Skin injuries NEC | 3 (1.8%) | 8 (2.4%) |
| Contusion | 2 (1.2%) | 6 (1.8%) |
| Skin laceration | 2 (1.2%) | 1 (0.3%) |
| HLGT: Procedural related injuries and complications NEC | 2 (1.2%) | 2 (0.6%) |
| HLT: Non-site specific procedural complications | 2 (1.2%) | 1 (0.3%) |
| Procedural pain | 2 (1.2%) | 1 (0.3%) |
| SURGICAL AND MEDICAL PROCEDURES | 8 (4.8%) | 9 (2.7%) |
| HLGT: Vascular therapeutic procedures | 5 (3.0%) | 1 (0.3%) |
| HLT: Arterial therapeutic procedures (excl aortic) | 5 (3.0%) | 1 (0.3%) |
| Coronary angioplasty | 2 (1.2%) | 0 |
| Coronary artery bypass | 2 (1.2%) | 1 (0.3%) |

TEAE: Treatment emergent adverse event, SOC: System Organ Class, HLGT: High Level Group Term, HLT: High Level Term, PT: Preferred Term.
On-treatment period for the whole study = the time from the first dose of double-blind study medication up to 3 days after the last dose administration.
MedDRA version: 13.1.
n (%) = number and percentage of patients with at least one TEAE.
Note:
Table sorted by SOC internationally agreed order and HLGT, HLT, PT alphabetic order. Only SOC with at least one PT ≥ 1% in at least one group are presented.

---

The invention claimed is:

1. A method for improving glycemic control in a patient with type 2 diabetes mellitus comprising administering to the patient in need thereof a therapeutically effective amount of a pharmaceutical combination comprising:
   (a) lixisenatide or a pharmaceutically acceptable salt thereof, and
   (b) insulin glargine or a pharmaceutically acceptable salt thereof,
   wherein the patient's type 2 diabetes mellitus is inadequately controlled after treatment with basal insulin at a dose of about 15 units to about 80 units per day for at least about 3 months.

2. The method of claim 1, wherein the patient is an adult.

3. The method of claim 1, wherein the patient has a glycosylated hemoglobin $A_{1c}$ (Hb$A_{1c}$) value of about 7% to about 10% after treatment with basal insulin.

4. The method of claim 1, wherein the basal insulin is insulin glargine.

5. The method of claim 1, wherein the pharmaceutical combination comprises a daily dose of about 15 units to about 80 units of insulin glargine.

6. The method of claim 1, wherein the pharmaceutical combination comprises a daily dose of about 10 μg to about 20 μg of lixisenatide.

7. A method for improving glycemic control in a patient with type 2 diabetes mellitus, the method comprising administering to the patient in need thereof a therapeutically effective amount of a pharmaceutical combination comprising:
   (a) lixisenatide or a pharmaceutically acceptable salt thereof, and
   (b) insulin glargine or a pharmaceutically acceptable salt thereof,
   wherein the patient's type 2 diabetes mellitus is inadequately controlled after treatment with basal insulin at a dose of about 15 units to about 80 units per day and metformin at a dose of at least about 1.0 g per day for at least about 3 months.

8. The method of claim 7, wherein the basal insulin is insulin glargine.

9. The method of claim 7, wherein the pharmaceutical combination comprises a daily dose of about 15 units to about 80 units of insulin glargine.

10. The method of claim 7, wherein the pharmaceutical combination comprises a daily dose of about 10 μg to about 20 μg of lixisenatide.

11. The method of claim 7, wherein the patient is an adult.

12. The method of claim 7, wherein the patient has an Hb$A_{1c}$ value of about 7% to about 10% after treatment with basal insulin and metformin.

13. The method of claim 7, further comprising administering to the patient a therapeutically effective amount of metformin.

14. The method of claim 1 or 7, wherein the basal insulin is a long-acting basal insulin.

* * * * *